United States Patent [19]
Jadhav et al.

[11] Patent Number: 5,294,720
[45] Date of Patent: Mar. 15, 1994

[54] 1,4-DIAMINO-2,3-DIHYDROXYBUTANES

[75] Inventors: Prabhakar K. Jadhav, Wilmington, Del.; Lawrence R. McGee, Pacifica, Calif.; Ashok Shenvi; Carl N. Hodge, both of Wilmington, Del.

[73] Assignee: The DuPont Merck Pharmaceutical Co., Wilmington, Del.

[21] Appl. No.: 714,042

[22] Filed: May 31, 1991

Related U.S. Application Data

[63] Continuation-in-part of Ser. No. 531,971, Jun. 1, 1990, abandoned.

[51] Int. Cl.$^5$ .................... A61K 31/44; C07D 213/40
[52] U.S. Cl. ........................ 546/265; 514/18; 514/19; 514/824; 514/351; 514/352; 514/357
[58] Field of Search .............. 514/18, 19, 824, 351, 514/352, 357; 546/265

[56] References Cited

U.S. PATENT DOCUMENTS 5,151,438  9/1992  Sham et al. ................... 514/357

FOREIGN PATENT DOCUMENTS 2026382  9/1990  Canada .
0361341  4/1990  European Pat. Off. .
0402646  12/1990  European Pat. Off. .

OTHER PUBLICATIONS

Haber et al., *J. Cardiovasc. Pharmacol.*, 1987(10) (Supp. 7), pp. 554–558.
Burger, *Medicinal Chemistry*, Second Edition, June 27, 1960, Interscience Publishers, Inc., N.Y., N.Y., pp. 565–571, 578–581, 600, 601.
Bolis et al., *J. Med. Chem.*, 1987, 30(10), pp. 1729–1737.
Plattner et al., *J. Med. Chem.*, 1988, 31(12), pp. 2277–2288.
Denkewalter et al., *Progress in Drug Research*, 1966, vol. 10, pages 510–512.

*Primary Examiner*—Ronald W. Griffin
*Attorney, Agent, or Firm*—Gerald J. Boudreaux

[57] ABSTRACT

There are provided novel 1,4 Diamine 2,3 Dihydroxybutanes useful as antiviral agents, pharmaceutical compositions containing them and processes for preparing such compounds.

43 Claims, No Drawings

1,4-DIAMINO-2,3-DIHYDROXYBUTANES

This is a continuation-in-part of application Ser. No. 07/531,971 filed Jun. 1, 1990, now abandoned.

FIELD OF THE INVENTION

This invention relates to 1,4-diamino 2,3-dihydroxybutanes, a process to prepare these compounds, compositions comprising such compounds and a method of treating viral infection.

BACKGROUND OF THE INVENTION

Current treatments for viral diseases usually involve administration of compounds that inhibit viral DNA synthesis. Current treatments for AIDS (Dagani, *Chem. Eng. News*, Nov. 23, 1987 pp. 41–49) involve administration of compounds such as 2',3'-dideoxycytidine, trisodium phosphonoformate, ammonium 21-tungsto-9-antimoniate, 1-b-D-ribofuranoxyl-1,2,4-triazole-3-carboxamide, 3'-azido-3'-deoxythymidine, and adriamycin that inhibit viral DNA synthesis; compounds such as AL-721 and polymannoacetate which may prevent HIV from penetrating the host cell; and compounds which treat the opportunistic infections caused by the immunosupression resulting from HIV infection. None of the current AIDS treatments have proven to be totally effective in treating and/or reversing the disease. In addition, many of the compounds currently used to treat AIDS cause adverse side effects including low platelet count, renal toxicity and bone marrow cytopenia.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotension converting enzyme (ACE) to form the hypotensive peptide angiotensin II. Inhibitors of renin and ACE are known to reduce high blood pressure in vivo. However, no therapeutically useful renin protease inhibitors have been developed, due to problems of oral availability and in vivo stability. The genomes of retroviruses encode a protease that is responsible for the proteolytic processing of one or more polyprotein precursors such as the pol- and gag gene products. See Wellink, *Arch. Virol.* 98, 1 (1988). Retroviral proteases most commonly process the gag precursor into the core proteins, and also process the pol precursor into reverse transcriptase and retroviral protease.

The correct processing of the precursor polyproteins by the retroviral protease is necessary for the assembly of the infectious virions. It has been shown that in vitro mutagenesis that produces protease-defective virus leads to the production of immature core forms which lack infectivity. See Crawford, *J. Virol.* 53, 899 (1985); Katoh et al., *Virology* 145 280 (1985). Therefore, retroviral protease inhibition provides an attractive possible target for antiviral therapy. See Mitsuya, *Nature* 325 775 (1987).

Moore, *Biochem. Biophys. Res. Commun.*, 159 420 (1989) discloses peptidyl inhibitors of HIV protease. Erickson, European Patent Application No. WO 89/10752 discloses derivatives of peptides which are inhibitors of HIV protease.

U.S. Pat. No. 4,652,552 discloses methyl ketone derivatives of tetrapeptides as inhibitors of viral proteases. U.S. Pat. No. 4,644,055 discloses halomethyl derivatives of peptides as inhibitors of viral proteases. European Patent Application No. WO 87/07836 discloses L-glutamic acid gamma-monohydroxamate as an antiviral agent.

The ability to inhibit a protease provides a method for blocking viral replication and therefore a treatment for diseases, and AIDS in particular, that may have fewer side effects when compared to current treatments. The topic of this patent application is 1,4-dimino-2,3-dihydroxybutanes and the development of processes for the preparation of these diols which compounds are capable of inhibiting viral protease and which compounds are believed to serve as a means of combating viral diseases such as AIDS. The diols of this invention provide significant improvements over protease inhibitors that are known in the art. A large number of compounds have been reported to be renin inhibitors, but have suffered from lack of adequate bio-availability and are thus not useful as therapeutic agents. This poor activity has been ascribed to the unusually high molecular weight of renin inhibitors, to inadequate solubility properties, and to the presence of a number of peptide bonds, which are vulnerable to cleavage by mammalian proteases. The diols described herein have a distinct advantage in this regard, in that many do not contain peptide bonds, are of low molecular weight, and can be hydrophilic yet still inhibit the viral protease enzyme.

Additionally, many compounds that inhibit renin do not inhibit HIV protease. The structure-activity requirements of renin inhibitors differ from those of HIV protease inhibitors. The diols of the invention are particularly useful as HIV protease inhibitors.

Other HIV protease inhibitors have been reported, but to date very few have shown activity against viral replication in human cells. This lack of cellular activity is probably due to the factors discussed above for renin inhibitors. Unlike other HIV protease inhibitors, diols disclosed herein show potent inhibition of viral replication in human cells.

An additional advantage of the diols disclosed herein is that some of them are symmetrical. The symmetrical diols may offer improved binding potency to the HIV protease enzyme relative to dissymmetric counterparts, and are more readily prepared from inexpensive starting materials.

The 1,2-diol unit is one of the most ubiquitous functional groups in nature, and consequently a wealth of methods leading to its synthesis have been developed. Foremost in this arsenal are the catalytic osmylation of olefins (Behrens and Sharpless, *J. Org. Chem.*, (1985), 50, 5696), ring opening of epoxides (Wai et al., *J. Am. Chem. Soc.* (1989), 111, 1123), reduction or alkylation of a-hydroxy/alkoxy carbonyls (Davis et al., *J. Org. Chem.*, (1989), 54, 2021). Common to all of these approaches is the preexistence of the central carbon-carbon bond of the diol function. Methods that lead directly to a 1,2-diol via formation of this bond are less common and include the reaction of an a-alkoxy anion (Cohen and Lin, *J. Am. Chem. Soc.*, (1984), 106, 1130), with a carbonyl, and the reductive coupling of two carbonyls (i.e., pinacol coupling) (Pons and Santelli, *Tetrahedron*, (1988), 44, 4295).

Of all these methods, pinacol coupling is conceptually one of the simplest methods for the synthesis of 1,2-diols. Consequently, a number of methods have been developed which utilize this reaction for the preparation of these compounds. For example, McMurry et al., report the preparation of a 1,2-diol by pinacol coupling of a dialdehyde in the presence of TiCl$_3$(dimethoxyethane)$_2$Zn-Cu in dimethoxyethane (McMurry et al., *Tetrahedron Lett.*, (1988), 30, 1173). In a recent review article, Pons and Santelli describe many other methods leading to 1,2-diols which rely on low valent titanium complexes (Pons and Santelli, *Tetrahedron*, (1988), 44, 4295). Finally, Freudenberger et al., *J. Am. Chem. Soc.*, (1989), 111, 8014–8016 disclose a method which utilizes a vanadium (II) complex, [V$_2$C$_{13}$(THF)$_6$]$_2$[ZN$_2$Cl$_6$] to couple aldehydes.

While these methods are generally useful for the preparation of 1,2-diols, none of these teach how amino moieties can be incorporated into the diols. Furthermore, none of the methods disclosed in the prior art teach to make four stereocenters in a selective manner.

EP 402 646 discloses retroviral protease inhibiting compounds of the formula: A-X-B where A and B are independently substituted amino, substituted carbonyl, functionalized imino, functionalized alkyl, functionalized acyl, functionalized heterocyclic or functionalized (heterocyclic) alkyl and X is a linking group.

SUMMARY OF THE INVENTION

There is provided by this invention a compound of the formula:

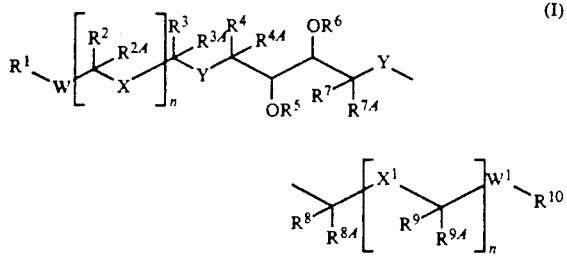

wherein:

R$^1$ through R$^4$ and R$^7$ through R$^{10}$ are independently selected from the following groups:

hydrogen;
C$_1$–C$_8$ alkyl substituted with 0–3 R$^{11}$;
C$_2$–C$_8$ alkenyl substituted with 0–3 R$^{11}$;
C$_3$–C$_8$ alkynyl substituted with 0–3 R$^{11}$;
C$_3$–C$_8$ cycloalkyl substituted with 0–3 R$^{11}$;
C$_6$–C$_{10}$ bicycloalkyl substituted with 0–3 R$^{11}$; aryl substituted with 0–3 R$^{12}$;
a C$_6$–C$_{14}$ carbocyclic residue substituted with 0–3 R$^{12}$;
a heterocyclic ring system substituted with 0–2 R$^{12}$, composed of 5 to 10 atoms including at least one nitrogen, oxygen or sulfur atom;

R$^{2A}$ through R$^{4A}$ and R$^{7A}$ through R$^{9A}$ are independently selected from the following groups:
hydrogen;
C$_1$–C$_4$ alkyl substituted with halogen or C$_1$–C$_2$ alkoxy;
benzyl substituted with halogen or C$_1$–C$_2$ alkoxy;

R$^5$ and R$^6$ are independently selected from the following groups:
hydrogen;
C$_1$–C$_6$ alkoxycarbonyl;
C$_1$–C$_6$ alkylcarbonyl;
benzoyl;
phenoxycarbonyl; or phenylaminocarbony; wherein said alkyl residues are substituted with 0–3 R$^{11}$, and said aryl residues are substituted with 0–3 R$^{12}$; or any other group that, when administered to a mammalian subject, cleaves to form the original diol in which R$^5$ and R$^6$ are hydrogen;

R$^{11}$ is selected from one or more of the following:
keto, halogen, cyano, —NR$^{13}$R$^{14}$, —CO$_2$R$^{13}$, —OC(=O)R$^{13}$, —OR$^{13}$, C$_2$–C$_6$ alkoxyalkyl, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$—, NR$^{14}$C(=O)OR$^{14}$, —OC(=O)NR$^{13}$R$^{14}$, —NR$^{13}$C(=O)NR$^{13}$R$^{14}$, NR$^{14}$SO$_2$NR$^{13}$R$^{14}$, —NR$^{14}$SO$_2$R$^{13}$, SO$_2$NR$^{13}$R$^{14}$, C$_1$–C$_4$ alkyl, C$_2$–C$_4$ alkenyl, C$_3$–C$_6$ cycloalkyl, C$_3$–C$_6$ cycloalkylmethyl;

a C$_5$–C$_{14}$ carbocyclic residue substituted with 0–3 R$^{12}$; aryl substituted with 0–3 R$^{12}$;
or a heterocyclic ring system substituted with 0–2 R$^{12}$, composed of 5 to 10 atoms including at least one nitrogen, oxygen or sulfur atom;

R$^{12}$, when a substituent on carbon, is selected from one or more of the following:

phenyl, benzyl, phenethyl, phenoxy, benzyloxy, halogen, hydroxy, nitro, cyano, C$_1$–C$_4$ alkyl, C$_3$–C$_6$ cycloalkyl, C$_3$–C$_6$ cycloalkylmethyl, C$_7$–C$_{10}$ arylalkyl, alkoxy, —NR$^{13}$R$^{14}$, C$_2$–C$_6$ alkoxyalkyl, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —S(O)$_m$R$^{13}$, —SO$_2$NR$^{13}$R$^{14}$, —NHSO$_2$R$^{14}$;

or R$^{12}$ may be a 3- or 4-carbon chain attached to adjacent carbons on the ring to form a fused 5- or 6-membered ring, said 5- or 6-membered ring being optionally substituted on the aliphatic carbons with halogen, C$_1$–C$_4$ alkyl, C$_1$–C$_4$ alkoxy, hydroxy, or NR$^{13}$R$^{14}$; or, when R$^{12}$ is attached to a saturated carbon atom it may be carbonyl or thiocarbonyl;

and R$^{12}$, when a substituent on nitrogen, is selected from one or more of the following:

phenyl, benzyl, phenethyl, hydroxy, C$_1$–C$_4$ hydroxyalkyl, C$_1$–C$_4$ alkoxy, , C$_1$–C$_4$ alkyl, C$_3$–C$_6$ cycloalkyl, C$_3$–C$_6$ cycloalkylmethyl, —NR$^{13}$R$^{14}$, C$_2$–C$_6$ alkoxyalkyl, C$_1$–C$_4$ haloalkyl, C$_1$–C$_4$ alkoxycarbonyl, C$_1$–C$_4$ alkylcarbonyloxy, C$_1$–C$_4$ alkylcarbonyl, R$^{13}$ is H, phenyl, benzyl or C$_1$–C$_6$ alkyl;
R$^{14}$ is H or C$_1$–C$_4$ alkyl;
or R$^{13}$R$^{14}$ can join to form (CH$_2$)$_4$, (CH$_2$)$_5$, (CH$_2$CH$_2$N(R$^{15}$)CH$_2$CH$_2$), or (CH$_2$CH$_2$OCH$_2$CH$_2$);
R$^{15}$ is H or CH$_3$;
m is 0, 1 or 2;
n and n$^1$ are independently 0 or 1;
W and W1 are independently selected from the following:
—NR$^{16}$C(=Q)NR$^{16}$—;
—C(=Q)NR$^{16}$—;
—C(=Q)O—;
—NR$^{16}$C(=Q)O—;
—OC(=Q)NR$^{16}$—;
—NR$^{16}$C(=Q)—;
—C(=Q)—;
—C(=Q)CH$_2$—;
—NR$^{16}$SO$_2$NR$^{16}$—
—NR$^{16}$SO$_2$—
—SO$_2$NR$^{16}$—
—SO$_2$—;
—QCH$_2$—;
—Q—;
—(CH$_2$)$_p$NR$^{16}$—;

—$CH_2CH_2$—;
—$CH=CH$—;
—$CH(OH)CH(OH)$—;
—$CH(OH)CH_2$—;
—$CH_2CH(OH)$—;
—$CH(OH)$—;
—$NH-NH$—;
—$C(=O)NH-NH$—;
—$C(Cl)=N$—;
—$C(-OR^{16})=N$—;
—$C(-NR^{16}R^{17})=N$—;
—$OP(=O)(Q^1R^{16})O$—;
—$P(=O)(Q^1R^{16})O$—;
—$SO_2NHC(=O)NH$—;

X and $X^1$ are independently selected from the following:
—$C(=Q)NR^{16}$—;
—$C(=Q)O$—;
—$C(=Q)$—;
—$CH_2C(=Q)$—;
—$CH_2C(=Q)CH_2$—;
—$C(=Q)CH_2$—;
—$SO_2NR^{16}$—
—$SO_2$—;
—$CH_2QCH_2$—;
—$CH_2Q$—;
—$CH_2NR^6$—;
—$CH_2CH_2$—;
—$CH=CH$—;
—$CH(OH)CH(OH)$—;
—$CH(OH)CH_2$—;
—$CH_2CH(OH)$—;
—$CH(OH)$—;
—$C(=O)NH-NH$—;
—$C(-OR^{16})=N$—;
—$C(-NR^{16}R^{17})=N$—;
—$C(L)=N$—;

Y and $Y^1$ are independently selected from the following:
—$C(=Q)NR^{16}$—;
—$(CH_2)_PC(=Q)NR^{16}$—;
—$SO_2NR^{16}$—;
—$CH_2NR^{16}$—;
—$C(L)=N$—; -
—$C(-OR^{16})=N$—;
—$C(-NR^{16}R^{17})=N$—;
—$NR^{12}C(=O)NR^{16}$—;
—$(CH_2)_pNR^{12}C(=O)NR^{16}$—;
—$OC(=O)NR^{16}$—;
—$(CH_2)_pOC(=O)NR^{16}$—;

$R^{16}$ is H, benzyl or $C_1$-$C_4$ alkyl;
$R^{17}$ is H or $C_1$-$C_4$ alkyl;
p is 1 or 2;
Q is selected from oxygen or sulfur;
$Q^1$ is selected from oxygen, sulfur, $NR^{14}$ or a direct bond;
and pharmaceutically acceptable salts and prodrugs thereof.

There is provided a process to prepare the compound of formula I comprising contacting an aldehyde of the formula:

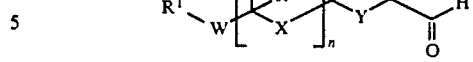

with an aldehyde of the formula:

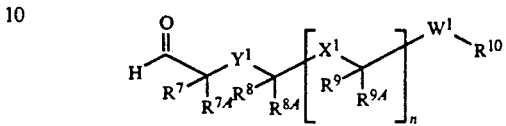

in the presence of Caulton's reagent to form the compound of Claim 1 wherein $R^5$ and $R^6$ are H and optionally contacting one or both of the alcohols with a derivatizing agent; wherein:

$R^1$ through $R^4$ and $R^7$ through $R^{10}$ are independently selected from the following groups:
hydrogen;
$C_1$-$C_8$ alkyl substituted with 0-3 $R^{11}$;
$C_2$-$C_8$ alkenyl substituted with 0-3 $R^{11}$;
$C_3$-$C_8$ alkynyl substituted with 0-3 $R^{11}$;
$C_3$-$C_8$ cycloalkyl substituted with 0-3 $R^{11}$;
$C_6$-$C_{10}$ bicycloalkyl substituted with 0-3 $R^{11}$;
aryl substituted with 0-3 $R^{12}$;
a $C_6$-$C_{14}$ carbocyclic residue substituted with 0-3 $R^{12}$;
a heterocyclic ring system substituted with 0-2 $R^{12}$, composed of 5 to 10 atoms including at least one nitrogen, oxygen or sulfur atom;

$R^{2A}$ through $R^{4A}$ and $R^{7A}$ through $R^{9A}$ are independently selected from the following groups:
hydrogen;
$C_1$-$C_4$ alkyl substituted with halogen or $C_1$-$C_2$ alkoxy;
benzyl substituted with halogen or $C_1$-$C_2$ alkoxy;

$R^5$ and $R^6$ are independently selected from the following groups:
hydrogen;
$C_1$-$C_6$ alkoxycarbonyl;
$C_1$-$C_6$ alkylcarbonyl;
benzoyl;
phenoxycarbonyl; or
phenylaminocarbony; wherein said alkyl residues are substituted with 0-3 $R^{11}$, and said aryl residues are substituted with 0-3 $R^{12}$; or any other group that, when administered to a mammalian subject, cleaves to form the original diol in which $R^5$ and $R^6$ are hydrogen;

$R^{11}$ is selected from one or more of the following:
keto, halogen, cyano, —$NR^{13}R^{14}$, —$CO_2R^{13}$, —$OC(=O)R^{13}$, —$OR^{13}$, $C_2$-$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$—, $NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$-$C_4$ alkyl, $C_2$-$C_4$ alkenyl, $C_3$-$C_6$ cycloalkyl, $C_3$-$C_6$ cycloalkylmethyl;
a $C_5$-$C_{14}$ carbocyclic residue substituted with 0-3 $R^{12}$;
aryl substituted with 0-3 $R^{12}$;
or a heterocyclic ring system substituted with 0-2 $R^{12}$, composed of 5 to 10 atoms including at least one nitrogen, oxygen or sulfur atom.

$R^{12}$, when a substituent on carbon, is selected from one or more of the following:
phenyl, benzyl, phenethyl, phenoxy, benzyloxy, halogen, hydroxy, nitro, cyano, $C_1$-$C_4$ alkyl, $C_3$-$C_6$ cycloalkyl, $C_3$-$C_6$ cycloalkylmethyl, $C_7$-$C_{10}$ arylalkyl, alkoxy, —NR$^{13}$R$^{14}$, C$_2$-C$_6$ alkoxyalkyl, C$_1$-C$_4$ hydroxyalkyl, methylenedioxy, ethylenedioxy, C$_1$-C$_4$ haloalkyl, C$_1$-C$_4$ haloalkoxy, C$_1$-C$_4$ alkoxycarbonyl, C$_1$-C$_4$ alkylcarbonyloxy, C$_1$-C$_4$ alkylcarbonyl, C$_1$-C$_4$ alkylcarbonylamino, —S(O)$_m$R$^{13}$, —SO$_2$NR$^{13}$R$^{14}$, —NHSO$_2$R$^{14}$;

or R$^{12}$ may be a 3- or 4- carbon chain attached to adjacent carbons on the ring to form a fused 5- or 6-membered ring, said 5- or 6- membered ring being optionally substituted on the aliphatic carbons with halogen, C$_1$-C$_4$ alkyl, C$_1$-C$_4$ alkoxy, hydroxy, or NR$^{13}$R$^{14}$; or, when R$^{12}$ is attached to a saturated carbon atom it may be carbonyl or thiocarbonyl;

and R$^{12}$, when a substituent on nitrogen, is selected from one or more of the following:

phenyl, benzyl, phenethyl, hydroxy, C$_1$-C$_4$ hydroxyalkyl, C$_1$-C$_4$ alkoxy, , C$_1$-C$_4$ alkyl, C$_3$-C$_6$ cycloalkyl, C$_3$-C$_6$ cycloalkylmethyl, —NR$^{13}$R$^{14}$, C$_2$-C$_6$ alkoxyalkyl, C$_1$-C$_4$ haloalkyl, C$_1$-C$_4$ alkoxycarbonyl, C$_1$-C$_4$ alkylcarbonyloxy, C$_1$-C$_4$ alkylcarbonyl, R$^{13}$ is H, phenyl, benzyl or C$_1$-C$_6$ alkyl;

R$^{14}$ is H or C$_1$-C$_4$ alkyl;

or R$^{13}$R$^{14}$ can join to form (CH$_2$)$_4$, (CH$_2$)$_5$, (CH$_2$CH$_2$N(R$^{15}$)CH$_2$CH$_2$), or (CH$_2$CH$_2$OCH$_2$CH$_2$);

R$^{15}$ is H or CH$_3$;

m is 0, 1 or 2;

n and n$^1$ are independently 0 or 1;

W and W$^1$ are independently selected from the following:

—NR$^{16}$C(=Q)NR$^{16}$—;
—C(=Q)NR$^{16}$—;
—C(=Q)O—;
—NR$^{16}$C(=Q)O—;
—OC(=Q)NR$^{16}$—;
—NR$^{16}$C(=Q)—;
—C(=Q)—;
—C(=Q)CH$_2$—;
—NR$^{16}$SO$_2$NR$^{16}$—
—NR$^{16}$SO$_2$—
—SO$_2$NR$^{16}$—
—SO$_2$—;
—QCH$_2$—;
—Q—;
—(CH$_2$)$_p$NR$^{16}$—;
—CH$_2$CH$_2$—;
—CH=CH—;
—CH(OH)CH(OH)—;
—CH(OH)CH$_2$—;
—CH$_2$CH(OH)—;
—CH(OH)—;
—NH—NH—;
—C(=O)NH—NH—;
—C(Cl)=N—;
—C(—OR$^{16}$)=N—;
—C(—NR$^{16}$R$^{17}$)=N—;
—OP(=O)(Q$^1$R$^{16}$)O—;
—P(=O)(Q$^1$R$^{16}$)O—;
—SO$_2$NHC(=O)NH—;

X and X$^1$ are independently selected from the following:

—C(=Q)NR$^{16}$—;
—C(=Q)O—;
—C(=Q)—;
—CH$_2$C(=Q)—;
—CH$_2$C(=Q)CH$_2$—;
—C(=Q)CH$_2$—;
—SO$_2$NR$^{16}$—
—SO$_2$—;

—CH$_2$QCH$_2$—;
—CH$_2$Q—;
—CH$_2$NR$^{16}$—;
—CH$_2$CH$_2$—;
—CH=CH—;
—CH(OH)CH(OH)—;
—CH(OH)CH$_2$—;
—CH$_2$CH(OH)—;
—CH(OH)—;
—C(=O)NH—NH—;
—C(—OR$^{16}$)=N—;
—C(—NR$^{16}$R$^{16}$)=N—;
—C(L)=N—.

Y and Y$^1$ are independently selected from the following:

—C(=Q)NR$^{16}$—;
—(CH$_2$)$_p$C(=Q)NR$^{16}$—;
—SO$_2$NR$^{16}$—;
—CH$_2$NR$^{16}$—;
—C(L)=N—;
—C(—OR$^{16}$)=N—;
—C(—NR$^{16}$R$^{16}$)=N—;
—NR$^{12}$C(=O)NR$^{16}$—;
—(CH$_2$)$_p$NR$^{12}$C(=O)NR$^{16}$—;
—OC(=O)NR$^{16}$—;
—(CH$_2$)$_p$OC(=O)NR$^{16}$—;

R$^{16}$ is H, benzyl or C$_1$-C$_4$ alkyl;

R$^{17}$ is H or C$_1$-C$_4$ alkyl;

p is 1 or 2;

Q is selected from oxygen or sulfur;

L is Cl or Br;

Q$^1$ is selected from oxygen, sulfur, NR$^{14}$ or a direct bond;

and pharmaceutically acceptable salts and prodrugs thereof. Suitable derivatizing agents include, but are not limited to, acyl chlorides or anhydrides, diphenyl carbonates, and isocyanates using techniques well known to those skilled in the art.

A process for preparing an intermediate compound of the formula:

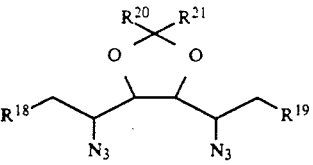
(III)

comprising:

(a) reacting an organometallic derivative R$^{18}$M or R$^{19}$M in the presence of copper (I) salts and an ether-containing, aprotic solvent system with a diepoxide of the formula:

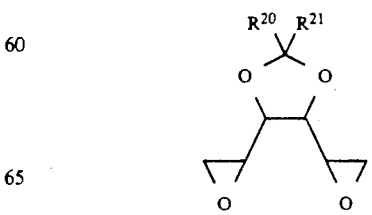
(IV)

(b) reacting the product of step (a) of the formula:

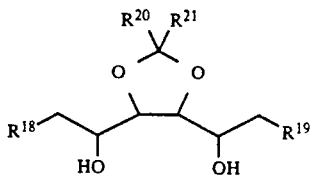

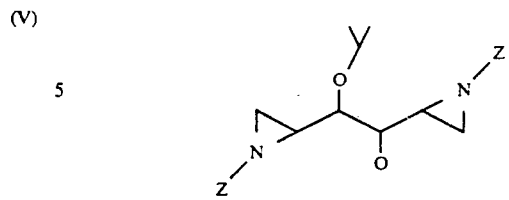

with $R^{22}R^{23}R^{24}P$ and $C_1$-$C_6$ dialkyl azodicarboxylate in the presence of an azide anion and an aprotic organic solvent generally at a temperature between $-20°$ to $100°$ C.; wherein:

$R^{18}$ and $R^{19}$ are independently $C_2$-$C_8$ alkyl, $C_3$-$C_8$ cycloalkyl substituted with 0-3 $R^{25}$, a $C_6$-$C_{10}$ carbocyclic aromatic residue, for example phenyl or naphthyl, substituted with 0-3 $R^{26}$;

a heterocyclic ring system substituted with 0-2 $R^{26}$, composed of 5 to 10 atoms including at least one nitrogen, oxygen or sulfur atom; for example, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, pyrrolidinyl, pyrrolinyl, tetrahydrofuranyl, tetrahydroquinolinyl, tetrahydroisoquinolinyl, decahydroquinolinyl or octahydroisoquinolinyl;

$R^{25}$ is selected from one or more of the following groups: keto, halogen, $R^{27}R^{28}N$, $CO_2R^{27}$, $OCO_2R^{27}$, $OR^{27}$, $S(O)_nR^{27}$, $NHC(=NH)NHR^{27}$, $C(=NH)NHR^{27}$, $C(=O)NHR^{27}$, or cyano; $C_3$-$C_8$ cycloalkyl substituted with 0-3 $R^{25}$, a $C_6$-$C_{10}$ carbocyclic aromatic residue, for example phenyl or naphthyl, substituted with 0-3 $R^{26}$;

a heterocyclic ring system substituted with 0-2 $R^{26}$, composed of 5 to 10 atoms including at least one nitrogen, oxygen or sulfur atom; for example, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, pyrrolidinyl, pyrrolinyl, tetrahydrofuranyl, tetrahydroquinolinyl, tetrahydroisoquinolinyl, decahydroquinolinyl or octahydroisoquinolinyl;

$R^{26}$ is selected from one or more of the following groups: phenyl, phenoxy, benzyloxy, halogen, hydroxy, nitro, cyano, $C_1$-$C_4$ alkyl, $C_1$-$C_4$ alkoxy, $C_2$-$C_6$ alkoxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, alkylsulfonyl, $SO_2NR^{27}R^{28}$, and $R^{27}SO_2NH$;

$R^{20}$ and $R^{21}$ are independently H, $C_1$-$C_8$ alkyl, a $C_6$-$C_{10}$ carbocyclic aromatic residue, for example phenyl or naphthyl, substituted with 0-3 $R^{26}$, or $C_1$-$C_3$ alkyl substituted with a $C_6$-$C_{10}$ carbocyclic aromatic residue, for example phenyl or naphthyl, substituted with 0-3 $R^{26}$;

M is lithium or magnesium;

$R^{22}$, $R^{23}$ and $R^{24}$ are independently phenyl or $C_1$-$C_6$ alkyl.

Also provided by this invention are the intermediates of Formula III, IV, and V.

A process for the preparation of saturated 3-7 membered nitrogen containing heterocycles, comprising, carrying out an intramolecular Mitsunobo reaction on a precursor molecule containing a protected nitrogen atom and a hydroxyl group separated by 2-6 atoms.

A process for preparing an intermediate compound of the formula:

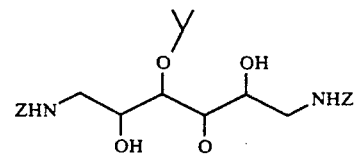

comprising, carrying out an intermediate Mitsunobu reaction on a compound of the formula:

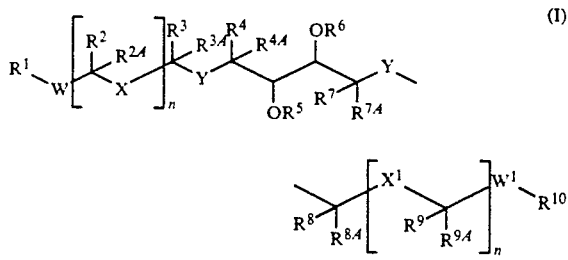

wherein: Z is $COOCH_2Ph$. A process for preparing a compound of formula:

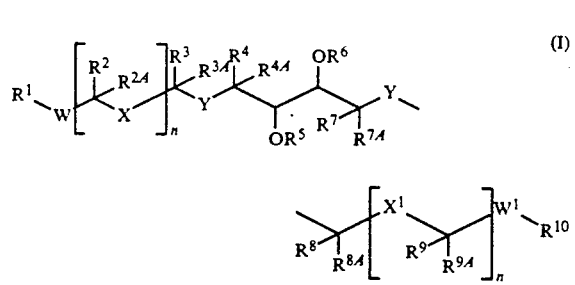

comprising:

(a) preparation of the required catalyst by mixing $VCl_3$ $(THF)_3$ with freshly prepared zinc-copper couple under strictly anhydrous, deoxygenated conditions in an, aprotic solvent at room temperature; and (b) reacting the product of step (a) with an aldehyde of formula (1) in an aprotic solvent at $-78°$ C. $100°$ C. where the ratio of zinc-copper couple: $VCl_3$ $(THF)_3$: aldehyde is 1-3:1-3:1.

There are provided methods for treatment of viral infections which comprises administering to a host in need of such treatment a pharmaceutically effective antiviral amount of the compound of the following formula:

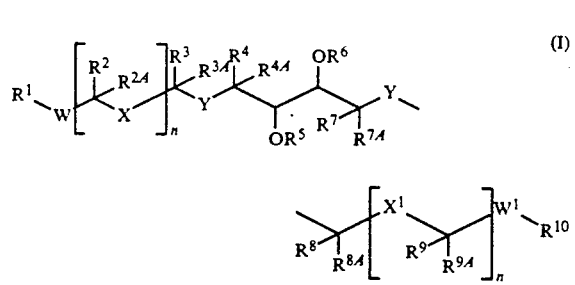

wherein:

$R^1$ through $R^4$ and $R^7$ through $R^{10}$ are independently selected from the following groups:
hydrogen;
$C_1$-$C_8$ alkyl substituted with 0-3 $R^{11}$;
$C_2$-$C_8$ alkenyl substituted with 0-3 $R^{11}$;
$C_3$-$C_8$ alkynyl substituted with 0-3 $R^{11}$;

$C_3$-$C_8$ cycloalkyl substituted with 0-3 $R^{11}$;
$C_6$-$C_{10}$ bicycloalkyl substituted with 0-3 $R^{11}$;
aryl substituted with 0-3 $R^{12}$;
a $C_6$-$C_{14}$ carbocyclic residue substituted with 0-3 $R^{12}$;
a heterocyclic ring system substituted with 0-2 $R^{12}$, composed of 5 to 10 atoms including at least one nitrogen, oxygen or sulfur atom;
$R^{2A}$ through $R^{4A}$ and $R^{7A}$ through $R^{9A}$ are independently selected from the following groups: hydrogen; $C_1$-$C_4$ alkyl substituted with halogen or $C_1$-$C_2$ alkoxy;
benzyl substituted with halogen or $C_1$-$C_2$ alkoxy;
$R^5$ and $R^6$ are independently selected from the following groups:
hydrogen;
$C_1$-$C_6$ alkoxycarbonyl;
$C_1$-$C_6$ alkylcarbonyl;
benzoyl;
phenoxycarbonyl; or
phenylaminocarbony; wherein said alkyl residues are substituted with 0-3 $R^{11}$, and said aryl residues are substituted with 0-3 $R^{12}$; or any other group that, when administered to a mammalian subject, cleaves to form the original diol in which $R^5$ and $R^6$ are hydrogen;
$R^{11}$ is selected from one or more of the following:
keto, halogen, cyano, —$NR^{13}R^{14}$, —$CO_2R^{13}$, —$OC(=O)R^{13}$, —$OR^{13}$, $C_2$-$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$—, $NR^{14}C(=O)OR^{14}$, —$OC(=O)NR^{13}R^{14}$, —$NR^{13}C(=O)NR^{13}R^{14}$, $NR^{14}SO_2NR^{13}R^{14}$, —$NR^{14}SO_2R^{13}$, —$SO_2NR^{13}R^{14}$, $C_1$-$C_4$ alkyl, $C_2$-$C_4$ alkenyl, $C_3$-$C_6$ cycloalkyl, $C_3$-$C_6$ cycloalkylmethyl;
a $C_5$-$C_{14}$ carbocyclic residue substituted with 0-3 $R^{12}$;
aryl substituted with 0-3 $R^{12}$;
or a heterocyclic ring system substituted with 0-2 $R^{12}$, composed of 5 to 10 atoms including at least one nitrogen, oxygen or sulfur atom;
$R^{12}$, when a substituent on carbon, is selected from one or more of the following:
phenyl, benzyl, phenethyl, phenoxy, benzyloxy, halogen, hydroxy, nitro, cyano, $C_1$-$C_4$ alkyl, $C_3$-$C_6$ cycloalkyl, $C_3$-$C_6$ cycloalkylmethyl, $C_7$-$C_{10}$ arylalkyl, alkoxy, —$NR^{13}R^{14}$, $C_2$-$C_6$ alkoxyalkyl, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —$S(O)_mR^{13}$, —$SO_2NR^{13}R^{14}$, —$NHSO_2R^{14}$;
or $R^{12}$ may be a 3- or 4- carbon chain attached to adjacent carbons on the ring to form a fused 5- or 6-membered ring, said 5- or 6-membered ring being optionally substituted on the aliphatic carbons with halogen, $C_1$-$C_4$ alkyl, $C_1$-$C_4$ alkoxy, hydroxy, or $NR^{13}R^{14}$; or, when $R^{12}$ is attached to a saturated carbon atom it may be carbonyl or thiocarbonyl;
and $R^{12}$, when a subsistent on nitrogen, is selected from one or more of the following:
phenyl, benzyl, phenethyl, hydroxy, $C_1$-$C_4$ hydroxyalkyl, $C_1$-$C_4$ alkoxy, , $C_1$-$C_4$ alkyl, $C_3$-$C_6$ cycloalkyl, $C_3$-$C_6$ cycloalkylmethyl, —$NR^{13}R^{14}$, $C_2$-$C_6$ alkoxyalkyl, $C_1$-$C_4$ haloalkyl, $C_1$-$C_4$ alkoxycarbonyl, $C_1$-$C_4$ alkylcarbonyloxy, $C_1$-$C_4$ alkylcarbonyl;
$R^{13}$ is H, phenyl, benzyl or $C_1$-$C_6$ alkyl;
$R^{14}$ is H or $C_1$-$C_4$ alkyl;
or $R^{13}R^{14}$ can join to form $(CH_2)_4$, $(CH_2)_5$, $(CH_2CH_2N(R^{15})CH_2CH_2)$, or $(CH_2CH_2OCH_2CH_2)$;
$R^{15}$ is H or $CH_3$;
m is 0, 1 or 2;

n and $n^1$ are independently 0 or 1;
W and $W^1$ are independently selected from the following:
—$NR^{16}C(=Q)NR^{16}$—;
—$C(=Q)NR^{16}$—;
—$C(=Q)O$—;
—$NR^{16}C(=Q)O$—;
—$OC(=Q)NR^{16}$—;
—$NR^{16}C(=Q)$—;
—$C(=Q)$—;
—$C(=Q)CH_2$—;
—$NR^{16}SO_2NR^{16}$—
—$NR^{16}SO_2$—
—$SO_2NR^{16}$—
—$SO_2$—;
—$QCH_2$—;
—$Q$—;
—$(CH_2)_pNR^{16}$—;
—$CH_2CH_2$—;
—$CH=CH$—;
—$CH(OH)CH(OH)$—;
—$CH(OH)CH_2$—;
—$CH_2CH(OH)$—;
—$CH(OH)$—;
—$NH$—$NH$—;
—$C(=O)NH$—$NH$—;
—$C(Cl)=N$—;
—$C(-OR^{16})=N$—;
—$C(-NR^{16}R^{17})=N$—;
—$OP(=O)(Q^1R^{16})O$—;
—$P(=O)(Q^1R^{16})O$—;
—$SO_2NHC(=O)NH$—;
X and $X^1$ are independently selected from the following:
—$C(=Q)NR^{16}$—;
—$C(=Q)O$—;
—$C(=Q)$—;
—$CH_2C(=Q)$—;
—$CH_2C(=Q)CH_2$—;
—$C(=Q)CH_2$—;
—$SO_2NR^{16}$—
—$SO_2$—;
—$CH_2QCH_2$—;
—$CH_2Q$—;
—$CH_2NR^{16}$—;
—$CH_2CH_2$—;
—$CH=CH$—;
—$CH(OH)CH(OH)$—;
—$CH(OH)CH_2$—;
—$CH_2CH(OH)$—;
—$CH(OH)$—;
—$C(=O)NH$—$NH$—;
—$C(-OR^{16})=N$—;
—$C(-NR^{16}R^{17})=N$—;
—$C(L)=N$—;
Y and $Y^1$ are independently selected from the following:
—$C(=Q)NR^{16}$—;
—$(CH_2)PC(=Q)NR^{16}$—;
—$SO_2NR^{16}$—;
—$CH_2NR^{16}$—;
—$C(L)=N$—;
—$C(-OR^{16})=N$—;
—$C(-NR^{16}R^{17})=N$—;
—$NR^{12}C(=O)NR^{16}$—;
—$(CH_2)_pNR^{12}C(=O)NR^{16}$—;
—$OC(=O)NR^{16}$—;
—$(CH_2)_pOC(=O)NR^{16}$—;

$R^{16}$ is H, benzyl or $C_1-C_4$ alkyl;
$R^{17}$ is H or $C_1-C_4$ alkyl;
p is 1 or 2;
Q is selected from oxygen or sulfur;
L is Cl or Br;
$Q^1$ is selected from oxygen, sulfur, $NR^{14}$ or a direct bond; and pharmaceutically acceptable salts and prodrugs thereof.

PREFERRED EMBODIMENTS

Compounds preferred for use in the method of this invention include the following:

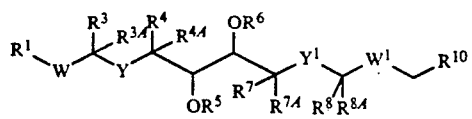

$R^1$ and $R^{10}$ are independently selected from the following:
hydrogen;
$C_1-C_6$ alkyl substituted with 0–2 $R^{11}$;
$C_3-C_6$ cycloalkyl substituted with 0–2 $R^{11}$;
$C_6-C_{10}$ bicycloalkyl substituted with 0–2 $R^{11}$;
aryl substituted with 0–3 $R^{12}$;
a $C_6-C_{14}$ carbocyclic residue substituted with 0–2 $R^{12}$;
a heterocyclic ring system substituted with 0–2 $R^{12}$, composed of 5 to 10 atoms including at least one nitrogen, oxygen or sulfur atom;
$R^3$ and $R^8$ are independently selected from the following groups:
hydrogen;
$C_1-C_5$ alkyl substituted with 0–2 $R^{11}$;
$C_2-C_4$ alkenyl substituted with 0–2 $R^{11}$;
$C_3-C_6$ cycloalkyl substituted with 0–2 $R^{11}$;
with the proviso that the total number of non-hydrogen atoms comprising $R^3$ is less than or equal to 6, and the total number of non-hydrogen atoms comprising $R^8$ is less than or equal to 6;
$R^4$ and $R^7$ are independently selected from the following groups:
hydrogen;
$C_1-C_4$ alkyl substituted with 0–3 $R^{11}$;
$C_2-C_3$ alkenyl substituted with 0–3 $R^{11}$;
$R^{3A}$, $R^{4A}$, $R^{7A}$ and $R^{8A}$ are independently selected from the following groups:
hydrogen;
$C_1-C_2$ alkyl;
$R^4$ and $R^6$ are independently selected from the following groups:
hydrogen, or any other group that, when administered to a mammalian subject, cleaves to form the original diol in which $R^5$ and $R^6$ are hydrogen;
$R^{11}$ is selected from one or more of the following:
keto, halogen, cyano, $-NR^{13}R^{14}$, $-CO_2R^{13}$, $-OC(=O)R^{13}$, $-OR^{13}$, $C_2-C_6$ alkoxyalkyl, $-S(O)_mR^{13}$, $-NHC(=NH)NHR^{13}$, $-C(=NH)NHR^{13}$, $-C(=O)NR^{13}R^{14}$, $-NR^{14}C(=O)R^{13}-$, $NR^{14}C(=O)OR^{14}$, $-OC(=O)NR^{13}R^{14}$, $NR^{13}C(=O)NR^{13}R^{14}$, $-NR^{14}SO_2NR^{13}R^{14}$, $-NR^{14}SO_2R^{13}$, $-SO_2NR^{13}R^{14}$, $C_1-C_4$ alkyl, $C_2-C_4$ alkenyl, $C_3-C_6$ cycloalkyl, $C_3-C_6$ cycloalkylmethyl;
a $C_5-C_{14}$ carbocyclic residue substituted with 0–3 $R^{12}$;
aryl substituted with 0–3 $R^{12}$;
or a heterocyclic ring system substituted with 0–2 $R^{12}$, composed of 5 to 10 atoms including at least one nitrogen, oxygen or sulfur atom;

$R^{12}$, when a substituent on carbon, is selected from one or more of the following:
phenyl, benzyl, phenethyl, phenoxy, benzyloxy, halogen, hydroxy, nitro, cyano, $C_1-C_4$ alkyl, $C_3-C_6$ cycloalkyl, $C_3-C_6$ cycloalkylmethyl, $C_7-C_{10}$ arylalkyl, alkoxy, $-NR^{13}R^{14}$, $C_2-C_6$ alkoxyalkyl, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1C_4$ alkylcarbonyloxy, $C_1-C_4$ alkylcarbonyl, $C_1-C_4$ alkylcarbonylamino, $-S(O)_mR^{13}$, $-SO_2NR^{13}R^{14}$, $-NHSO_2R^{14}$;
or $R^{12}$ may be a 3- or 4-carbon chain attached to adjacent carbons on the ring to form a fused 5- or 6-membered ring, said 5- or 6-membered ring being optionally substituted on the aliphatic carbons with halogen, $C_1-C_4$ alkyl, $C_1-C_4$ alkoxy, hydroxy, or $NR^{13}R^{14}$; or, when $R^{12}$ is attached to a saturated carbon atom it may be carbonyl or thiocarbonyl; and
$R^{12}$, when a substituent on nitrogen, is selected from one or more of the following:
benzyl, hydroxy, $C_1-C_4$ alkoxy, $C_1-C_5$ hydroxyalkyl, $C_1-C_4$ alkyl, $C_3-C_6$ cycloalkyl, $C_3-C_6$ cycloalkylmethyl, $C_1-C_4$ alkoxycarbonyl, $C_1-C_4$ alkylcarbonyloxy, $C_1-C_4$ alkylcarbonyl,
$R^{13}$ is H, benzyl or $C_1-C_4$ alkyl;
$R^{14}$ is H or $C_1-C_4$ alkyl;
or $R^{13}R^{14}$ can join to form $(CH_2)_4$, $(CH_2)_5$, $(CH_2CH_2N(R^{15})CH_2CH_2)$, or $(CH_2CH_2OCH_2CH_2)$;
$R^{15}$ is H or $CH_3$;
m is 0, 1 or 2;
W and W1 are independently selected from the following:
$-NR^{16}C(=Q)NR^{16}-$;
$-C(=Q)NR^{16}-$;
$-OC(=Q)NR^{16}-$;
$-NR^{16}SO_2NR^{16}-$
$-SO_2NR^{16}-$
$-(CH_2)_pNR^{16}-$;
$-P(=O)(Q^1R^{16})O-$;
$-SO_2NHC(=O)NH-$;
Y and $Y^1$ are independently selected from the following:
$-C(=Q)NR^{16}-$;
$-NR^{12}C(=O)NR^{16}-$;
$-OC(=O)NR^{16}-$; or
$-(CH_2)_pNR^{13}-$;
$R^{16}$ is H or $C_1-C_2$ alkyl;
$R^{17}$ is H or $C_1-C_2$ alkyl;
p is 1 or 2;
Q is selected from oxygen or sulfur;
$Q^1$ is selected from oxygen, sulfur, $NR^{14}$ or a direct bond;
and pharmaceutically acceptable salts and prodrugs thereof.

More preferred for greater activity and/or ease of synthesis is a compound of Formula I, wherein:

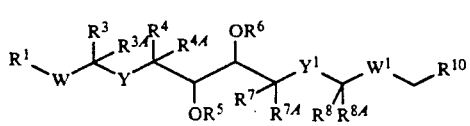

$R^1$ and $R^{10}$ are independently selected from the following:
hydrogen;
$C_1-C_6$ alkyl substituted with 0–1 $R^{18}$;
$C_2-C_4$ alkenyl substituted with 0–1 $R^{18}$;

aryl substituted with 0-1 $R^{19}$;

a heterocyclic ring system, substituted with 0-1 $R^{19}$, selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, pyrrolidinyl,tetrahydrofuranyl, tetrahydroquinolinyl, tetrahydroisoquinolinyl, or decahydroisoquinolinyl;

wherein $R^{18}$ is chosen from the following group:

keto, halogen, cyano, $-NR^{13}R^{14}$, $-C_{O2}R^{13}$, $-OC(=O)R^{13}$, $-OR^{13}$, $C_2-C_6$ alkoxyalkyl, $-S(O)_mR^{13}$, $-NHC(=NH)NHR^{13}$, $-C(=O)NR^{13}R^{14}$, $-NR^{14}C(=O)R^{13}-$, $NR^{14}C(=O)OR^{14}$, $-OC(=O)NR^{13}R^{14}$, $NR^{13}C(=O)NR^{13}R^{14}$, $-NR^{14}so2NR^{13}R^{14}$, $-NR^{14}SO_2R^{13}$, $-SO_2NR^{13}R^{14}$, $C_1-C_4$ alkyl, $C_2-C_4$ alkenyl, or $C_3-C_6$ cycloalkyl;

a $C_5-C_{14}$ carbocyclic residue substituted with 0-3 $R^{19}$;

aryl substituted with 0-2 $R^{19}$;

or a heterocyclic ring system substituted with 0-2 $R^{19}$, selected from selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, pyrrolidinyl,tetrahydrofuranyl, tetrahydroquinolinyl, tetrahydroisoquinolinyl, or decahydroisoquinolinyl;

wherein $R^{19}$, when a substituent on carbon, is selected from the following:

halogen, hydroxy, nitro, cyano, methyl, methoxy, $-NR^{13}R^{14}$, $C_1-C_4$ haloalkyl, $C_1-C_2$ alkoxycarbonyl, $C_1-C_2$ alkylcarbonyloxy, $C_1-C_2$ alkylcarbonylamino, $SO_2NR^{13}R^{14}$, or $-NHSO_2R^{14}$;

and $R^{19}$, when a substituent on nitrogen, is $C_1-C_4$ alkyl;

$R^3$ and $R^8$ are independently selected from the following groups:

hydrogen;

$C_1-C_5$ alkyl substituted with 0-3 halogen or 0-1 $R^{20}$;

$C_2-C_4$ alkenyl substituted with 0-3 halogen or 0-1 $R^{20}$;

$C_3-C_6-$ cycloalkyl substituted with 0-3 halogen or 0-1 $R^{20}$;

wherein $R^{20}$ is selected from the following groups:

keto, amino, methylamino, dimethylamino, $-C(=O)NH_2$, $C(=O)NMe_2$, $C(=O)NHMe$, or $C_3-C_5$ cycloalkyl;

with the proviso that the total number of non-hydrogen atoms comprising $R^3$ is less than or equal to 6, and the total number of non-hydrogen atoms comprising $R^8$ is less than or equal to 6;

$R^4$ and $R^7$ are independently selected from the following groups:

$C_1-C_4$ alkyl substituted with 0-3 halogen or 0-1 $R^{21}$, wherein $R^{21}$ is selected from the following groups:

keto, halogen, cyano, $-NR^{13}R^{14}$, $-CO_2R^{13}$, $-OC(=O)R^{13}$, $-OR^{13}$, $C_2-C_4$ alkoxyalkyl, $-S(O)_mR^{13}$, $-C_3-C_6$ cycloalkyl;

a $C_5-C_{10}$ carbocyclic residue substituted with 0-1 $R^{22}$;

aryl substituted with 0-1 $R^{22}$;

or a heterocyclic ring system, substituted with 0-1 $R^{22}$, selected from pyridyl, thienyl, indolyl, piperazyl, N-methylpiperazyl, or imidazolyl;

wherein $R^{22}$ is selected from one or more of the following groups:

benzyl, benzyloxy, halogen, hydroxy, nitro, $C_1-C_4$ alkyl, $C_1-C_4$ alkoxy, amino, methylamino, dimethylamino, haloalkyl, haloalkoxy, $-C(=O)_2R^{14}$, or $-OC(O_2)R^{14}$;

$R^{34}$, $R^{44}$, $R^{74}$ and $R^{84}$ are hydrogen;

$R^5$ and $R^6$ are independently selected from the following groups: hydrogen, or any other group that, when administered to a mammalian subject, cleaves to form the original diol in which $R^5$ and $R^6$ are hydrogen;

$R^{13}$ and $R^{14}$ are independently selected from H or $C_1-C_2$ alkyl;

m is 0, 1 or 2;

n and $n^1$ are 0;

W and W1 are independently selected from the following:

$-NR^{16}C(=Q)NR^{16}-$;

$-C(=O)NR^{16}-$;

$-OC(=O)NR^{16}-$;

$-(CH_2)_pNR^{16}-$;

Y and $Y^1$ are independently selected from the following:

$-C(=O)NR^{16}-$;

$-NR^{12}C(=O)NR^{16}-$;

$-OC(=O)NR^{16}-$; or $-(CH_2)_pNR^{16}-$;

$R^{16}$ is H or methyl;

p is 1 or 2;

Q is selected from oxygen or sulfur; and pharmaceutically acceptable salts and prodrugs thereof.

Specific examples of compounds useful in various embodiments of the invention include compounds of the formula:

a) (S,R,R,S)—N-[4-[[(1,1-dimethylethoxy)carbonyl]amino]-2,3-dihydroxy-5-(1H -pyrrol-1-yl)-1-[(1H -pyrrol-1-yl)methyl]pentyl]-$N_2$-formyl-L-valinamide b) (S,R,R,S)—N-[4-[[(1,1-dimethylethoxy)carbonyl]amino]-2,3-dihydroxy-5-phenyl-1-(phenylmethyl)pentyl]-$N_2$-[[N-[(1H -benzimidazol-2-yl)methyl]-N-methylamino]carbonyl]-L-valinamide c) (S,R,R,S)-N-[4-[[(1,1-dimethylethoxy)carbonyl]amino]-2,3-dihydroxy-5-(4-pyridinyl)-1-(4-pyridinylmethyl)pentyl]-$N_2$-formyl-L-valinamide d) [S,R,R,S(2S*,3S*)]-(1,1-dimethylethyl) [2,3-dihydroxy-4-[(3-hydroxy-4-methoxy-2-(1-methylethyl)-1-oxobutyl]amino]-5-(4-pyridinyl)-1-(4-pyridinylmethyl)-pentyl]carbamate e) (S,R,R,S)-N-[4-[[(1,1-dimethylethoxy)carbonyl]amino]-2,3-dihydroxy5-(4-pyridinyl)-1-(4-pyridinylmethyl)pentyl]-$N_2$-[(phenylmethoxy)carbonyl]-L-valinamide f) (S,R,R,S)-$N_2$-[[1(dimethylamino)cyclopropyl]carbonyl]-N-[4-[[(1,1-dimethyl-ethoxy)carbonyl]amino]-2,3-dihydroxy-5-phenyl-1-(phenylmethyl)pentyl]-N-L-valinamide g) (S,R,R,S)-N-[4-[[(1,1-dimethylethoxy)carbonyl]amino]-2,3-dihydroxy1-(phenylmethyl)hexyl]-$N_2$-(N-methyl-L-alanyl)-L-valinamide h) (S,R,R,S)-(1,1-dimethylethyl) [4-[[[2-[(dimethylamino)methyl]-1H -imidazol-5-yl]carbonyl]amino]-2,3-dihydroxy-5-phenyl-1-(phenylmethyl)-pentyl]carbamate i) (S,R,R,S)-$N_2$-[[[2-[(dimethylamino)carbonyl]-phenyl]methoxy]carbon yl]-N-[4-[[(1,1-dimethylethoxy)carbonyl]amino]-2,3-dihydroxy-5-phenyl-1-(phenylmethyl)pentyl]-L-valinamide j) (S,R,R,S)-N,N'-[2,3-dihydroxy-1,4-bis(phenylmethyl)-1,4-butanediyl]bis[$N_2$-(4-aminobenzoyl)-L-valinamide]

k) (S,R,R,S)-$N_2$-[[[4-(dimethylamino)phenyl]methoxy]carbonyl]-N-[4-[[(1,1-dimethylethoxy)carbonyl- ]amino]-2,3-dihydroxy-5-phenyl-1-(phenylmethyl)pentyl]-L-valinamide l) (S,R,R,S)-N$_2$-[[[4-[(dimethylamino)methyl]-phenyl]methoxy]carbonyl]-N-[4-[[(1,1-dimethylethoxy)carbonyl]amino]-2,3-dihydroxy-5-phenyl-1-(phenylmethyl)pentyl]-L-valinamide.

The compounds herein described may have asymmetric centers. All chiral, diastereomeric and racemic forms are included in the present invention. Many geometric isomers of olefins, C=N double bonds, and the like can also be present in the compounds described herein, and all such stable isomers are contemplated in the present invention.

When any variable (for example, $R^1$ through $R^{17}$, $R^{24}$ through $R^{94}$, m, n, p, Q, W, X, Y, Z, etc.) occurs more than one time in any constituent or in formula (I), its definition on each occurrence is independent of its definition at every other occurrence. Also, combinations of substituents and/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "biycloalkyl" is intended to include saturated bicyclic ring groups such as [3.3.0]bicyclooctane, [4.3.0] bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like. "Halo" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; "carbocyclic" is intended to mean any stable 5- to 7-membered monocyclic or bicyclic or 7- to 14-membered bicyclic or tricyclic carbon ring, any of which may be saturated, partially unsaturated, or aromatic.

As used herein, the term heterocycle is intended to mean a stable 5- to 7-membered monocyclic or bicyclic or 7- to 10-membered bicyclic heterocyclic ring which is either saturated or unsaturated, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl. The term "substituted", as used herein, means that an one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive: isolation to a useful degree of purity from a reaction mixture, and formulation into an efficacious therapeutic agent.

DETAILED DESCRIPTION OF THE INVENTION

Synthesis

Compounds of formula (I) are synthesized according to the procedures discussed below. In addition to disclosing known methods for the preparation of these compounds, the present invention provides several novel processes for their synthesis. The first of these is an improved process for the preparation of compounds of formula (I) via the reductive coupling of aldehydes. A second is the stereoselective synthesis of compounds of formula (I) via a modified coupling method. A third is the stereospecific synthesis of compounds of formula (I) from mannitol. The present invention also provides novel processes for the preparation of key intermediates used in the mannitol route.

Reductive Coupling of Aldehydes

A preferred method for the preparation of compounds of formula (I) is the reductive coupling of aldehydes. This method utilizes a catalyst which contains vanadium(II); however, other low valent metals (such as titanium and samarium) and pinacol reagents (such as magnesium) can also be used with advantage. It is based on a process disclosed by Pederson et al. for the preparation of diols. Freudenberger, J. H.; Konradi, A. W.; Pedersen, S. F., *J. Am. Chem. Soc.* 1989, 111, 8014; and Konradi, A. W.; Pedersen, S. F., *J. Org. Chem.* 1990, 55, 4506. The preferred catalyst is Caulton's Reagent, [V$_2$Cl$_3$(THF)$_6$]$_2$[ZN$_2$Cl$_6$]. Preparation of this reagent has been disclosed. Bouma et al. *Inorg. Chem.*, 23, 2715–2718. The process is shown in Scheme I.

Scheme I

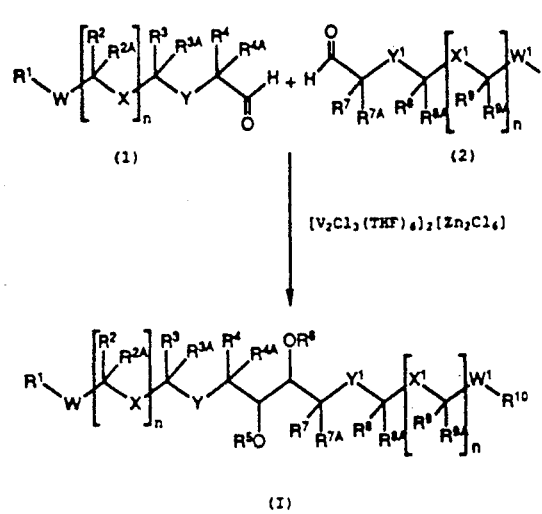

In the operation of this process, an aldehyde of Formula (1) and an aldehyde of Formula (2) are reacted, in a solvent, in the presence of Caulton's Reagent to give a compound of Formula (I) where $R^5$, $R^6$=H. Many of the compounds of formula (I) are available through the operation of the process of Pederson et al. on the corresponding aldehydes. However, the improved process for the reductive coupling of aldhydes, discussed below, is preferred over the method of Pederson et al.

*Improved Process for the Reductive Coupling of Aldehydes.*

Another aspect of the present invention is an improvement of the process disclosed by Pederson et al. for the preparation of 1,4-diamino-2,3-diols. The improvement results in a process which is easier to operate than that of Pederson et al., affords reagents of higher quality and reliability than those of the method of Pederson et al., and results in a higher yield of product than that obtained by Pederson et al.

In practicing the improved reductive coupling process of the present invention, the catalyst is prepared by placing $VCl_3(THF)_3$ in a dry, oxygen-free flask. Zinc-copper couple is then added and the two solids are stirred vigorously. An organic solvent is then added and the mixture is stirred for about 10 minutes, resulting in a deep green solution and black suspension. Next, a solution of the aldehyde in the same solvent as that used for the catalyst, is added to the catalyst over 2-3 minutes. The progress of the reaction is monitored by Thin Layer Chromatography (silica gel with 50% hexane/ethyl acetate as eluent) until it is determined that the reaction is over. The reaction mixture is then subjected to an aqueous work-up and, if necessary, the product obtained is further purified.

The zinc-copper couple utilized in the improved process is prepared following a known procedure, except that filtration with schlenkware was used instead of decanting solvent. L. Fieser and M. Fieser, *Reagents for Organic Synthesis*, Volume I, pp. 1292-1293, Wiley, New York, 1967. The use of a glovebag or drybox instead of schlenkware would be equally satisfactory. The solvents used for the preparation of this reagent are sparged with argon for about 30 minutes before use. The zinc-copper couple obtained is in the form of a free-flowing black powder with a few clumps. The zinc-copper couple prepared in this way is superior to commercially obtained or activated zinc dust. This material reduced V(III) to V(II) in dichloromethane within 10 minutes, whereas the use of commercial zinc dust or activated zinc required several hours and frequently did not provide the color change, described above, which is characteristic of complete reduction.

The improved reductive coupling process operates over a temperature range of from $-78°$ to 100° C. The preferred range is from 0° to 40° C. The most preferred range is from 15° to 25° C.

The use of a solvent is required in practicing the improved reductive coupling process. It is anticipated that any polar, aprotic solvent will be useful. Preferred solvents are hydrocarbons, halogenated hydrocarbons and ethers. Particularly preferred are halogenated hydrocarbons such as dichloromethane and dichloroethane.

The improved reductive coupling process may be run over a time period of 0.1 to 24 hours. It is usually run over the time period of 0.3 to 2 hours. However, as expressed above, in practice it is most desirable to moniter the progress of the reaction by thin layer chromatography.

In practicing the improved reductive coupling process, it is important that the glassware and reagents be dry and free of reactive gases such as oxygen and carbon dioxide. Also, moisture, oxygen and carbon dioxide should be rigorously excluded from the reaction as it is carried out. To accomplish this, it is desirable to perform the reaction under an atmosphere of argon or nitrogen. It is desirable that the aldehyde(s) utilized in the improved reductive coupling process be freshly prepared or purified prior to use.

The molar ratio of each reagent is also important. The process operates where the ratio of zinc-copper couple:$VCl_3(THF)_3$:aldehyde is 1-3:1-3:1 respectively. The preferred ratio of reagents is 1-1.5:2-2.5:1. The most preferred ratio is 1-1.2:2-2.2:1.

The preferred reagents for the aqueous work-up step of the improved reductive coupling process is 10% disodium tartrate. If the product does not contain an acid-sensitive functionality 1N HCl may be used.

If necessary, the 1,4-diamino-2,3-dihydroxybutanes obtained from the improved reductive coupling process can be further purified by recrystallization or chromatography or any method commonly used in organic synthesis.

Stereoselective Preparation of Compounds of Formula (I)

Another aspect of the present invention is a method for the stereoselective preparation of compounds of formula (1) via modification of the method of Pederson et al. The reductive coupling of an aldehyde using the disclosed procedure of Pederson et al. can be expected to produce a number of stereo isomers.

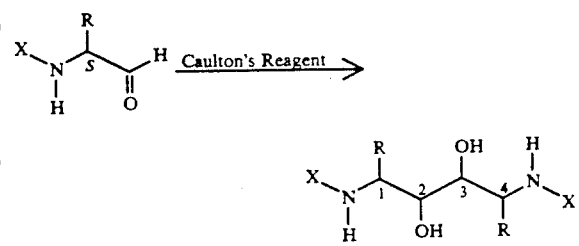

Thus, if an aldehyde, such as depicted in the equation above, with s configuration at the one stereo center is used as the substrate in this reaction, three stereo isomers can be expected to form: (1s,2s,3s,4s), (1s,2r,3r,4s), and (1s,2r,3s,4s). One aspect of the present discovery is the surprising observation that under certain reaction conditions, e.g., changing the reaction solvent, one of these isomers is selectively produced. In addition, the isomer selectivity can be controlled by changing the reaction conditions. This is useful because, even though it is believed all isomers have some level of activity in inhibiting viral protease, certain isomers are more effective, and this aspect of the present invention allows for the selective preparation of the more desirable isomer.

The practice of this aspect of the invention involves using a modified version of the reductive coupling method described by Pederson et al. The usual method to carry out the reductive coupling of aldehydes in the presence of Caulton's reagent is to add the reagent under inert atmosphere to a solution of the aldehyde in a nonpolar halocarbon solvent, usually dichloromethane. This procedure produces predominantly the (1s,2r,3r,4s) isomer. However, if a polar, nonprotic solvent such as dimethylformamide (DMF) is added to the aldehyde solution, before the addition of Caulton's reagent, the predominant isomer is the (1s,2s,3s,4s) isomer. Pederson et al., *J. Am. Chem. Soc.*, 1989, 111, 8014–8016, reports the use of Caulton's reagent for reductive coupling of aldehydes.

Derivatization of Diols

Optionally, after carrying out any of the above described coupling reactions, the product diol (formula (I), $R^5$, $R^6$=H) can then be converted to a derivative ($R^5$ not equal to H, $R^6$=H; $R^6$ not equal to H, $R^5$=H; or $R^5$ and $R^6$ not equal to H) by contacting the diol product with a derivatizing agent in the presence of a suitable base. The monofunctionalized compounds (e.g., $R^5$=H, $R^6$ not equal to H) can be prepared by employing less than or equal to one molar equivalent of derivatizing agent; and the difunctionalized compounds ($R^5$, $R^6$ not equal to H) can be prepared by employing more than two molar equivalents of derivatizing agent. Suitable derivatizing agents include, but are not limited to, acyl chlorides or anhydrides, diphenyl carbonates, and isocyanates using techniques well known to those skilled in the art. Suitable bases are organic and inorganic bases including, but not limited to, aliphatic amines, heterocyclic amines, metal carbonates and metal hydrides.

Preparation of Aldehydes of Formula (1) and Formula (2)

It is anticipated that all aldehydes will work equally well in the process shown in Scheme I and the process described above for the stereoselective synthesis of compounds of formula (1). The method works particularly well with aldehydes that contain an activating group 3,4 or 5 atoms distant from the aldehyde carbon, as discussed by Pederson et al. Aldehydes without activating groups can be coupled using higher temperatures and/or longer reaction times. Different aldehydes can be cross-coupled either by mixing two activated aldehydes and separating the statistical mixture of products, or by reacting an unactivated aldehyde with an activated aldehyde as discussed in the references of Pederson et al. Where the aldehyde of formula (1) has a structure identical to that of formula (2), the resultant compound of formula (I) is a symmetrical 1,4-diamino-2,3-dihydroxybutane. Where the aldehyde of formula (1) has a structure different from that of formula (2), the resultant compound of formula (I) is an unsymmetrical 1,4-diamino-2,3-dihydroxybutane.

Aldehydes of formula (1) and aldehydes of formula (2) can be obtained commercially or can be prepared in a number of ways well known to one skilled in the art of organic synthesis. Preferred methods include but are not limited to those described below for aldehydes of formula (1):

Method A

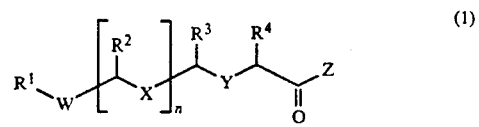

Compounds wherein Z is H, n is zero, and Y is $-C(=Q)NR^{12}-$, and the other variables are as described above, can be prepared by reaction of the amine (II) with a carboxylic acid or derivative (III):

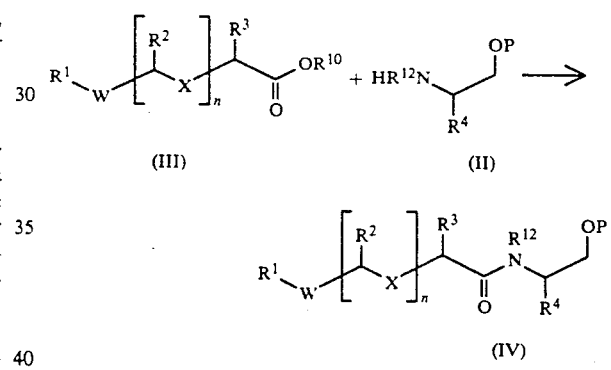

wherein P is hydrogen or optionally an alcohol protecting group, $R^{10}$ is hydrogen or an aliphatic or substituted aromatic group, and the carboxylic acid or ester is activated to nucleophilic attack by methods well known in the art (Bodansky and Bodansky, *The Practice of Peptide Chemistry*, Springer-Verlag, Berlin, 1984, Chapter II, pp. 89–150), with the preferred method employing 1,1'-carbonyldiimidazole as the activating agent, THF as solvent, and 0°–40° C. as temperature, and P=H. If a protecting group is necessary, the preferred group is the 2-methoxyethoxymethyl group. Greene, *Protecting Groups in Organic Chemistry*, Wiley, New York, 1981. Removal of the protecting group if employed, followed by oxidation (see below), provides aldehydes of formulae (V) or (VI).

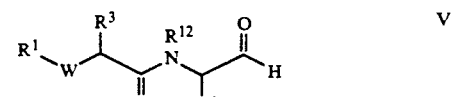

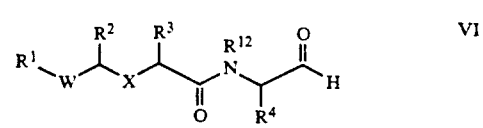

Method B

Thioamides of structure (VII) and (VIII) can be made from the above protected hydroxyamides (IV) followed by treatment with a thionation reagent (Bodansky and Bodansky, *The Practice of Peptide Chemistry*, Springer-Verlag, Berlin, 1984, Chapter II, pp. 89-150), and deprotection followed by oxidation to the aldehyde. A preferred thionation reagent is Lawesson's reagent, and a preferred protecting group is the 2-methoxyethoxymethyl group (Greene, *Protecting Groups in Organic Chemistry*, Wiley, New York, 1981).

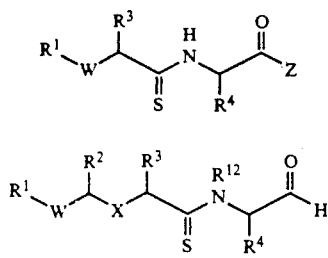

Method C

Compounds of structure (XI) and (XII) wherein Y is —$SO_2NR^{12}$— can be prepared by the reaction of (II) with an activated sulfonate such as (IX), obtained as described by Bodansky and Bodansky, to produce optionally protected alcohols (X):

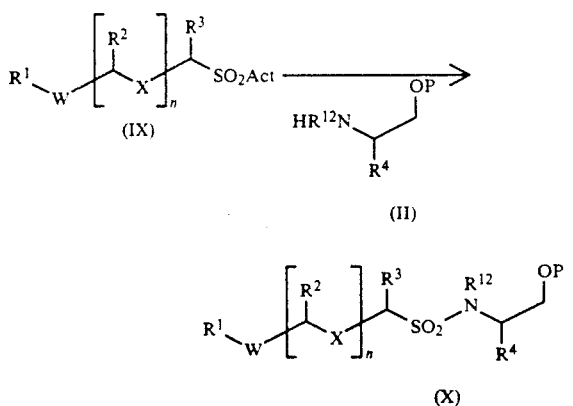

wherein Act is an activating group, preferably chloride, and P is, optionally, a protecting group. Removal of the protecting group if employed, followed by oxidation (see below), provides aldehydes (XI) or (XII).

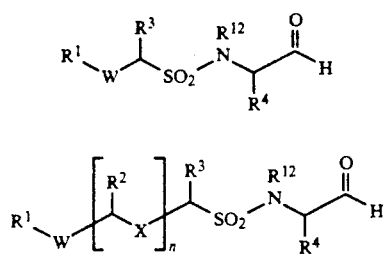

Method D

Compounds wherein Y is —$CH_2NR^{12}$— can be prepared by the reaction of (11) with an alkylating agent such as (XIII):

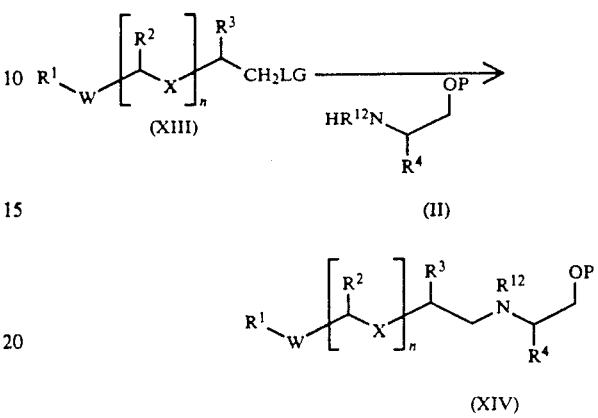

Wherein LG is a leaving group such as halogen or $OSO_2R$, as is described in the art. Bodansky and Bodansky. The preferred method employs a tosylate or iodide as leaving group, and a secondary amine as the nucleophile, i.e., $R^2$ is not hydrogen. A preferred method for the preparation of compounds wherein $R^{12}$ is hydrogen is simply by LiAlH$_4$ reduction of the amides of formula (V), if hydride-sensitive functionality is not present. A final preferred method is the reaction of amines (II) with aldehydes (XXXIII), followed by reduction of the imine by catalyic hydrogenation or by borohydride reduction of the intermediate imine.

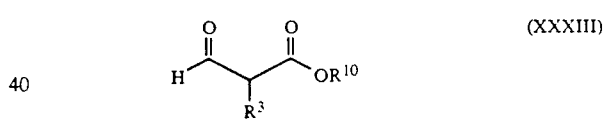

Removal of the protecting group, if employed, followed by oxidation (see below), provides aldehydes (XV) and (XVI)

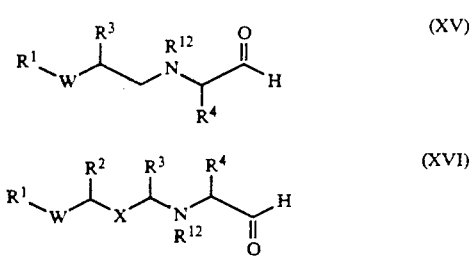

Method E

E} When Y is —C(Cl)=N—, —C(—$OR^{11}$)=N—, or —C(—$NR^{11}R^{12}$)=N— the aldehydes of Scheme I can be advantageously prepared by reaction of secondary amides or thioamides (XVII) with halogenating agents to produce imidoyl halides (X). Bodanszky and Bodansky. The synthesis of amides and thioamides (XVII) is described above (formula II, $R^{12}$=H; see Method A). The imidoyl halides so produced can then be reacted with alcohols to produce imidates (XIX). Gautier, Miocque and Farnoux, in *The Chemistry of Amidines and Imidates,* Patai, Ed., Wiley, London, 1975, pp. 398–405.

reaction with an alcohol (XXIII) in the presence of a base to produce the protected alcohol (XXV).

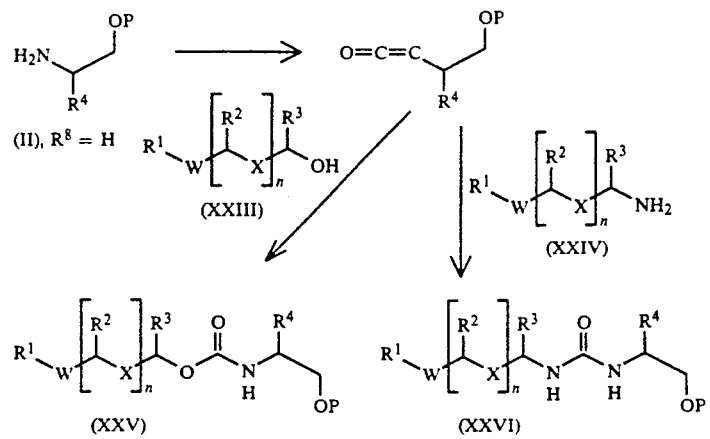

Alternatively, they can be reacted with amines to produce amidines (XX) as shown. Gautier, Miocque and Farnoux, in *The Chemistry of Amidines and Imidates,* Patai, Ed., Wiley, London, 1975, pp. 297-301. Preferred halogenating reagents include phosphorous pentachloride and phosphorous oxychloride.

Cleavage of the protecting group and oxidation to the aldehyde as described below produces (XXII), with the indicated Y values.

(XXII)

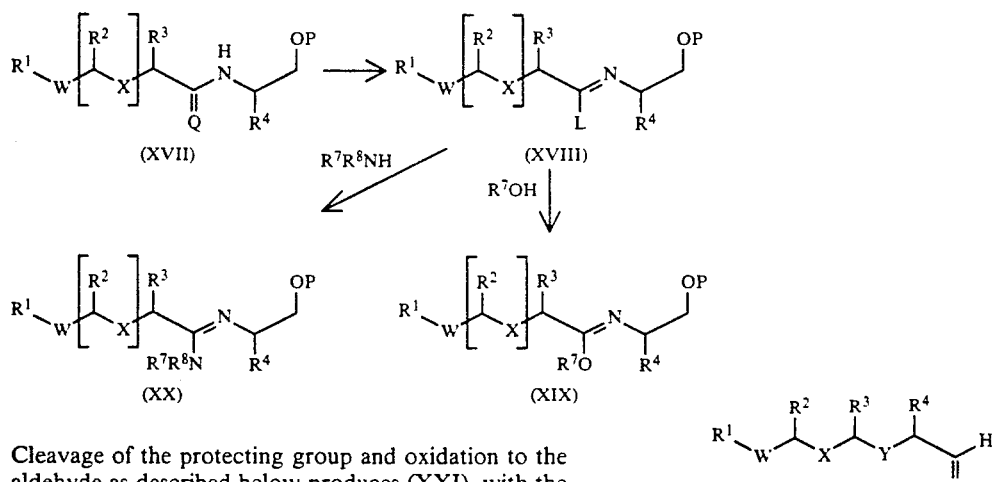

Cleavage of the protecting group and oxidation to the aldehyde as described below produces (XXI), with the indicated Y values.

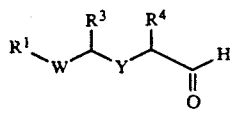

(XXI)

Method F

When Y is —NR$^{12}$C(=O)NR$^{12}$—, the compounds of the invention can be prepared by reacting amine (II) with a derivatizing agent to form the isocyanate or carbamate, followed by reaction with a primary or secondary amine (XXIV), optionally in the presence of a base to produce the protected alcohol derivative (XXVI). Satchell and Satchell, *Chem. Soc. Rev.,* 4, 231-250 (1975).

When Y is —OC(=O)NR$^{12}$, the compounds of the invention can be prepared by reacting amine (II) with a derivatizing agent to form the isocyanate, followed by

Method G: Oxidation of Alcohol Intermediates

The alcohols or protected alcohols discussed above and represented here by formula (XXVIII), (XXVIII)

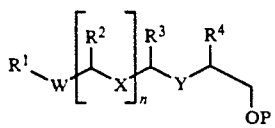

can be readily transformed to aldehydes of formulae (1) or (2). The alcohols represented by formula (XXVIII) can be oxidized directly to the aldehydes of formulae (1) or (2) using methods that are well known in the art. March, *Advanced Organic Chemistry,* Wiley, New York, 1985, pp. 1057-1060. The protected alcohols represented formula (XXVIII) must be deprotected prior to oxidation; this is done using methods that are well known to those in the art. For a recent review, see Tidwell, *Synthesis* 857 (1990). Preferred methods of oxidation include pyridinium dichromate, pyridinium chlorochromate, pyridine/sulfur trioxide, and activated dimethyl sulfoxide. The most preferred method employs dimethylsulfoxide/oxalyl chloride, also known as Swern oxidation in dichloromethane or tetrahydrofuran/dichloromethane at −60° C., followed by treatment with a base such as triethylamine. Tidwell, *Synthesis* 857 (1990).

While the most preferred method of oxidation is gentle and specific, there are functional groups within the contemplated scope that may not survive such oxidation. Examples of these are primary alcohols, amines, indoles, sulfides, thiols. If necessary, these groups can be protected prior to oxidation of the aldehyde. Alternatively, the reductive conditions described below may be used to prepare the aldehyde when oxidative conditions cause difficulties with certain functional groups.

Amine (VIII) can be reacted with any of the above electrophiles, (III, IX or XIII) to form N-methoxyamide (XXIX). It is known that (XXIX) can be reduced cleanly to aldehyde by stoichiometric lithium aluminum hydride, provided that sensitive functionality is not present. Fehrentz and Castro, *Synthesis* 676 (1990).

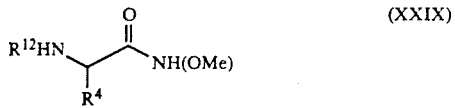

(XXIX)

Finally, there are functional groups within the contemplated scope that will survive neither lithium aluminum hydride nor oxidation. In this occasion, reduction of aminoester (XXX) with one equivalent of diisobutyl aluminum hydride at low temperature, followed by quenching at low temperature, can provide an alternative to the above conditions. Kawamura et al., *Chem. Pharm. Bull* 17, 1902 (1969).

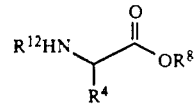

(XXX)

Stereospecific Synthesis of Compounds of Formula (I)

This invention also provides a process for the steriospecific synthesis of certain compounds of formula (I) from mannitol. This process is shown in Scheme II. By steriospecific is meant this process yields one diastereomer based on the stereochemistry of the starting material. The process relies on the key intermediate 1,2,5,6-diepoxy-3,4-O-(alkylidene)hexane. This intermediate is prepared from the hexitol derivative, 2,3-O-alkylidinehexitol, which is itself derived from mannitol. The intermediate may be either the D- or L-stereoisomer; the choice of stereoisomer of the starting material determines the stereochemistry of the final product. This intermediate is prepared in two steps, by conversion of the 1,6-hydroxy groups of 2,3-O-alkylidinehexitol to suitable leaving groups, followed by reaction with a base to effect epoxide formation. The intermediate, 1,2,5,6-diepoxy-3,4-O-(alkylidene)hexane, thus prepared is then used to prepare certain compounds of Formula (I). In the next step of this process, each epoxide group of the intermediate, 1,2,5,6-diepoxy-3,4-O-(alkylidene)hexane, is reacted with an organometallic reagent to give a 2,5-dihydroxy derivative. The resulting hydroxy groups or their derivatives are then converted to amino synthons, e.g., by reaction with azide ion in the presence of compounds such as triphenylphosphine and dialkylazodicarboxylate. This procedure gives a 2,5-diazido derivative. Next, the amino synthons are converted to amino groups, e.g., by catalytic hydrogenation of azide residues. Then, the amino groups are derivatized, e.g., by reaction with an electrophile as shown in Scheme II. Finally, the alkylidine protecting group is removed to yield a product which is a compound of formula (I). Optionally, the dihydroxy groups may be derivatized as discussed above.

Scheme II: Synthesis of compounds of formula (I) form mannitol.

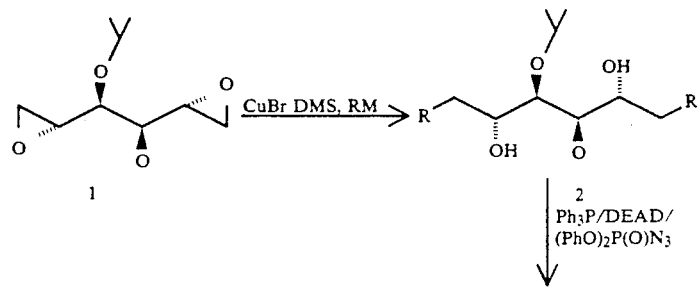

-continued
Scheme II: Synthesis of compounds of formula (I) form mannitol.

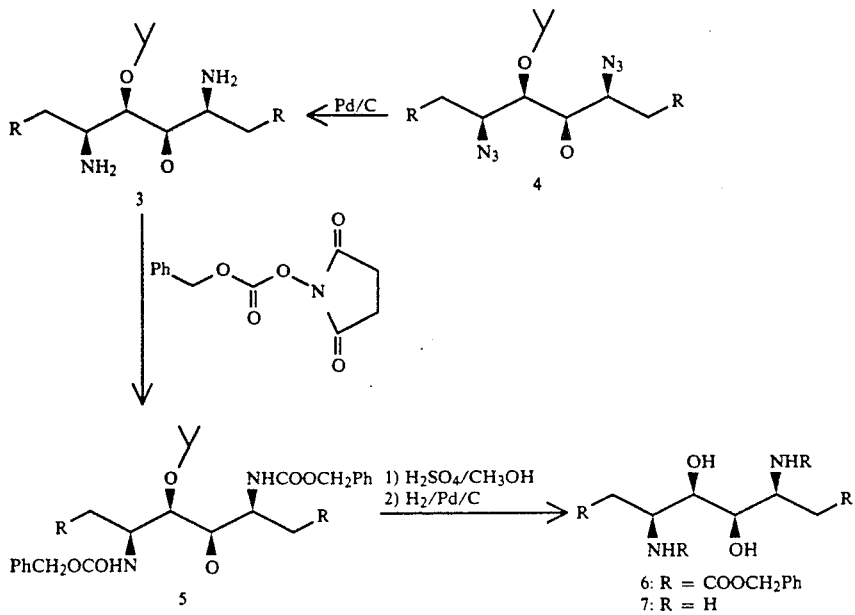

Synthesis of Dihydroxy Intermediate

Another aspect of the present invention is the preparation of the dihydroxy intermediate, 2 in Scheme II, from the addition of a cuprate to the diepoxide intermediate, 1,2,5,6-diepoxy-3,4-O-(alkylidene)hexane, represented by formula 1 in Scheme II. This is a novel process which is useful for the preparation of intermediates which are themselves useful for the preparation of compounds of formula (I). In practicing this aspect of the invention, a solution of an organometallic reagent in an organic solvent is added to a solution of a copper salt in an organic solvent in a reaction vessel. The resulting mixture is then stirred forming an organocuprate. Next, a solution of the diepoxide intermediate, 1,2,5,6-diepoxy-3,4-O-(alkylidene)hexane, represented by formula 1 in Scheme II, in an organic solvent is added to the formed organocuprate to give the dihydroxy product represented by formula 2 in Scheme II. This is stirred until the reaction is complete and is then subjected to a standard aqueous work-up, which isolates the desired product in an organic solvent. Evaporation of the organic solvent affords the desired product which is represented by formula 2 in Scheme II. If necessary, the product obtained from the practice of this aspect of the invention may purified using well known techniques.

The metal of the organometallic reagent can be lithium or magnesium. The preferred metal is lithium. The copper salt may be any copper salt which provides a source of copper(I). Preferred copper salts are copper(I) bromide, copper(I) chloride, copper(I) iodide and copper(I) bromide-dimethyl sulfide complex. Most preferred is copper(I) bromide-dimethyl sulfide complex. The solvent used in this process may be any aprotic solvent. Preferred solvents are dialkyl ethers and mixtures of dialkyl ethers with tetrahydrofuran. The solvent most preferred for use in this process is diethyl ether. The use of tetrahydrofuran by itself is not desirable. Solvents which are incompatible with this process are protic solvents.

In practicing this process it is important to rigorously exclude moisture and reactive gases such as oxygen and carbon dioxide. All reagents and solvents utilized in this process should be moisture free and free of reactive gases. The reaction vessels and containers should be similarly free of moisture and reactive gases. The reaction should be performed under an atmosphere of an inert gas such as nitrogen or argon.

In practicing this aspect of the invention, the reaction may be carried at over a temperature range of $-78°$ to $25°$ C. The preferred temperature range is $-78°$ to $-20°$ C. It is desirable to add the solution of the organometallic reagent to the solution of the copper salt at about $-20°$ C. After adding the 1,2,5,6-diepoxy-3,4-O-(alkylidene)hexane it is desirable to stir the resultant mixture at $0°$ C. The reaction may be carried out over a time period of 5 minutes to 18 hours. The usual reaction time is between 5 minutes and 1 hour.

If necessary, the compounds provided by this aspect of the invention may be purified by any technique useful for the purification of such compounds. Preferred methods include recrystallization and chromatography.

The intermediate represented by formula 5 in Scheme II may also be prepared according to the method shown in Scheme III. In this method, 1,2,5,6-diepoxy-3,4-O-(alkylidene)hexane is reacted sequentially with lithium bis(trimethylsilyl)amide, tetrabutylammonium fluoride and N-(benzyloxycarbonyl)succinimide to give the N-protected diaminodiol intermediate represented by formula 8 in Scheme III. This intermediate is then reacted with triphenylphosphine and diethyl azodicarboxylate to give the bisaziradine intermediate, 9. Finally, reaction of 9 with an organocuprate affords intermediate, 5, which can be further elaborated to compounds of formula (I) as shown in Scheme II.

Synthesis of Aziridines

Another aspect of the present invention is a novel process for the conversion of the N-protected diamino diol, represented by formula 8 in Scheme III, to the bisaziridine intermediate, 9. The process of the present invention is analogous to the Mitsunobu reaction and may be viewed as an intramolecular Mitsunobu reaction. The Mitsunobo reaction is a known method for the conversion of a hydroxy group to another functional group, e.g., to an amino group. Mitsunobu, O., *Synthesis* 1981, 1. The process of the present invention is distinguished from the known Mitsunobu reaction by being an intramolecular reaction which yields an aziridine. No references were found in the literature which disclose the synthesis of an aziridine ring via an intramolecular Mitsunobu reaction in which the amino group is protected with benzyloxy carbonyl. The Benzyloxycarbonylgroup is readily deprotected by simple hydrogenolysis. Other protecting groups such as tosylamides are removed with difficulty and need drastic conditions.

respectively. A preferred ratio of reagents is 1-2:1-2:1. The most preferred ratio is 1:1:1.

The process requires the use of a reaction solvent. Polar aprotic solvents may be used. Preferred solvents include tetrahydrofuran, benzene and toluene. The most preferred solvent is tetrahydrofuran. Protic solvents are incompatible with this process.

In practicing this process it is important to rigorously exclude moisture and reactive gases such as oxygen and carbon dioxide. All reagents and solvents utilized in this process should be moisture free and free of reactive gases. The reaction vessels and containers should be similarly free of moisture and reactive gases. The process should be performed under an atmosphere of an inert gas such as nitrogen or argon.

This process operates over a temperature range of 25°

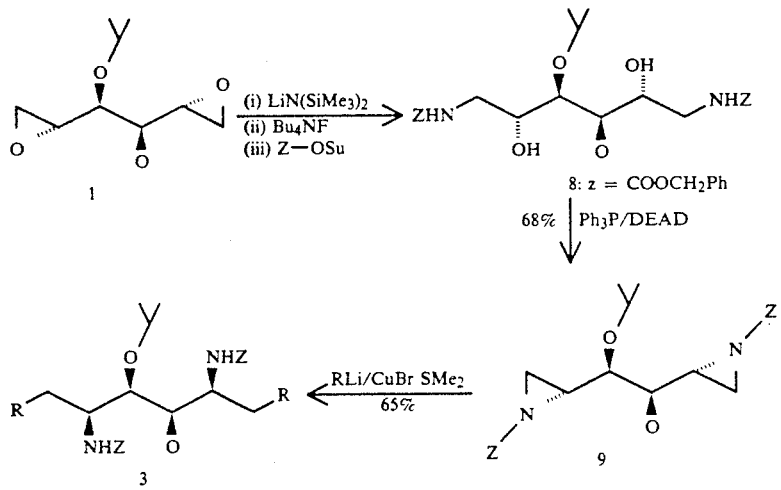

Scheme III: Alternative synthesis of intermediate utilized in mannitol route.

In addition to the utility of this process for the preparation of bisaziridine intermediate 9 of Scheme III, it is also anticipated that this process will have utility for the synthesis of any molecule containing an aziridine ring. The only requirement which must be met in using this process for the synthesis of such molecules is that there be available a suitable precurser molecule which contains at least one functional group pair. A functional group pair is defined as a hydroxy group and an amino group beta to the hydroxy group. Practicing this process on a precurser molecule containing a single functional group pair would give rise to a product containing a single aziridine group. Practicing this process on a precurser molecule containing two functional pair groups, such as formula 8 of Scheme III, gives a product containing two aziridine groups. Similarly, precurser compounds with three or four functional group pairs would give products containing three or four aziridine groups respectively.

In practicing this aspect of the invention, diethyl azodicarboxylate is added to a solution of the precurser molecule, e.g., compound 8 in Scheme III, and triphenylphoshine in an anhydrous organic solvent. The reaction is stirred and its progress is monitored by thin layer chromatography (10:1:10, ethyl acetate/ethyl alcohol/hexane) until it is complete. The reaction mixture is then concentrated to a small volume and the product is purified, if necessary.

The ratio of triphenyl phosphine:diethyl azodicarboxylate:diol utilized in this process may be 1-4:1-4:1 to 85° C. The preferred temperature range is 55° to 85° C. The most preferred temperature range is 70° to 85° C.

The process may be carried out over a time range of 5 minutes to 24 hours. The process is usually carried out over a time range of 5 minutes to 30 minutes.

The aziridine products provided by this aspect of the invention can be further purified, if necessary, by recrystallization or chromatography.

It is further anticipated that this process would be useful for the preparation of saturated 3-7 membered nitrogen containing heterocycles by carrying out an intramolecular Mitsunobo reaction on a precurser molecule containing a protected nitrogen atom and a hydroxyl group separated by 2-6 atoms.

Hydrogenation of Bis(N-CBZ)-diaminodiols

The compounds of formula (I) obtained by any of the above methods can be further elaborated to give other compounds of formula (I). For example, compounds of formula (I) which are bis(N-CBZ)-diaminodiols can be hydrogenated to remove the CBZ protecting group and give the corresponding diaminodiol which may then be further elaborated at the amine residues. The hydrogenation to remove the CBZ protecting group can be carried out using any of the catalysts, solvents and reaction conditions commonly employed to effect removal of this group. A preferred method is to take up the bis(N-CBZ)-diaminodiol in a minimum amount of tetrahydrofuran to permit some solubility, add one volume of ethanol, and optionally 1°-100° volume % acetic acid, and 0.1 weight equivalents of 10% palladium on carbon, and stir under hydrogen at ambient temperature and pressure for 24 hours, occasionally evacuating the reaction flask and refilling with hydrogen. The reaction mixture is worked-up using standard techniques and, if necessary, the diaminodiol obtained is further purified.

Coupling of Diaminodiols

The diaminodiols of formula (I) obtained as described above or from any other source can be further elaborated by reacting them with any one of the many known electrophiles. Coupling reactions of the diaminodiols with activated esters are a particularly useful method for elaborating these compounds. Many conditions and reagents are available to effect coupling. Some preferred methods are exemplified in the Example section. For example, the diaminodiols of formula (I) can be reacted with suitably protected peptides, suitably protected amino acids or carboxylic acids in the presence of dicyclohexylcarbodiimide (DCC) and 1-hydroxybenzotriazole hydrate using procedures commonly employed in peptide synthesis to give the corresponding diamidodiol. The diaminodiols of formula (I) can be reacted with suitably protected peptides, suitably protected amino acids or carboxylic acids in the presence of Benzotriazol-1-yloxytris(dimethylamino)phosphonium hexafluorophosphate (BOP) to give the corresponding diamidodiol. The diaminodiols of formula (I) can be coupled with carbonyldiimidazole. The diaminodiols of formula (I) can be reacted with activated esters such as N-hydroxysuccinimide esters and p-nitrophenylesters to give the corresponding diamidodiol. The diaminodiols of formula (I) can be reacted with isocyanates to give the corresponding urea. The diaminodiols of formula (I) can be reacted with epoxides to give the corresponding addition product.

Biochemistry

The compounds of formula (I) prepared were then tested as described herein to determine their ability to inhibit HIV protease activity.

It is believed the antiviral compounds of this invention can be administered as treatment for viral infections by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams per kilogram of body weight.

Dosage forms (compositions suitable for administration contain from about 1 milligram to about 100 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil was prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

EXAMPLES

Procedure I: Preparation of Intermediates

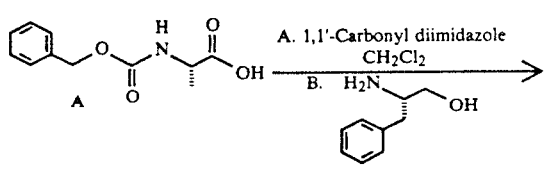

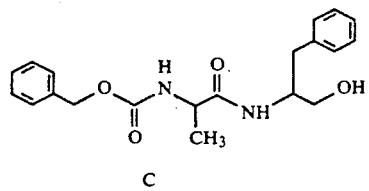

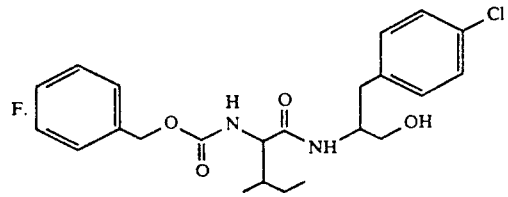

Melting Point 173°-180° C.

NMR (300 MHz, DMSO-d6): (m, 7.65, 1H, NH); 7.2-7.4 (11H, m, aromatic and NH); 5.05 (2H, m, OCH$_2$); 3.9 (m, 1H, CH$_2$OH); 3.8 (dd, 1H, isoleucine a-CH); 3.35-3.5 (m, 2H, CH$_2$OH); 2.6-2.9 (m, 2H, phenylalaninol b-CH$_2$); 1.6 (m, 2H, isoleucine methylene)1.3 (m, 1H, isoleucine methine); 0.8-1.1 (m, 6H, methyls).

N-Carbobenzyloxyalanine (6.63 g, 29.7 mmol; Sigma Chemical Company) was dissolved in 30 mL THF in a 100 mL oven-dried flask under N$_2$ and stirred at room temperature while adding 1,1'-carbonyl diimidazole (4.82 g, 29.7 mmol; Aldrich Chemical Company) neat. Copious bubbling occurred, indicating CO$_2$ formation. The mixture was stirred 30 minutes and (s)-2-amino-1-phenylpropanol (4.5 g, 29.7 mmol; Sigma Chemical Company) was added neat. Stirring was continued for 18 hours. The mixture was poured into a separatory funnel and the flask rinsed with dichloromethane. 100 mL of dichloromethane was added, and 50 mL saturated aqueous disodium-L-tartaric acid. The funnel was shaken, the aqueous layer removed, the organic layer washed with saturated bicarbonate and brine, and dried with magnesium sulfate. Filtration and solvent removal yielded a white solid. Recrystallization by dissolving in hot ethyl acetate, filtering, and adding hexane until cloudy provided 6.76 g (64%) white crystals with properties consistent with alcohol (III).

Melting Point: 120°-121° C.

NMR (300 MHz, CDCl$_3$); δ, ppm: 7.1-7.5 (m, 10 H); 6.45 (broad d, 1H, NH); 5.35 (d, 1H, NH); 5.1 (broad s, 2H, OCH$_2$Ph); 4.1-4.2 (m, 2H, alanine a-CH); 3.6 (m, 2H, CH$_2$OH); 2.85 (m, 2H, phenylalaninol b-CH$_2$); 1.2-1.4 (d, 3H, methyl).

Using the above conditions, the following a-aminoalcohols were prepared:

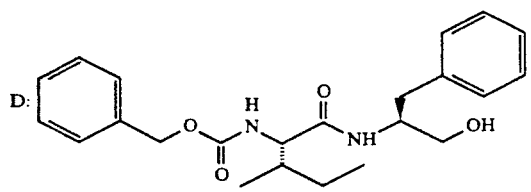

Melting Point: 158°-160° C.

NMR (300 MHz, CDCl$_3$): 7.1-7.6 (m, 10 H); 6.2 (broad d,1H, NH); 5.25 (d, 1H, NH); 5.1 (broad s, 2H, OCH$_2$Ph); 4.2 (m, 1H, isoleucine a-CH); 3.95 (dd, 1H, isoleucine a-CH); 3.6 (m, 2H, CH$_{20}$H); 2.85 (m, 2H, phenylalaninol b-CH$_2$); 1.85 (m, 2H, isoleucine methylene)1.3 (m, 1H, isoleucine methine); 0.8-1.1 (m, 6H, methyls).

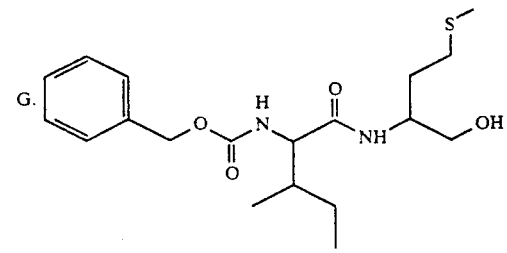

Melting point 147.5°-149.5° C.

NMR (300 MHz, DMSO-d6): 7.65 (d, 1H, NH); 7.2-7.4 (6H, m, aromatic and NH); 5.05 (2H, m, OCH$_2$); 4.7 (dd, 1H, isoleucine a-CH); 3.8 (m, 1H, methionine a-CH); 3.25-3.4 (m, 2H, CH$_2$OH); 2.3-2.5 (m, 2H, methione g-CH$_2$); 1.9 (s, 3H, SCH$_3$); and 0.7-1.9, aliphatics.

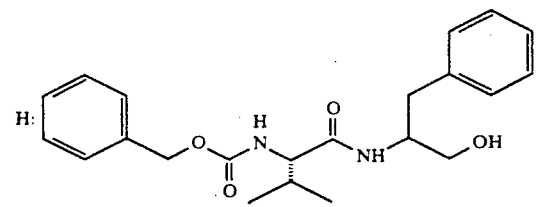

NMR (300 MH$_2$, CDCl$_3$): 7.2-7.2 (m,10H, aromatic); 6.2 (d, 1H, NH); 5.1-5.2 (m, 3H, OCH$_2$, NH); 4.15 (m, 1H, phenylalaninol a-CH) 3.95 (dd, 1H, valine a-CH); 3.5-3.7 (m, 2H, CH$_2$OH); 2.8-2.9 (m, 2H, phenylalaninol β-CH$_2$); 2.1 (m, 1H, valine b-CH); 0.9 (d, 3H, methyl); 0.8 (d, 3H, methyl).

Procedure II: Synthesis of Aldehydes

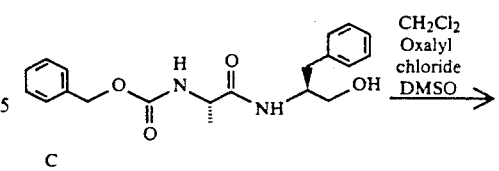

-continued

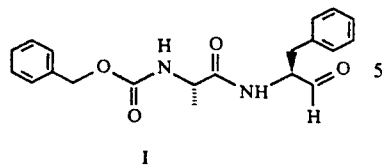

I

A nitrogen-filled, oven-dried 500 mL flask was charged with 35 mL CH$_2$Cl$_2$ and 2.90 g oxalyl chloride (25.25 mmol) under N$_2$ and cooled to −60. Dry dimethylsulfoxide (2.42 g, 33.6 mmol) in 40 mL CH$_2$Cl$_2$ was added over about 10 min. The mixture was stirred 15 min at −60, and alcohol C (6.00 g, 16.8 mmol) was added in 100 mL 1:1 THF/CH$_2$Cl$_2$. After stirring 25 min at −60, triethylamine (6.8 g, 67.2 mmol) was added in 20 mL CH$_2$Cl$_2$. Stirred 30 min at −60 and quenched with 20% aqueous KHSO$_4$ (150 mL) at −60. A white solid formed as water froze. Added 180 mL hexane and warmed to RT. Separated aqueous layer and washed with ether. Combined organic layers, filtered off white solid (presumably unreacted, insoluble starting alcohol) and washed with sat. aq. NaHCO$_3$, water and brine, and dried over MgSO$_4$. Yield: 5.12 g white solid. Analytically pure sample can be obtained by recrystallization from EtOAc/hexane, but the aldehyde is very readily epimerized at the a-carbon, and a small amount of the S,R isomer is generally observed after workup or other manipulation. Additionally, variable amounts of aldehyde trimers oligermers may be observed if the aldehyde is exposed to strong acids in organic solvents.

Melting Point: 125°–126° C.

NMR (300 MH$_2$, CDCl$_3$): 9.6 (br s, 1H, CHO); 7.1–7.4 (m, 10H, aromatic); 6.5 (br, 1H, NH); 5.1–5.2 (m, 3H, NH and OCH$_2$); 4.65 (m, 1H, phenylalaninal a-CH); 4.25 (m, 1H, alanine a-CH); 3.15 (m, 2H, phenylalaninal β-CH$_2$); 1.35 (d, 3H, CH$_3$).

Using the above procedure, the following aminoaldehydes were prepared:

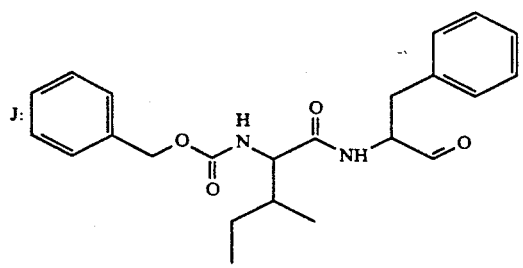

Melting Point 116°–117° C.

NMR (300 MH$_2$, CDCl$_3$): 9.6 (br s, 1H, CHO); 7.1–7.5 (m, 10H, aromatic); 6.45 (br d, 1H, NH); 5.1–5.2 (m, 3H, NH and OCH$_2$); 4.65 (m, 1H, phenylalaninal a-CH); 4.1 (m, 1H, isoleucine a-CH); 3.15 (m, 2H, phenylalaninal β-CH$_2$); 1.85 (m, 2H, isoleucine methylene) 1.4 (m, 1H, isoleucine β-CH$_2$); 0.8–1.1 (m, 6H, methyls).

MS (FAB): M+H (measured) 397.21; (calculated) 397.17

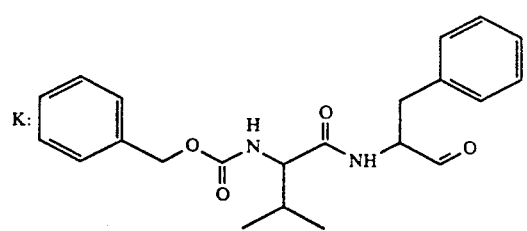

NMR (300 MH$_2$, CDCl$_3$): 9.6 (br s, 1H, CHO); 7.1–7.4 (m, 10H, aromatic); 6.4 (br d, 1H, NH); 5.1–5.2 (m, 3H, NH and OCH$_2$); 4.75 (m, 1H, phenylalaninal a-CH); 4.0 (m, 1H, valine a-CH); 3.15 (m, 2H, phenylalaninal β-CH$_2$); 2.1 (m, 1H, valine β-CH); 0.8–1.0 (m, 6H, methyls).

MS (FAB): M+H (measured) 383.13; (calculated) 383.20

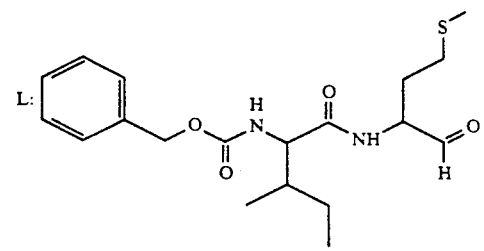

NMR (300 MH$_2$, CDCl$_3$): 9.6 (br s, 1H, CHO).

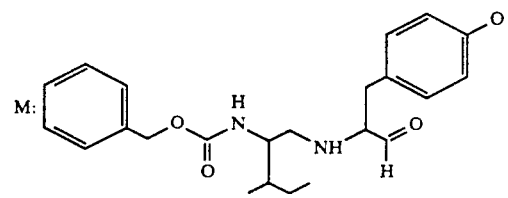

NMR (300 MH$_2$, CDCl$_3$): 9.6 (br s, 1H, CHO); 7.1–7.5 (m, 10H, aromatic); 6.45 (br d, 1H, NH); 5.1–5.2 (m, 3H, NH and OCH$_2$); 4.7 (m, 1H, 4-chlorophenylalaninal a-CH); 4.1 (m, 1H, isoleucine a-CH); 3.1 (m, 2H, 4-chlorophenylalaninal β-CH$_2$); 1.85 (m, 2H, isoleucine methylene) 1.4 (m, 1H, isoleucine β-CH$_2$); 0.8–1.1 (m, 6H, methyls). .

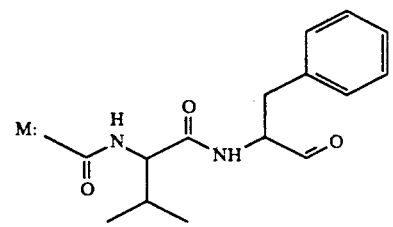

NMR (300 MH$_2$, DMSO-d6; mixture of isomers; major isomer): 9.4 (s, 1H, CHO).

Procedure III: Preparation of Aldehydes

Method A

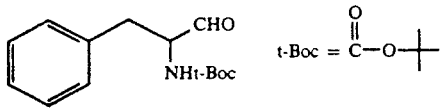

1,1-Dimethylethyl 1-formyl-2-phenylethylcarbamate

Step 1: A solution of 11.0 g (41.5 mmol) of N-tert-butoxycarbonyl-L-phenylalanine (Sigma Chemical Co., St. Louis, Mo.) in 100 mL of CHCl$_3$ at 0° C. was treated with 4.6 mL of N-methylmorpholine followed by 5.4 mL of isobutylchloroformate. After stirring for 10 minutes the reaction mixture was treated with 4.05 grams of N,O-dimethylhydroxylaminehydrochloride followed by 5.8 mL of triethylamine. Upon stirring at 0° C. for 1 hour followed by 16 hours at room temperature, the reaction mixture was worked up by washing with 2×50 mL of 0.2N HCl, 2×50 mL of 0.5N NaOH and 50 mL of saturated NaCL. The organic layer was dried with MgSO$_4$ and concentrated under reduced pressure to yield 12.4 grams of an oil which was used in the next step without further purification. This material showed NMR (CDCl$_3$): 1.4 (s, 9H), 3.0 (m, 2H), 3.2 (s, 3H), 3.65 (s,3H), 4.95 (m, 1H), 5.2 (m, 1H), 7.2 (m,5H); MS cal 309.18 f 309.33.

Step 2: The above material was dissolved in 250 mL of ether, cooled to 0° C. and treated with 9.5 grams (250 mmol) of lithium aluminum hydride. After warming to room temperature and stirring for 1 hour the reaction was quenched with a solution of 0.35 mole KHSO$_4$ in 200 mL of water. The organic layer was separated and the aqueous layer was extracted with 200 mL of ether. The combined ether layers were washed with 2×100 mL 10% HCl, 100 mL NaHCO$_3$ and dried over MgSO$_4$. Upon concentration under reduced pressure, 9.8 g of a pale yellow oil was obtained which solidified upon standing in the refrigerator. The product showed NMR(CDCl$_3$): 1.4 (s, 9H), 2.9 (m, 2H),7.2 (m,5H), 9.6 (s,1H).

A sample prepared in another experiment was purified by chromatography to yield a pure sample which showed the following NMR (CDCL$_3$): 1.4(S<9H), 3.1 (d,J=10HZ,2H), 4.4 (m,1H), 5.05 (m,1H), 7.05 (m,5H), 9.6(s,1H).

Method B

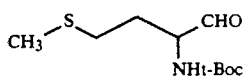

1,1-Dimethylethyl 1-formyl-4-thia-pentylcarbamate

Step 1: A method similar to that reported in Organic Synthesis, volume 67, 69 (1988) was used. Thus, 9.75 grams of N,O-dimethyhydroxylamine hydrochloride in 60 mL of CH$_2$C$_{12}$ was cooled below 5° C. and treated with 7.35 mL of triethylamine through an addition funnel to keep the temperature below 5° C. This material was maintained below 5° C. and added to the reaction mixture 2 minutes after the addition of 7.73 mL of methylchloroformate to a solution at −20° C. of 24.9 grams of N-tert-butoxycarbonyl-L-methionine (Sigma Chemical Co., St. Louis, Mo.) in 400 mL of CH$_2$C$_{12}$ containing 10.97 mL of N-methylmorpholine. After the addition, the reaction mixture was warmed to room temperature and stirred for 4 hours. At the end of this period the reaction mixture was worked up as described above (Method A, Step 1) to yield 24.39 grams of an oil which was used in the next step without further purification. The product showed NMR(CDCl$_3$): 1.4 (s,9H), 1.95 (m, 2H), 2.55 (t, J=8Hz, 2H), 2.8 (s, 6H),4.35 (m,1H).

Step 2: This material was dissolved in 80 mL of ether and added to a suspension of 4.5 grams of lithium aluminum hydride in 400 mL of ether at −45° C. at such a rate that the temperature remained below −35° C. Upon completion of the addition, the reaction mixture was warmed to 5° C., then cooled to −35° C. and treated with 24.85 grams of NaHSO$_4$ in 65 mL of water at such a rate that temperature was below 2° C. The resulting slurry was stirred for 1 hour and then filtered through a pad of celite. The celite pad was washed with 2×100 mL of ether and the combined ether layers were washed with 3×100 mL of 1N HCl, 2×100 mL NaHCO$_3$ and 100 mL of saturated NaCl. The organic layer was dried over MgSO4 and concentrated under reduced pressure to yield 17.67 grams of an oil which was used without further purification. The product showed NMR (CDCl$_3$): 1.4 (S, 9H), 1.9 (m,2H), 2.08 (s, 3H), 2.55 (t, J=10Hz, 2H), 4.25 (m, 1H), 5.2 (m, 1H).

The following aldehydes were prepared by the method of Method B:

1,1-Dimethylethyl 2-oxoethylcarbamate

NMR (CDCl$_3$): 1.45 (S, 9H), 4.05 (d, J=8Hz, 2H), 5.3 (m, 1H), 9.65 (s, 1H).

1,1-Dimethylethyl 1-formylethylcarbamate:

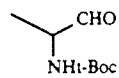

NMR (CDCl$_3$): 1.35 (d, J=10Hz, 3H), 1.45 (s, 9H), 4.2 (m, 1H), 5.15 (m, 1H), 9.55 (s, 1H).

1,1-Dimethylethyl 1-formyl-2-methylpropylcarbamate

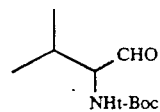

NMR (CDCl$_3$): 0.95 (d, J=7Hz, 1.5H), 1.05 (d, j=7Hz, 1.5H), 1.45 (S, 9H), 2.3 (m, 1H), 4.25 (m, 1H), 5.15 (m, 1H), 9.65 (s, 1H).

1,1-Dimethylethyl 1-formyl-3-methylbutylcarbamate

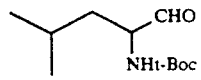

NMR (CDCL$_3$): 0.95 (m, 6H), 1.4 (s, 9H), 1.6 (m, 1H), 4.2 (m, 1H), 5.0 (m, 1H) 9.55 (s, 1H).

1,1-Dimethylethyl 2-formyl-1-pyrrolidinecarbamate

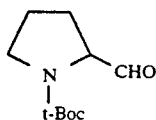

1.48 (s, 9H), 1.72-2.20 (m, 4H), 3.23-3.72 (m, 3H)

1,1-Dimethylethyl 2-oxoethyl-1-phenylcarbamate

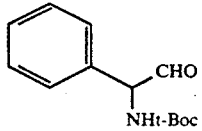

NMR (CDCL₃): 1.4 (s), 7.2 (m), 9.45 (s).

Benzyl 1-formyl-2-phenylethylcarbamate

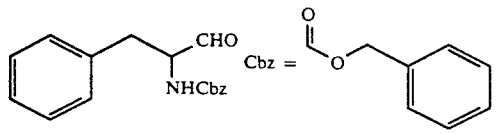

NMR (CDCl₃): 3.15 (d, J=6Hz, 2H), 4.5 (d, j=12.6Hz, 1H), 5.1 (s, 2H), 5.35 (m, 1H), 7.1-7.4 (m, 10H), 9.6 (s, 1H).

1,1-Dimethylethyl 1-formyl-3-phenylpropylcarbamate

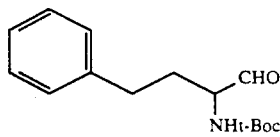

NMR (CDCL₃): 1.45 (s, 9H), 1.9 (m, 2H), 2.75 (m, 2H), 4.25 (m, 1H), 5.1 (m, 1H), 7.2 (m, 5H), 9.55 (s, 1H).

1,1-Dimethylethyl 1-formyl-2-(4-fluorophenyl)ethylcarbamate

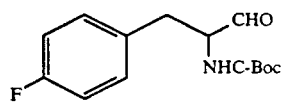

NMR (CDCL₃): 1.45 (s, 9H), 3.1 (m, 2H), 4.4 m, 1H), 5.05 (m, 1H), 7.0 (m, 4H), 9.65 (s, 1H).

1,1-Dimethylethyl 1-formyl-2-(4-iodophenyl)ethylcalrbamate

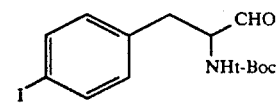

NMR (CDCL₃): 1.4 (s, 9H), 3.1 (m, 2H), 4.4 (s, 1H), 5.1 (m, 1H), 6.9 (d, j=8Hz, 1H), 7.2 (m, 2H), 7.6 (d, j=8Hz, 1H), 9.6 (s, 1H).

1,1-Dimethylethyl 1-formyl-2-(4-benzyloxyphenyl)ethylcarbamate

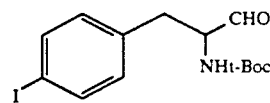

NMR (CDCl₃): 1.45 (s,9H), 3.05 (d, J=12Hz, 2H), 4.4 (m, 1H), 5.05 (s, 2H), 6.9 (d, J=12Hz, 2H), 7.05 (d, j=12Hz, 2H), 7.3 (m, 5H),9.6 (s,1H).

Coupling of Aldehydes With Caulton's Reagent

EXAMPLE 1A AND 1B

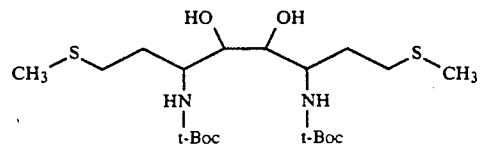

Bis (1,1)-dimethylethyl) (2,3-dihydroxy-1,4-bis(2-(methylthio)ethyl)-1,4-butanediyl)biscarbamate To a solution of 1,1-dimethylethyl 1-formyl-4-thiabutylcarbamate, from Method B, in 1 mL of CH₂Cl₂, under argon, was added 5 mL of the Caultons reagent (prepared via the method reported by Bouma et al, Inorg. Chem., 23, 2715-2718 (1984)) followed by 10 drops of DMF. After stirring over night the reaction mixture was treated with 1 mL of 20% KOH, filtered through celite and the celite pad was rinsed with CH₂Cl₂. The organic layer was separated from the combined filtrates, dried and concentrated under reduced pressure to afford the crude product. This material was chromatographed over silica gel using 20% EtOAc/hexane to afford a fraction containing 33.6 mg of an isomer of the desired product as a crystalline solid. A second fraction was found to contain 12 mg of another isomer of the desired product as a crystalline solid (Example 1B,). Example 1B had MS: cal 469.24 F 469.19.

EXAMPLE 2A

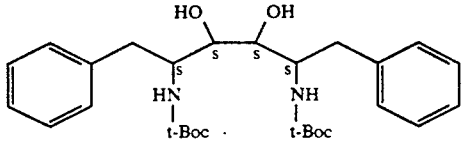

Bis(1,1-dimethylethyl) (2,3-dihydroxy-1,4-(phenylmethyl)-1,4-butanediyl)biscarbamate (1S,2S,3S,4S)

A solution of 1.06 g 1,1-dimethylethyl 1-formyl-2-phenylethylcarbamate, from Method A, in 10 mL of CH₂Cl₂, was treated with 3 mL of DMF followed by 10 mL of Caulton's reagent and stirred for 16 hour. At the end of the period the reaction mixture was treated with 10 mL of 20% NaOH, stirred for 15 minutes and then diluted with 50 mL of ether. After filtering through a celite pad, the celite pad was washed with 3×50 mL of ether and the organic layer was separated from the filtrate. Upon washing with 2×20 mL of NaCl solution, drying over Na₂SO₄ and concentration under reduced pressure the organic layer gave a crude product which was chromatographed over 50 grams of silica gel using 2:1 Hex:EtOAc as eluant. This afforded 0.35 g of the desired product. mp=210-213; NMR: (CDCl₃) 1.4 (s,18H), 3.0 (dd,J=10Hz,2H), 3.2 (m 4H), 4.05 (m,2H), 4.4 (m,4H), 7.2 (m,10H). Upon D₂O exchange, the multiplet at 4.4 became a doublet (d, J=10 Hz, 4H); MS Cal 501.3 F500.85; Anal Cal C: 67.18, H: 8.05, N: 5.60 F C: 66.92, H: 8.31, N: 5.64. The product of this reaction had the stereochemistry, 1S,2S,3S,4S; this was determined as described below.

The stereochemistry of each of the nitrogen bearing carbon atoms is known to be S since the starting material was the L-isomer. The stereochemistry of the hydroxy bearing carbon atoms was determined by conversion of the diol to its corresponding oxazolidinone and measuring the coupling constant between the ring protons. See J. Med. Chem. 30, 1978-83 (1987). The procedure was carried out as follows: to 100 mg of the diol, 4 mL of 4N HCl in dioxane was added and after stirring for 15 min the volatile material was evaporated by blowing nitrogen. Upon subjecting the residual product to high vacuum under KOH it was dissolved in 4 mL of CHCl₃, cooled to 0° C. and 0.28 mL of triethylamine was added. To this, 0.206 mL of 10% phosgene solution in toluene was added and stirred for 16 hour. At the end of this period the reaction mixture was diluted with 75 mL of EtOAc, washed with 10 mL 1N HCl, 10 mL of NaHCO₃, dried and concentrated under reduced pressure to give a product which was purified by flash chromatography to give 22.3 mg of the desired oxazolidinone that crystallized to afford 15.8 mg of material. NMR (CDCl₃) of this material showed a coupling of 7.5 Hz between the protons attached to the oxygen and nitrogen bearing carbon atoms. This coupling constant is consistent with each of the hydroxy bearing carbons being in the S configuration. Thus, this molecule was assigned the stereochemistry 1s,2s,3s,4s.

EXAMPLE 2B

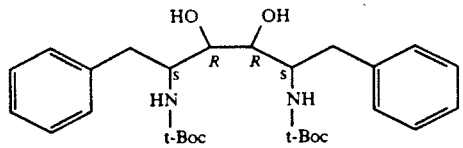

Bis(1,1-dimethylethyl) (2,3-dihydroxy-1,4-(phenylmethyl)-1,4)-butanediyl)bis-carbamate (1S,2R,3R,4S)

To 10 mL of Caulton's reagent, 1.06 g (4 mmol) of 1 1-formyl-2-phenylethylcarbamate, from Method A, was added and after all the aldehyde dissolved 3 mL of DMF was added. The reaction mixture then treated in a manner similar to Example 2A to give 0.41 g of the desired compound as a solid mp 202°-204°, NMR(CDCl₃): 1.4 (s, 18H), 2.9 (m, 4H), 3.4 (s, 2H), 4.0 (s, 2H), 4.8 (d, J=10Hz, 2H), 7.2 (m, 10H). MS cal. 501.3 Found 501.05. Elemental Analysis cal C:67.18, H:8.05, N:5.60; Found C:66.94, H:8.15, N:5.60. This material was shown to have the stereochemistry 1s,2r,3r,4s by the method described in Example 2A; the oxazolidinone produced showed a coupling constant of 5.5 Hz between the protons attached to oxygen and nitrogen bearing carbon atoms.

EXAMPLE 2C

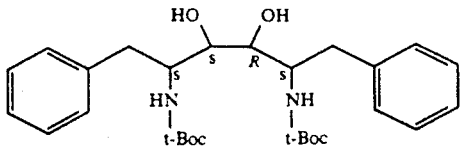

Bis(1,1-dimethylethyl) (2,3-dihydroxy-1,4-(phenylmethyl)-1,4-butanediyl)bis-carbamate (1S,2S,3R,4S)

The 1s,2s,3r,4s isomer was prepared by adding a solution of 1.0013 grams of 1,1-Dimethylethyl 1-formyl-2-phenylethylcarbamate, from Method A, in 2 mL of dry CH₂Cl₂, to 15 mL of Caulton's reagent followed by 3 mL of DMF. This was stirred for 16 h, treated with 10 mL of 20% KOH solution and stirred for 1 hour and filtered through a pad of celite. The organic layer from the filtrate was dried with Na2SO₄ and concentrated under reduced pressure to give a crude product. This material was chromatographed over 80 grams of silica gel eluting with 20% EtOAc to give 0.166 g of product, mp=172°-174° C. MS: calcd. 501.30, found 501.66.

EXAMPLE 2D

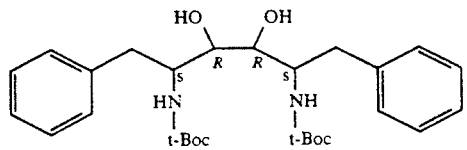

Bis(1,1-dimethylethyl) (2,3-dihydroxy-1,4-(phenylmethyl)-1,4-butanediyl)bis-carbamate (1S,2R,3R,4S)

To 0.997 gram (4 mmol) of 1,1-dimethylethyl 1-formyl-2-phenylethylcarbamate, from Method A, under argon, 10 mL of dry CH₂Cl₂ was added and after all the aldehyde has dissolved 10 mL of Caulton's reagent was added. The reaction was then treated in a manner similar to that described in Example 16 to give 0.332 g of the desired product with NMR identical to that of Example 2B.

EXAMPLE 3

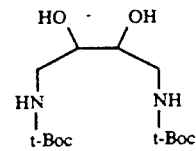

Bis(1,1-dimethylethyl) (2,3-dihydroxy-1,4-butanediyl)biscarbamate 1,1-Dimethylethyl 2-oxoethylcarbamate was couple a described in Example 2B to give from 0.997 grams of the aldehyde 39 mg of the desired product. NMR (CDCl₃, D₂O) 1.45 (s, 18H), 3.2-3.5 (m, 4H), 3.6 (t, J=10Hz, 4H), 5.15 (m, 2H); MS Calcd 321.20, F321.29.

EXAMPLE 4

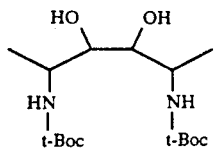

Bis(1,1-dimethylethyl) (2,3-dihydroxy-1,4-dimethyl-1,4-butanediyl)biscarbamate 1,1-Dimethylethyl 2-oxoethylcarbamate was coupled as described in Example 2B to give from 0.693 g of the aldehyde 0.342 g of the desired product. NMR (CDCl$_3$, D$_2$O): 1.2 (d, J=10Hz, 6H), 1.4 (s, 18H), 3.35 (s, 2H), 3.85 (m, 2H), 4.95 (m, 2H); MS Calcd 349.23; F 349.35.

EXAMPLE 5

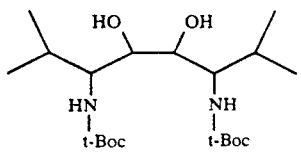

Bis(1,1-dimethylethyl) (2,3-dihydroxy-1,4-(1-methylethyl)-1,4-butanediyl)biscarbamate 1,1-Dimethylethyl 1-formyl-2-methylpropylcarbamate was coupled as described in Example 2D to give, from 0.845 g of aldehyde, 0.160 g of the desired product, mp 156-159; NMR (CDCl$_3$, D$_2$O): 1.0 (d, J=10Hz) 1,45 (s, 18H), 2.0 (m, 2H), 3.2 (t, J=10Hz, 2H), 3.65 (s, 2H),5.0 (d, J=10Hz, 2H).

EXAMPLE 6

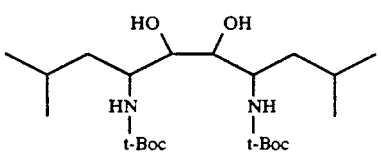

Bis(1,1-dimethylethyl) (2,3-dihydroxy-1,4-(2-methylpropyl)-1,4-butanediyl)biscarbamate 1,1-Dimethylethyl 1-formyl-3-methylbutylcarbamate was coupled as described in Example 2D to give, from 0.933 g of the aldehyde, 0.1799 g of the desired product, mp 152-153, NMR (CDCl$_3$, D$_2$O): 0.95 (m,12H), 1,4 (s,18H),1.6-1.8 (m, 6H), 3.2 (s, 2H), 3.8 (m, 2H), 4.95 (m, 2H); Elemental Analysis: Cal C:61.08 H:10.25 N:6.48; Found C:60.79 H:10.31 N:6.51; Ms Cal 433.33 F 432.96.

EXAMPLE 7

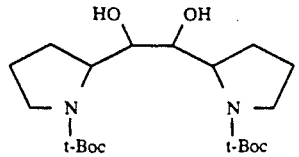

Bis(1,1-dimethylethyl) 2,2'-(1,2-dihydroxy-1,2-ethanediyl)-1-bis(pyrrolidinecarboxylate)

1,1-Dimethylethyl 2-formyl-1-pyrrolidinecarbamate was coupled as described in Example 2D to give, from 1.99 grams of the aldehyde, 1.14 grams of the desired product. NMR (CDCl$_3$) 1.45 (s, 18H), 1.6-2.0 (m, 8H), 3.35 (m, 2H), 3.45 (m, 2H), 3.6 (m, 2H), 3.95 (m, 2H); MS Calc 401.27 Found 401.34.

EXAMPLE 8

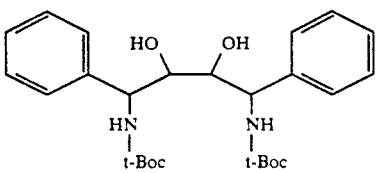

Bis (1,1-dimethylethyl) (2,3-dihydroxy-1,4-diphenyl-1,4-butanediyl)biscarbamate 1,1-Dimethylethyl 2-oxoethyl-1-phenylcarbamate was as described in Example 2D to give, from 1.13 grams of the aldehyde, 0.51 grams of the product which upon crystallization from EtOAc gave 0.089 g of the desired product. NMR (CDCl$_3$, D$_2$O): 1.4 (s, 9H), 3.8(m, 2H), 7.2 (m, 5H); MS Calcd 473.27 Found 473.35.

EXAMPLE 9

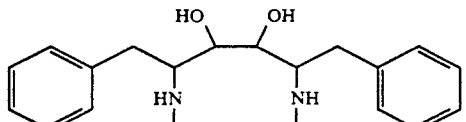

Bis(Dimethylethyl) (2,3-dihydroxy-1,4-(phenylmethyl)-1,4-butanediyl)biscarbamate Benzyl 1-formyl-2-phenylethylcarbamate was coupled as described in Example 2D to give, from 2.02 grams of the aldehyde, 0.407 grams of the desired product, mp 201°-205° C.; NMR (DMSO-d$_6$) 2.7 (m, 4H), 3.3 (s, 2H), 4.2 (m, 4H), 7.2 (m, 2OH). Material prepared in another similar experiment showed MS Cal 569.27 Found 569.31.

EXAMPLE 10

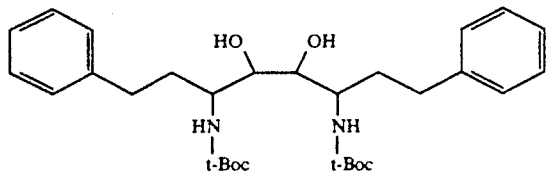

Bis(1,1-dimethylethyl)
(2,3-dihydroxy-1,4-(2-phenylmethyl)-1,4-butanediyl)-biscarbamate 1,1-Dimethylethyl 1 -phenylpropylcarbamate was coupled as described in Example 2D to give, from 2.86 grams of the aldehyde, 0.75 grams of the desired product, mp 174°-175° C. NMR (CDCl$_3$, CD$_3$OD): 1.35 (s,18H), 1.8 (m, 4H), 2.6 (t, J=10Hz, 4H), 3.4 (s, 2H), 3.6 (m, 2H), 7.1 (m, 10H); MS Cal 529.33 Found 529.44.

EXAMPLE 11

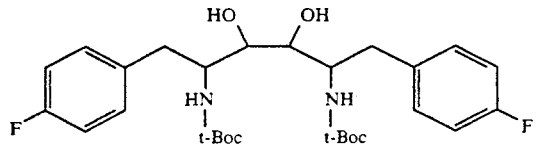

Bis(1,1-dimethylethyl)
(2,3-dihydroxy-1,4-(4-fluorophenyl)methyl)-1,4-butanediyl)biscarbamate 1,1-Dimethylethyl 1-formyl-2-(4-fluorophenyl)ethyl-carbamate was coupled as described in Example 2D to give, from 2.99 grams of the aldehyde, 1.38 grams of the desired product, which upon crystallization afforded 0.172 g of a solid mp 189°-91° C., NMR (CDCl$_3$, D$_2$O): 1.3 (2 peaks), 2.8 (m, 4H), 3.4 (m, 2H), 3.7 (m, 2H), 7.0 (m, 10H); MS calcd 537.28 Found 537.41.

EXAMPLE 12

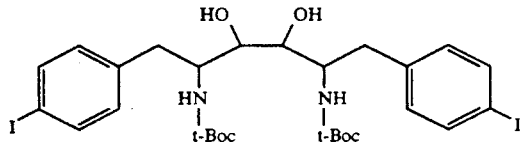

Bis(1,1-dimethylethyl)
(2,3-dihydroxy-1,4-(4fluorophenyl)methyl)-1,4-butanediyl)biscarbamate 1,1-Dimethylethyl 1-formyl-2-(4-iodophenyl)ethyl-carbamate was coupled as described in Example 2D to give, from 1.13 grams of aldehyde, 0.66 grams of the desired product, mp 191-194 NMR (CDCl$_3$): 1.3 (s, 18H), 2.8 (m, 4H), 3.4 (m, 2H), 3.7(m,2H), 6.95 (d, J=10Hz, 2H), 7.2 (m, 4H), 7.55 (d, J=10Hz, 2H).

EXAMPLE 13

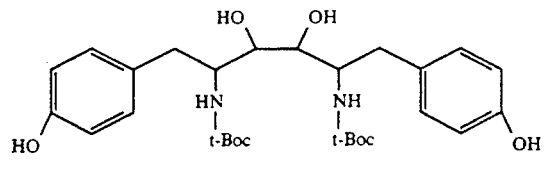

Bis(1,1-dimethylethyl)
(2,3-dihydroxy-1,4-(4-hydroxyphenyl)methyl-1,4-butaneidyl)biscarbamate 1,1-Dimethylethyl 1-formyl-2-(4-benzyloxyphenyl-)ethyl carbamate was coupled as described in Example 2B to give, from 1.42 g of the aldehyde, 0.238 g of the o-benzyl protected intermediate. This material was not characterized further but was subjected to the following conditions to remove the benzyl protecting group. It was dissolved in 20 mL of MeOH:EtOAc 1:1, treated with 50 mg of 10% Pd/C and H$_2$ gas was bubbled through for 3.5 hour. At the end of this period the reaction mixture was filtered through a celite pad and concentrated under reduced pressure to yield the crude product which was purified by chromatography over 25 grams of silica gel using 1:2 Hex:EtOAc to afford 62.3 mg of the desired product, mp 110-112; NMR (CDCl$_3$) 1.35 (s, 18H), 2.8 (m, 4H), 3.4 (s, 2H), 3.7 (m, 2H), 6.7 d,J=15Hz, 4H), 7.0 (d, J=15Hz, 4H); MS Calcd 533.29 F 532.82.

EXAMPLE 14

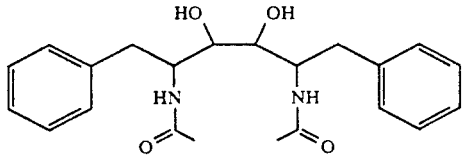

N,N'-((2,3-dihydroxy-1,4-(phenylmethyl)-1,4-butanediyl))bisacetamide 100 mg (0.2 mM) of bis (1,1-dimethylethyl) (2,3-dihydroxy-1,4-(phenylmethyl)-1,4-butanediyl)biscarbamate, (1S,2R,3R,4S), from Example 2D, was stirred in 2 ml of 4N HCl in dioxane. The dioxane and HCl were removed under vacuum and the residual material was taken up in 2 ml of CHCl$_3$, and treated with 55 microliters of triethylamine and 57 microliters of acetic anhydride. The resultant mixture was stirred for one hour and was then worked up by diluting with 50 ml of ethyl acetate, washing the organic layer with 1N HCl, saturated NaHCO$_3$, and drying the organic layer over magnesium sulfate. Filtration and evaporation gave 92.7 mg of crude product. Preparative plate chromatography (with ethyl acetate as the eluant) gave 36.2 mg of product.

EXAMPLE 15

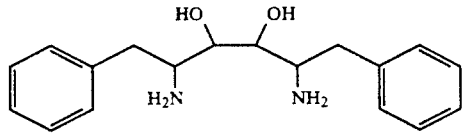

2,5-Diamino-1,6-diphenyl-3,4-hexanediol dihydrochloride 20 mg of bis(1,1-dimethylethyl) (2,3-dihydroxy-1,4-(phenylmethyl)-1,4-butanediyl)biscarbamate, (1S,2S,3S,4S), from Example 2A, was treated with 2 ml of 4N HCl in dioxane. After stirring for 15 minutes, the HCl and dioxane were removed under vacuum. Thin Layer Chromatography (1:1, Hexane/Ethyl acetate) showed that all of the starting material was converted. Treatment with Ninhydrin demonstrated the presence of the amino groups. NMR showed that the Boc groups were gone.

EXAMPLE 16

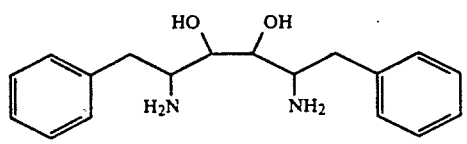

2,5-Diamino-1,6-diphenyl-3,4-hexanediol dihydrochloride 20 mg of Bis(1,1-dimethylethyl) (2,3-dihydroxy-1,4-(phenylmethyl)-1,4-butanediyl)biscarbamate (1S,2R,3R,4S), from Example 2B, was treated as described in Example 15.

EXAMPLE 17

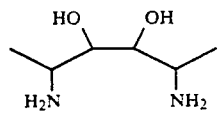

2,5-Diamino-3,4-hexanediol dihydrochloride 20 mg of Bis(1,1-dimethylethyl) (2,3-dihydroxy-1,4-dimethyl-1,4-butanediyl)biscarbamate from Example 4 was treated as described in Example 15.

EXAMPLE 18

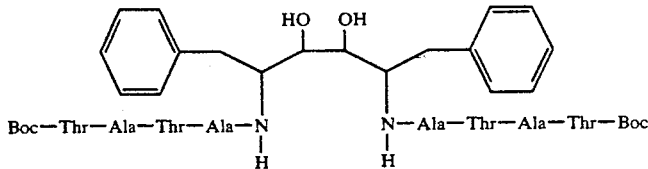

Bis(Boc-Thr-Ala-Thr-Ala), N,N'((2,3-dihydroxy-1,4-(phenylmethyl)-1,4-butanediyl))biscarbamate 29.4 mg of Bis(1,1-dimethylethyl) (2,3-dihydroxy-1,4-(phenylmethyl)-1.4-butanediyl)biscarbamate (1S,2S,3S,4S), from Example 2C, was reacted with Boc-Thr-Ala-Thr-Ala-O-Succinamide and triethylamine in 2 ml of acetonitrile. Filtration gave 0.1083 g of product which was tested without further purification.

EXAMPLE 19

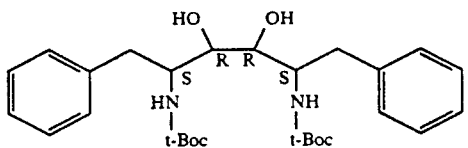

Alternative Synthesis of Product of Example 2B From D-Mannitol via Cuprate Addition Synthesis of carbamic acid, ((2,3-dihydroxy-1,4-(phenylmethyl)-1,4-butanediyl))-bis-, bis(1,1-dimethylethyl) ester, (1S,2R,3R,4S) from d-mannitol:

1,6-Di-O-(p-toluenesulfonyl)-2,3-O-isopropylidene-D-mannitol 2

A solution of 6.667 g (30 mmol) of 2,3-O-isopropylidene-D-mannitol 1 (purchased from Aldrich Chemical Co.) in 30 mL pyridine was cooled to −20° C. and treated with 12.582 g (66 mmol) of p-toluenesulfonyl chloride and the stirring continued for 20 minutes at −20 C., 20 minutes at 0° C. and 20 minutes at room temperature. The reaction mixture was diluted with dichloromethane and washed with 1N HCl and saturated NaHCO$_3$. The extract after drying over anhydrous magnesium sulfate was concentrated and the residue purified (325 g, silica gel column chromatography using 2:3 EtOAc: Hexane as the eluting solvent) to provide 10.425 g (66% yield) of compound 2. This material showed NMR (CDCl$_3$): d 1.278 (s, 6H), 2.458 (s, 6H), 3.783 (m, 4H), 4.095 (q, 2H, $J_{AB}$=10.66Hz, $J_{Ax}$=5.67Hz), 4.33 (q, 2H, $J_{AB}$=10.6Hz, $J_{BX}$=1.98), 7.35 (d, 2H, J=1.74Hz), 7.81 (d, 2H, J=1.76Hz).

1,2,5,6-Diepoxy-3,4-O-(isoproylidene)hexane 3

A solution of 10.425 g (19.65 mmol) of compound 2 in 200 mL of anhydrous methanol was cooled at 0° C. and treated with 10.86 g (78.58 mmol) of K$_2$CO$_3$. The ice bath was removed and the contents stirred at room temperature for 20 minutes. The mixture was filtered and the filtrate was concentrated. The residue was dissolved in dichloromethane and the extract was washed with water and brine. The residue after removal of the solvent was purified (200 g silica gel column using 1:5 EtOAc: Hexane as the eluting solvent) to provide 2.95 g (80% yield) of compound 3. This material showed NMR (CDCl$_3$) d 1.45 (s, 6H), 2.4 (q, 2H, $J_{AB}$=4.94Hz, $J_{AX}$=2.65Hz), 2.86 (q, 2H, $J_{AB}$=4.94Hz, $J_{BX}$=4.2Hz), 3.13 (m, 2H), 3.85 (dd, 2H, $J_1$=2.3Hz, $J_2$=1.46)

1,6-Diphenyl-3,4-O-isopropylidene-2,5-hexanediol 4

A suspension of 9.25 g (45 mmol) of cuprous bromide-dimethyl sulfide complex in 40 mL anhydrous ether was stirred at −20° C. and 1.8M 50 mL (1.8M, 90 mmol) solution of phenyllithium was added dropwise. The contents were stirred for 30 minutes at −20° C. and then warmed up to 0° C. A solution of 2.807 g of compound in 20 mL anhydrous ether was added to the above mixture and the contents stirred for 30 minutes at 0° C. The excess reagent was quenched with saturated ammonium chloride and warmed up to room temperature. The contents were then filtered and the filtrate and the washings were washed with water and brine. The ether extract after drying over anhydrous magnesium sulfate was concentrated and the residue was purified (150 g silica gel column using 1:5 followed by 1:4 EtOAc: Hexane as the eluting solvent) to provide 4.577 g (89%) of compound 4. This material showed NMR (CDCl$_3$): d 1.455 (s, 6H), 2.7 (q, 2H, $J_{AB}$=13.8Hz, $J_{AX}$=7.9Hz), 3.15 (q, 2H, $J_{AB}$=13.8Hz, $J_{BX}$=2.5Hz), 3.75 (m, 4H), 7.28 (m, 10H).

2,5-Diazido-1,6-diphenyl-3,4-O-(isopropylidene)hexane 5

A solution of 900 mg (2.63 mmol) of compound 4, 2.76 g (10.52 mmol) of triphenylphosphine in 20 mL of dry tetrahydrofuran was stirred with 250 mg of molecular sieves 2A at −78° C. 22.9 mL (0.46M, 10.52 mmol) solution of hydrazoic acid in xylene was added to the above mixture and stirred for 5 minutes at −78° C. This was followed by the addition of 1.66 mL (10.52 mmol) of diethylazodicarboxylate. The mixture was then allowed to warm up to room temperature in the same bath and stirred for 18h. The excess reagents were quenched by the addition of 0.4 mL (10 mmol) of methanol at 0° C. After stirring the mixture for 30 minutes at room temperature, it was concentrated to a small volume and purified (33 g silica gel column using hexane followed by 1:40 EtOAc: Hexane as the eluting solvent) to provide 836 mg of mixture of 5 and undesired side products. The mixture was difficult to purify at this stage and used directly in the next step.

2,5-Diazido-1,6-diphenyl-3,4-hexanediol 6

A solution of 570 mg of the mixture (as mentioned in the previous experiment) in 5 mL of ethanol and 1.67 mL of water was stirred with 1.67 g of Bio-Rad AG-50-W-X8 acid exchange resin at 70° C. bath for 18 h. The contents were filtered and washed with methanol. The filtrate and the washings were combined and concentrated. The residue was extracted with dichloromethane and dried over anhydrous magnesium sulfate. The residue after removal of the solvent was purified (20 g silica gel column using 1:3 EtOAc: hexane as the eluting solvent) to provide 102 mg (11% yield from 4) of 6. This material showed NMR (CDCl$_3$): d 2.95 (q, 2H, $J_{AB}$13.7Hz, $J_{AX}$=7.9Hz), 3.06 (q, 2H, $J_{AB}$=13.7Hz, $J_{BX}$=6.3Hz), 3.55 (m, 2H), 3.62 (bs, 2H), 7.3 (m, 10H).

2,5-Diamino-1,6-diphenyl-3,4-hexanediol 7

A solution of 67 mg (0.19 mmol) of 6 in 4 mL of methanol was stirred with 30 mg of 10% palladium on carbon under 1 atmosphere hydrogen pressure for 18 hours at room temperature. The mixture was filtered through a 0.45 micron Millipore filter and the residue washed with methanol. The filtrate and the washings were concentrated to provide 45 mg (79% yield) of 7. This material showed NMR (CDCl$_3$): d 2.64 (m, 8H), 7.283 (m, 10H).

2,5-(N,N-Di-tert-butoxycarbonyl)diamino-1,6-diphenyl-3,4-hexanediol 8

A solution of 45 mg (0.015 mmol) of compound 7 in 2 mL of absolute ethanol was stirred with 152 mg (0.58 mmol) of N-(tert-butoxycarbonyl)phthalimide for 18 hours at room temperature. The reaction mixture was diluted with 20 mL water and extracted with three 20 mL portions of dichloromethane. The dichloromethane extract was washed with 0.3N NaOH and brine. The residue after removal of the solvent was purified (33 g silica gel coulmn using 7% isopropanol in hexane as the eluting solvent) to provide 26 mg of pure and 12 mg of slightly contaminated 8 (total yield 51%).

This material has identical spectral data with the compound described in Example 2B.

EXAMPLE 19B

Alternative Synthesis of Product of Example 2B From D-Mannitol via Cuprate Addition (2S,3R,4R,5S)-1,2,5,6-Diepoxy-3,4-O-(isopropylidene)hexane 1: This compound was prepared following the literature procedure (Y. L. Merrer et al, Heterocycles, 25, 541, 1987). This material showed NMR (CDCl$_3$): d 1 45 (s, 6H), 2.4 (q, 2H, $J_{AB}$=4.94Hz, $J_{AX}$=2.65Hz), 2.86 (q, 2H, $J_{AB}$=4.94Hz, $J_{BX}$=4.2Hz), 3.13 (m, 2H), 3.85 (dd, 2H, $J_1$=2.3Hz, $J_2$=1.46)

(2S,3R,4R,5S)-1,6-Diphenyl-3,4-0-isopropylidene-2,5-hexanediol 2: A suspension of 18.5 g (90 mmol) of cuprous bromide-dimethyl sulfide complex in 80 mL anhydrous ether was stirred at −20° C. and 1.8M 100 mL (1.8M, 180 mmol) solution of phenyllithium was added dropwise. The contents were stirred for 30 minutes at −20° C. and then warmed up to 0° C. A solution of 5.614 g of compound in 40 mL anhydrous ether was added to the above mixture and the contents stirred for 30 minutes at 0° C. The excess reagent was quenched with saturated ammonium chloride and warmed up to room temperature. The contents were then filtered and the filtrate and the washings were washed with water and brine. The ether extract after drying over anhydrous magnesium sulfate was concentrated and the residue was purified (325 g silica gel column using 1:10 followed by, 1:5 followed by 1:4 EtOAc: Hexane as the eluting solvents) to provide 8.035 g (78%) of compound 2. This material showed NMR (CDCl$_3$): d 1.455 (s, 6H), 2.7 (q, 2H, $J_{AB}$=13.8Hz, $J_{AX}$=7.9Hz), 3.15 (q, 2H, $J_{AB}$=13.8Hz, $J_{BX}$=2.5Hz), 3.75 (m, 4H), 7.28 (m, 10H).

(2S,3R,4R,5S)-2,5-Diazido-1,6-diphenyl-3,4-O-(isopropylidene)hexane 3: A solution of 16.781 g (49.00 mmol) of compound 2, 38.6 g (147 mmol) of triphenylphosphine in 300 mL of dry tetrahydrofuran was cooled in an ice bath and 23.1 ml (147 mmol) of diethylazodicarboxylate was added to the stirred mixture behind shield. 31.7 mL (147 mmol) of diphenylphosphorylazide (Caution—this reagent should be stored at 0° C. and handled with care. Some azides may be explosive!) was added to the above mixture and the contents were further stirred at 0° C. for 5 minutes. The mixture was then allowed to warm up to room temperature in the same bath and stirred for 1 h. TLC in 1:5 ethyl acetate/hexane indicates disappearance of compound 2 and formation of 3. The excess reagents were quenched by the addition of 6.0 mL (150 mmol) of methanol at 0° C. After stirring the mixture for 30 minutes at room temperature, it was concentrated to a small volume (NOTE: do not concentrate to the extent that solids separate. Also small amount of dichloromethane is needed to keep the contents in solution while loading on silica gel column. Use of more than necessary amount of dichloromethane results inefficient separation.) and purified [800 g silica gel column using hexane (500 mL)

followed by 1:40 EtOAc: Hexane (1000 mL) and finally 1:20 ethyl acetate/hexane elutes the desired compound (3000 mL)] to provide 15.523 g of mixture of 3 and undesired side products. The mixture was difficult to purify at this stage and used directly in the next step.

(2S,3R,4R,5S)-2,5-Diamino-1,6-diphenyl-3,4-O-(isopropylidene)hexane 4: The above material (15.523 g) was divided in 3 equal portions and each portion dissolved in 75 mL absolute ethanol, flushed with nitrogen and each portion stirred with 1.5 g of 10% palladium on carbon under hydrogen (hydrogen balloon) for 18h. TLC 1:10 ethyl acetate/hexane solvent indicates disappearance of starting material. (If incomplete add 0.5 g of 10% palladium on carbon and stir under fresh balloon of hydrogen). Combined yield of 12.516 g was obtained.

(2S,3R,4R,5S)-2,5-(N-(Benzyloxy)carbonyl)-diamino)-1,6-diphenyl-3,4-O-(isopropylidene)hexane 5: A solution of 13.67 g (40.2 mmol) of compound 4 in 100 ml dimethylformamide was stirred in ice-bath and treated with 21.93 g (88 mmol) of benzyloxycarnonyloxysuccinimide. The ice-bath was removed and the contents were stirred for 18 hours at room temperature. The excess reagent was quenched by treatment with 0.61 ml (10 mmol). The contents were diluted with water and extracted with dichloromethane (3× of ethanolamine. The mixture after complete removal of solvents was purified (500 g silica gel column using 1:5 followed by 1:4 EtOAc:Hexane) to provide 20.457 g (83.6% yield) compound 5.

(2S,3R,4R,5S)-2,5-Di-(N-((Benzyloxy)carbonyl)amino)-3,4-dihydroxy-1,6-diphenylhexane 6: A solution of 20.457 g (33.61 mmol) of compound 4 in 50 ml 90% aqueous trifluoroacetic acid was stirred in ice-bath and then at room temperature. for 18h. The reaction mixture was poured with stirring in 560 ml of 1M ice-cold sodium hydroxide and then rest of the trifluoroacetic acid was quenched with sat. sodium bicarbonate. The precipitated solid was filtered dried under vacuum and crystallized from chloroform to provide 15.02 g (77% yield) of compound 6 (M. P. 209-210).

(2S,3R,4R,5S)-2,5-diamino-3,4-dihydroxy-1,6-diphenylhexane 7: A solution of 10.432 g (18.36 mmol) of compound 6 in 500 ml THF and 500 ml ethyl alcohol was stirred with 1.043 g of 10% palladium on carbon at room temperature. for 18h over 1 atmosphere hydrogen pressure. The mixture was filtered through celite pad and the filtrate was concentrated to provide 6.06 g yield) of compound 7. The oil was triturated with diethyl ether and the white solid was filtered and washed to provide pure 7 (M. P. 92-94).

EXAMPLE 19C

Alternative Synthesis of Aziridine Product of Example 2B From D-Mannitol via Biszairidine Intermediate 1,6-Di(N,-(benzyloxycarbonyl)amino)-2,5-dihydroxy-3,4-O-(isopropylidene)hexanediol 8

In a 250 mL Round Bottom Flask was placed 20 mL of 1M (20 mmol) of Lithium Bis (trimethylsilyl)amide and the contents cooled in ice bath and 1.87 g(10 mmol) of diepoxide 1 in 3 ml of THF was added to the above mixture and the contents were stirred for 18h while allowing the contents to warm up to room temperature. It was cooled back in an ice-bath and quenched with 20 ml (20 mmol) of 1M HCl in anhydrous ether. It was stirred for 5 minutes and then treated with 40 mL of 1M tetrabutylammonium fluoride in THF at 0° C. and then immediately warmed-up to room temperature and stirred for additional 2 hours. It was then cooled to 0° C. and then treated with 5.98 g (24 mmol) of N-(benzyloxycarbonyl)succinimide, stirred for 15 minutes, ice-bath was removed and the contents stirred at room temperature for 18h. It was concentrated and the residue dissolved in dichloromethane and the extract washed twice with water and once with brine. The residue after removal of dichloromethane was chromatographed (130 g silica gel, 2:3 followed by 1:1 ethyl acetate/hexane) to provide 2.44 g (yield 50%) of 8.

(2S,3R,4R,5S)-1,2:5,6-(N,N'-Dibenzyloxycarbonyl)-diimino-3,4-O-(isopropylidene)hexanediol 9

In a 500 mL Round Bottom Flask was placed 12.147 g (24.89 g mmol) of above compound, 15.669 g (59.7 mmol) of triphenylphosphine and dissolved in 150 mL of anhydrous THF. To the above mixture was added 9.40 mL (59.7 mmol) of diethyl azodicarboxylate and refluxed for 30 minutes under nitrogen. TLC indicated completion of the reaction(10:1:10 ethyl acetate/ethyl alcohol/hexane and 1:2 ethyl acetate/hexane). It was concentrated to a small volume and chromatographed (325 g silica gel column, 1:3 followed by 1:2 ethyl acetate/hexane as the eluting solvent) to provide 7.147 g ( yield, 64%) of compound 9.

(2S,3R,4R,5S)-2,5-Di(N-((benzyloxy)carbonyl)-diamino)-1,6-diphenyl-3,4-O-(isopropylidene)hexane 5

In a 50 mL R. B. Flask under nitrogen and in a glove . was placed 1.37 g (6.66 mmol) of cuprous bromide-dimethylsulfide complex and suspended in 2 mL ether and cooled to −20° C. and 6.66 mL (13.33 mmol) 2M solution of phenyllithium in 70:30 cyclohexane/ether was added dropwise to the mixture at −20° C. The mixture stirred at −20° C. for 30 minutes and then warmed to 0° C. 754 mg of above bisaziridine derivative in 2 mL ether and 6 mL THF was added to to the mixture at 0° C and stirred for 30 minutes at 0° C. TLC in 1:3 ethyl acetate/hexane indicated disappearance of the starting material. The excess reagent was quenched with saturated ammonium chloride, the mixture filtered, diluted with 20 mL of water and extracted with 2×25 mL of dichloromethane. The mixture was chromatgraphed (33 g silica gel column and 1:5 ethyl acetate/hexane as the eluting solvent) to provide 475 mg (47%) of 5. This intermediate is identical to compound 5 of Example 19B from which the final compound can be prepared according to the route provided by that Example.

EXAMPLES 20 AND 21

EXAMPLE 20

Synthesis of 2,5-(N-2-Pyridylacetyl-L-Ile)diamino-1,6-diphenyl-3,4-hexanediol

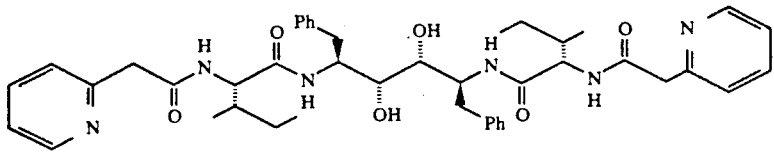

EXAMPLE 21

Synthesis of 2,5-(N-2-Pyridyl-L-Ile,N'-2-pyridyl-D-Ile)diamino-1,6-diphenyl-3,4-hexanediol

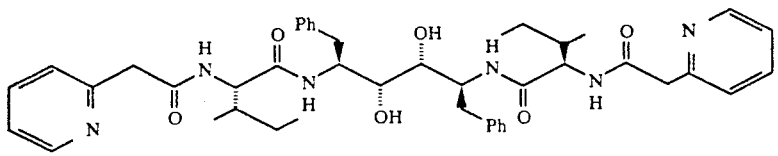

Step 1: 2-Pyridylacetyl-Ile allyl ester

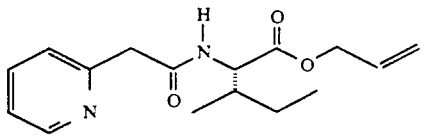

2-Pyridylacetyl-Ile allyl ester

A mixture of 1.717 g (5 mmol) pyridylacetic acid hydrochloride, 868 mg (5 mmol) of isoleucine allyl ester p-toluene sulfonate salt, molecular sieves 4° A type in dimethylformamide were stirred at 0° C. and 1.74 ml (10 mmol) of diisopropylethylamine was added to generate free amines. After stirring the contents at 0° C. for 15 minutes it was treated with 1.23 g (6 mmol) of dicyclohexylcarbodiimide and the contents were warmed up to room temperature. The mixture was stirred for 18 h, filtered and the residue purified (130 g, silica gel column chromatography using 1:1 EtOAc:hexane as the eluting solvent) to provide 712 mg (49% yield) of 2 pyridylacetyl-Ile allyl ester. This material showed $^1$H NMR (CDCl$_3$): d 0.87 (d, 3H, J=6.9Hz), 0.894 (t, 3H, J=7.4Hz), 1.15 (m, 1H), 1.42 (m, 1H), 1.92 (m, 1H), 4.6 (m, 3H), 5.2–5.7 (m, 2H), 5.85 (m, 1H), 7.25 (m, 1H), 7.668 (d×t, 1H, J$_1$=3.84, J=7 7Hz), 8.01 (bm, 1H), 8.577 (bd, 1H).

Step 2: 2-Pyridylacetyl-Ile

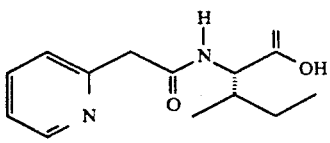

2-Pyridylacetyl-Ile

A mixture of 276 mg (0.95 mmol) of 2-pyridylacetyl 1- ester in 2 ml of 1,4-dioxane was stirred at room temperature and 1 ml of 1.0N sodium hydroxide was added in three equal portions after 15 minute intervals and the contents were stirred at room temperature for a total of 2 hours. The mixture was neutralized with addition of 1.0 ml (1 mmol) of 1N HCl. The mixture was diluted with 5 ml water and extracted with dichloromethane. The aqueous layer was saturated with solid sodium sulfate while stirring with 20 ml of chloroform. The combined organic extracts after removal of solvents provided 174 mg (74% yield) of 2-pyridylacetyl-Ile. This material showed $^1$H NMR (CDCl$_3$): d 0.927 (d, 3H, J=6.8Hz), 0.927 (t, 3H, J=7.3Hz), 1.05–2.0 (bm, 3H), 3.872 (AB, 2H, JAB=13.8Hz), 4.539 (d×d, 1H, J$_1$=5.21Hz, J$_2$=8.22 Hz), 7.32 (d×d×d, 1H), 7.52 (bm, 1H), 7.785 (d×t, 1H, J$_1$=7.71Hz, J$_2$=1.8Hz), 8.53 (d×d×d, 1H).

Step 3: A solution of 101 mg (0.336 mmol) of 2,5-diamino-1,6-diphenyl-3,4-hexanediol and 168 mg (0.67 mmol) of 2-pyridylacetyl-Ile in 5 ml of dichloromethane was stirred with 25 mg of molecular sieves and 166 mg (0.8 mmol) of dicyclohexylcarbodiimide at room temperature for 18 h and filtered. The residue after removal of solvent was purified (33 silica gel column using 4%, 7% and 10% methanol in chloroform) to provide 46.5 mg (18%) of desired coupled product and 39.5 mg (15.3%) of a diastereomer to which was assigned structure 21 based on the spectral data. The compound of Example 20 had C-2 symmetry and showed $^{13}$C NMR (CDCl$_3$): d 11.452, 15.643, 24.242, 35.975, 38.200, 44.912, 52.358, 58.680, 72.775, 122.273, 124.083, 126.171, 128.200, 129.299, 137.291, 138.056, 149.138, 149.138, 155.166, 169.740, 171.149. The compound of Example 21 had no C-2 symmetry and showed twice the number of $^{13}$C NMR resonances (CDCl$_3$) d 11.454, 11.572, 14.380, 15.669, 24.234, 26.144, 35.891, 36.354, 38.102, 38.241, 44.837, 44.863, 52.504, 52.699, 57.485, 58.802, 72.897, 73.037, 122.197, 122.293, 124.065, 124.118, 126.140, 126.241, 128.220, 128.267, 128.381, 129.310, 137.209, 137.292, 138.121, 138.186, 149.167, 149.190, 155.205, 155.253, 169.673, 169.853, 171.319, 171.596.

EXAMPLE 23

Improved Method to Couple Aldehydes: Synthesis of Compound of Example 9

Bis(dimethylethyl) (2,3-dihydroxy-1,4-(phenylmethyl)-1,4-butanediyl)biscarbamate Step A: Preparation of V(Cl$_3$(THF)$_3$ V(Cl)$_3$ (Aldrich, 25 g) was added to 400 mL argon-sparged THF and the suspension heated to reflux under air-free conditions. After 24 hours, the mixture was cooled to room temperature and filtered under rigorously air-free conditions (schlenkware, glove bag or dry box), rinsed 4 times with 50 mL pentane, transferred to a schlenk tube and evacuated at 0.1 torr for 1 hour.

The tris-THF adduct is a bright salmon color, between pink and red. If caution is taken to avoid exposure to air, this material can be kept for months in a schlenk tube. On very brief exposure to air, however, the material turns to dusty orange, then tan, and must be discarded.

Step B: Preparation of An·Cu

Zinc-copper couple was prepared following the of Fieser and Fieser[3] (L. Fieser and M. Fieser, *Reagents for Organic Synthesis*, Volume I, pp. 1292-1293, Wiley, New York, 1967), except that filtration with schlenkware was used instead of decanting solvent. The use of a glovebag or drybox would be equally satisfactory. Also, solvents were sparged with argon for 30 minutes before use. A free-flowing black powder with few clumps was isolated. This material reduced V(III) to V(II) in dichloromethane within 10 minutes, whereas the use of commercial zinc dust or activated zinc required several hours and frequently did not provide the color change characteristic of complete reduction (see below).

Step C: Coupling Procedure

VCl$_3$(THF)$_3$ (1.32 g, 3.53 mmol) was weighed into an argon-filled 35 mL RBF using a schlenk tube. Zinc-copper couple (138 mg, 2.12 mmol), weighed quickly in air, was added. The flask was fitted with a dropping funnel previously filled with argon and the two solids were stirred vigorously. Dry dichloromethane (8 mL) was added via the funnel, and the mixture was stirred for 10 minutes, by which time it had turned deep green with suspended black.

1,1-Dimethylethyl 1-formyl-3-phenylpropylcarbamate (1.00 g, 3.53 mmol), freshly prepared by Swern oxidation of the requisite alcohol, was added over 2-3 minutes in 4 mL dichloromethane. Stirring at room temperature and following by TLC (50% EtOAc/hexane) indicated complete loss of aldehyde starting material after 1.5 hours.

Notes: after addition of CH$_2$Cl$_2$, rigorous exclusion of air is necessary; before addition, exercise reasonable care. When exposed to even small amounts of air, the reduced material rapidly oxidizes to a deep wine-red. If this happens, discard the reaction and start over.

If the characteristic deep green color—best seen by holding a white sheet of paper behind the flask and looking at the gas-solvent interface—does not appear within 10-30 minutes, it is best to discard the reaction and re-prepare the reagents.

The reaction mixture was poured into a separatory funnel containing 50 mL dichloromethane and 100 mL 10% aqueous disodium tartrate (1N HCl can be used if acid-sensitive functionality is not present). After gentle shaking, separating, and washing the aqueous layer two times with 25 mL dichloromethane, the combined organic layers were washed with saturated sodium bicarbonate and dried with magnesium sulfate. Solvent was removed, the crude solid was taken up in minimum CHCl$_3$, and 0.5 volumes hexane added. On sitting overnight, copious white crystals formed. Isolated 0.62 g (62%) product diol, mp 202°–204° C. Spectral data are consistent with the assigned structure.

EXAMPLES 24–98

Examples 24–98 were prepared by one of the methods described below. The method of preparation and physical data are shown in Table I.

Method 2C (Coupling of Aldehydes)

The improved coupling method, exemplified in Step C of Example 23, was used to prepare a number of the compounds shown in Table I.

Method 3 (Hydrogenation of Bis-N-CBZ-Diaminodiols)

The (bis-N-CBZ)-diaminodiols obtained either by vanadium coupling reaction or D-mannitol route can be hydrogenated and further elaborated at the amine residues. Table I shows examples prepared via this route.

Synthesis of Compound of Example 39

In a 200 ml R.B. Flask a suspension of 3.432 g (4.32 mmol) of the above intermediate in 25 ml ethanol and 25 ml methanol was stirred with a suspension of 343 mg 10% palladium on carbon under 1 atmospheric hydrogen pressure at room temperature for 18 hours. The suspension of starting material went into solution. The mixture was filtered through a celite pad and and the residue washed with ethanol. The filtrate and the washings were concentrated and the residue purified (130 g silica gel column using first 3% and finally 6% methanol in chloroform as the eluting solvent) to provide 1.848 g (81.3%) of 39 as a white solid.

Method 4 (Coupling of Diaminodiols)

The diamines obtained via Method 3 can be further elaborated by reaction with various electrophiles. Some preferred reaction conditions that provide active compounds are given below. Many other conditions and reagents can, of course, be employed.

4C: DICYCLOHEXYLCARBODIIMIDE (DCC) COUPLING

Dicyclohexylcarbodiimide (DCC) coupling in the presence 1-hydroxybenzotriazole hydrate was carried out according to standard procedure in peptide synthesis. A representative synthesis is described below.

Synthesis of Compound of Example 26

A solution of 101 mg (0.336 mmol) of 2,5-diamino-1,6-diphenyl-3,4-hexanediol, 108 mg (08 mmol) of 1-hydroxybenzotriazole and 168 mg (0.67 mmol) of 2-pyridylacetyl-Ile in 5 ml of dichloromethane was stirred with 25 mg of molecular sieves and 166 mg (0.8 mmol) of dicyclohexylcarbodiimide at room temperature for 18 h and filtered. The residue after removal of solvent was purified (33 g silica gel column using 4%, 7%, and 10% methanol in chloroform) to provide 86 mg (33% yield) of 26. The compound has C-2 symmetry and showed $^{13}$C NMR (CDCl3): d 11.452, 15.643, 24.242, 35.975, 38.200, 44.912, 52.358, 58.680, 72.775, 122.273, 124.083, 126.171, 128.200, 129.299, 137.291, 138.056, 149.138, 149.138, 155.166, 169.740, 171.

4B: BOP COUPLING

BOP-Benzotriazol-1-yloxytris(dimethylamino)phosphonium hexafluorophosphate coupling was carried out according to the procedure by B. Castro et al. (Tetrahedron Lett., 1975, 14, 1219-1222). A representative synthesis is described below.

Synthesis of Compound of Example 81

BOC-Thiozolidine-4-carboxylic acid (0.94 g; 0.40 mmol) and [NH$_2$CH(isopropyl)-C(O)—N—CH(OH)—]$_2$ (0.100 g; 0.20 mmol) were dissolved in 10 ml of DMF, and BOP (0.177 g; 0.4 mmol) and triethylamine (0.056 ml; 0.40 mmol) were added in aliquots to maintain a pH of 7-8. The reaction was stirred for 18 hours. The residue after removal of solvent was purified by column chromatography on Sephadex LH-20 in methanol to provide 81 as amorphous solid (0.137 g). FAB/MS calculated for C$_{46}$H$_{68}$N$_6$O$_{10}$S$_2$ (928.44). Found 929.64 (M+H).

4C: CARBONYLDIIMIDAZOLE COUPLING

Synthesis of Compound of Example 88

N-MSOC-isoleucine (393 mg, 2.1 equivalents) was dissolved in THF; added carbonyldiimidazole (227 mg, 2.1 equivalents) at room temperature. Stirred under TLC showed loss of starting material. The reaction mixture was diluted with chloroform and 10% aqueous disodium L-tartrate was added. The layers were separated and the aqueous layer washed 1× with chloroform. Washed combined organic layers with saturated aqueous sodium bicarbonate and brine, dried with magnesium sulfate, filtered and removed solvent to obtain 540 mg white solid. Recrystallized from hot chloroform/hexane to obtain 343 mg fine white crystals; NMR consistent with 88. Melting point 222°-225° C. (dec).

4D: N-HYDROXYSUCCINIMIDE ESTER COUPLING

N-hydroxysuccinimide esters, available from Sigma Chemical Company or Advanced ChemTech, were used.

SYNTHESIS OF COMPOUND OF EXAMPLE 89

In a 300 ml R.B. flask a solution of 6.000 g (20mmol) of diamino diol in 60 ml of dimethylformamide was cooled in an ice bath. The mixture was treated with 14.070 g (44mmol) of Z-Isoleucine succinimide ester (available from Sigma Chemical Company or Advanced ChemTech) and stirred at room temperature for 18 hours. A precipitate had formed and was dissolved by adding one liter of chloroform. The mixture was then washed with water and the organic layer separated, dried over magnesium sulfate, filtered, and concentrated. The residue was dissolved in one liter of chloroform and the hexane added to precipitate out the desired product; however, after filtration the solid was contaminated with N-Hydroxysuccinimide. It was further purified (750 g silica gel column using first 1% followed by 1.5% methanol in chloroform as the eluting solvent) to provide 9.723 g (61.2%) of 89.

4E: p-NITROPHENYLESTER COUPLING (1) With hydroxybenzotriazole hydrate:

Synthesis of Compound of Example 92

Diaminodiol of example 63 (250 mg, 1.0 equivalent), was dissolved in 5 mL DMF and N-CBZ-asparagine-p-nitrophenylester (373 mg, 2 equivalents, Sigma Chemical Company) and 1-hydroxybenzotriazole hydrate (135 mg, 2 equivalents) were added and the mixture was stirred overnight. The reaction mixture was triturated with THF for one hour, the solid was filtered off, washed with THF and chloroform, and collected to obtain 400 mg white crystals. NMR of the material is consistent with the structure.

(2) Without hydroxybenzotriazole hydrate:

Synthesis of Compound of Example 90

Diaminodiol of example 15 (200 mg, 1.0 equivalent) was dissolved in 5 mL DMF and N-CBZ-(d)-phenylalanine-p-nitrophenylester (332 mg, 2 equivalents, Sigma Chemical Company) was added and the mixture was stirred overnight. One volume of water was added, the solid was filtered off and washed with 1:1 water/DMF, then with water and finally with ether, and collected to obtain 320 mg white crystals. NMR showed the material to be consistent with the structure.

4F: CONDENSATION WITH ISOCYANATES

Synthesis of Compound of Example 67

In a 500 ml R.B. Flask, 2.500 g (4.75mmol) of the above intermediate in 100 ml dimethylformamide was cooled in an ice bath. The mixture was treated with 1.29 ml (10.45 mmol) of benzyl isocyanate via syringe and the mixture allowed to warm to room temperature where a precipitate started forming within 5 minutes. Within 30 minutes 100 ml more dimethylformamide was added to aid stirring. After stirring the mixture at room temperature a total of 2 hours the mixture was filtered and the solid washed with first dimethylformamide and then chloroform. The solid was transferred and dried to provide 3.230 g (85.7%) of 67 as a white solid.

4G: CONDENSATION WITH EPOXIDES

Epoxides can be condensed with diaminodiols. A representative example is given below.

SYNTHESIS OF COMPOUND OF EXAMPLE 71

The corresponding epoxide was prepared from 1-adamantyl bromomethyl ketone by reduction with sodium borohydride in absolute ethanol and treatment with potassium tert-butoxide. The adamantyl ethylene oxide was reacted with [NH$_2$-Val-Phe[CH(OH)-]]$_2$ in methanol refluxing at 70 degrees Celsius overnight and chromatogrammed using Sephadex LH-20 column. (2 equivalents of oxide was used for every 1 equivalent of diol).

TABLE I
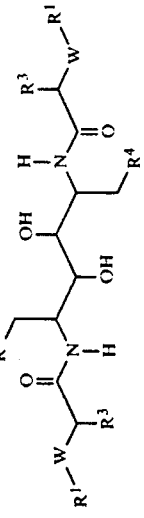
| EXAMPLE | R¹-W | R³ | R⁴ | IC$_{50}$ GAG mg/ml | IC$_{90}$ CELLS mg/ml | MP PHYSICAL DATA | METHOD |
|---|---|---|---|---|---|---|---|
| 24 | 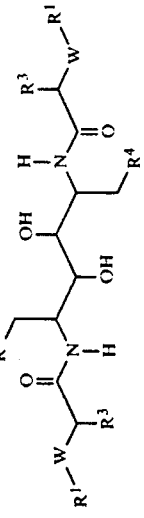 | 2-butyl | Ph | 0.056 | 1 | 232-234 | 4A |
| 25 | 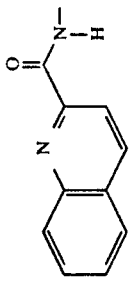 | 2-butyl | Ph | 0.69 | >30 | 191-194 | 4A |
| 27 | 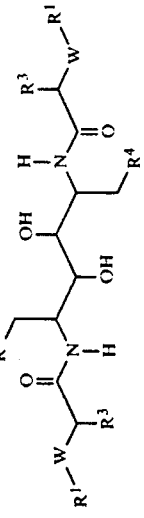 | 2-butyl | Ph | 0.177 | >30 | 207-213 | 4A |
| 28 | 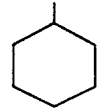 | 2-butyl |  | 0.155 | 2.4 | (777.99) | 4A |
| 29 | 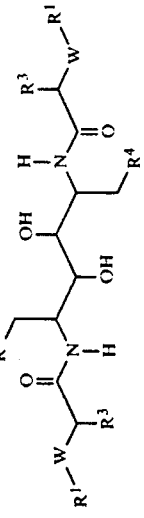 | 2-propyl | Ph | 0.041 | 0.95 | 248-252 | 4A |
| 30 | 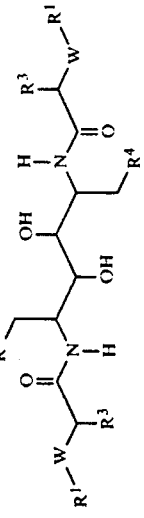 | 2-butyl | Ph | 0.082 | 2.8 | (765.45) | 4A |

TABLE I-continued

Structure:
$$R^1-W-\underset{R^3}{CH}-\underset{O}{C}(=O)-NH-\underset{R^4}{CH}-CH(OH)-CH(OH)-\underset{R^4}{CH}-NH-C(=O)-\underset{R^3}{CH}-W-R^1$$

| EXAMPLE | R¹W | R³ | R⁴ | IC₅₀ GAG mg/ml | IC₉₀ CELLS mg/ml | MP PHYSICAL DATA | METHOD |
|---------|-----|-----|-----|----------------|------------------|-------------------|--------|
| 31 | phenyl-CH₂-C(=O)-N-H | 2-butyl | Ph | 0.03 | 2.9 | 256-260 | 4A |
| 32 | (CH₃)₃C-C(=O)-N-H | 2-butyl | Ph | >9 | >30 | NMR | 4A |
| 33 | pyridyl-CH₂-C(=O)-N-H | 2-methylpropane | Ph | >9 | >30 | 179-182 | 4A |
| 34 | cyclohexyl-CH₂-C(=O)-N-H | 2-butyl | Ph | >9 | >30 | (775.51) | 4A |
| 35 | phenyl-CH₂-C(=O)-N-H | 2-butyl | Ph | 0.019 | 0.3 | 247-250 | 4F |
| 36 | (4-HO-phenyl)-CH₂-C(=O)-N-H | 2-butyl | Ph | 0.085 | 0.95 | NMR | 4A |
| 37 | phenyl-CH₂O-C(=O)-N-H | 2-butyl | Ph | 0.024 | 0.15 | NMR | 4D |

TABLE I-continued

[Structure: R¹-W-CHR³-C(O)-NH-CH(CH₂R⁴)-CH(OH)-CH(OH)-CH(CH₂R⁴)-NH-C(O)-CHR³-W-R¹]

| EXAMPLE | R¹-W | R³ | R⁴ | IC₅₀ GAG mg/ml | IC₉₀ CELLS mg/ml | MP PHYSICAL DATA | METHOD |
|---------|------|-----|-----|----------------|------------------|------------------|--------|
| 38 | biotinyl-(CH₂)₄-C(O)-NH- | 2-butyl | Ph | 0.055 | >30 | NMR | 4D |
| 39 | H₂N— (t-BOC-NH-CH(CH₂Ph)-C(O)-NH-) | 2-butyl | Ph | 0.937 | 10 | 184–190 | 4D;3 |
| 40 | (4-pyridyl-CH₂-C(O)-NH-) | 2-butyl | Ph | 0.03 | 2.2 | 228–232 | 4D |
| 41 | (Ph-CH₂-C(O)-NH-) | 2-butyl | Ph | 0.21 | 2.8 | NMR | 4A |
| 42 | (Ph-CH₂-O-C(O)-NH-) | 2-propyl | Ph | 0.025 | 0.05 | 216–221 | 4D |

TABLE I-continued

| EXAMPLE | R¹W | R³ | R⁴ | IC₅₀ GAG mg/ml | IC₉₀ CELLS mg/ml | MP PHYSICAL DATA | METHOD |
|---|---|---|---|---|---|---|---|
| 43 | CBZ-NH-CH(CH₂Ph)-C(O)-NH- | 2-butyl | Ph | 0.055 | 0.11 | 263–266 | 4D |
| 44 | CBZ-NH-CH(CH₂Ph)-C(O)-NH- | 2-butyl | Ph | 0.028 | 0.09 | 200–206 | 4A without HOBT |
| 45 | morpholine-C(O)-NH- | 2-butyl | Ph | 1.24 | 8.9 | 141–144 | 4F |
| 46 | PhCH₂O-C(O)-NH- | H₂N-C(O)-CH₂CH₂- | Ph | 0.245 | >30 | 241–244 | 4E |
| 47 | PhCH₂O-C(O)-NH- | H₂N-C(O)-(CH₂)₄- | Ph | 1.12 | >30 | 264–267 | 4E |

TABLE I-continued
| EXAMPLE | R¹-W | R³ | R⁴ | $IC_{50}$ GAG mg/ml | $IC_{90}$ CELLS mg/ml | MP PHYSICAL DATA | METHOD |
|---|---|---|---|---|---|---|---|
| 48 | 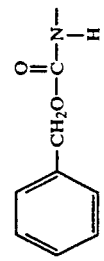 | 2-propyl | 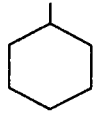 | >9 | >30 | 160-164 | 1B,4D |
| 49 | 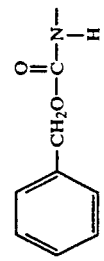 | 2-propyl | Ph | 0.036 | 0.2 | 217-220 | 4A |
| 50 | 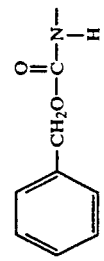 | 2-propyl | Ph | 0.01 | 0.6 | 194-197 | 4F |
| 51 | 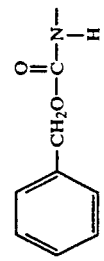 | 2-butyl | Ph | 0.019 | >30 | 257-260 | 4A |
| 52 | 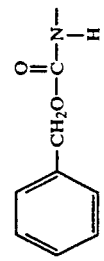 | 2-butyl | Ph | 0.004 | 2.7 | 226-230 | 4F |

TABLE I-continued

| EXAMPLE | R¹-W | R³ | R⁴ | IC$_{50}$ GAG mg/ml | IC$_{90}$ CELLS mg/ml | MP PHYSICAL DATA | METHOD |
|---|---|---|---|---|---|---|---|
| 53 | PhCH₂O-C(=O)-NH- | CH₃-CH(OH)- | Ph | 0.2 | 2.6 | NMR | 4C |
| 54 | PhCH₂O-C(=O)-NH- | 2-butyl | 4-Cl-Ph | 3.4 | 5.0 | 130–134 | 2C |
| 55 | PhCH₂O-C(=O)-NH- | CH₃-CH(OH)- | Ph | >9 | >30 | >250 | 4C |
| 56 | (CH₃)OCO—NHCHCONH—(CH₂Ph) | 2-butyl | Ph | 0.03 | 2.2 | 228–232 | 4D |
| 57 | CH₃-C(=O)-NH- | 2-propyl | Ph | 0.044 | 8.9 | >250 sinters at 220 | 4C |
| 58 | Fmoc-NH- | 2-propyl | Ph | 0.31 | >30 | 198–199 | 4C |

TABLE I-continued

| EXAMPLE | R¹-W | R³ | R⁴ | IC$_{50}$ GAG mg/ml | IC$_{90}$ CELLS mg/ml | MP PHYSICAL DATA | METHOD |
|---|---|---|---|---|---|---|---|
| 59 | CH₃—C(O)—N(H)— | H₂C=CHCH₂— | Ph | 0.58 | >30 | 119-123 | 4C |
| 60 | CH₃—C(O)—N(H)— | CH₃—S—CH₂CH₂— | Ph | 0.82 | >30 | 229-236 | 4C |
| 61 | H₂N-CH(CH₂Ph)-C(O)-N(H)- | 2-propyl | Ph | 0.04 | 2.9 | 212-216 | 4D;3 |
| 62 | CBZ-N(H)-CH(CH₂Ph)-C(O)-N(H)- | 2-propyl | Ph | 0.05 | — | >245 | 4D |
| 63 | H₂N— | 2-propyl | Ph | >9 | | 215-216 | |
| 64 | CF₃-S(O)(O)-N(H)- | 2-propyl | Ph | | >30 | | 2C |

TABLE I-continued

| EXAMPLE | R¹-W | R³ | R⁴ | IC₅₀ GAG mg/ml | IC₉₀ CELLS mg/ml | MP PHYSICAL DATA | METHOD |
|---|---|---|---|---|---|---|---|
| 65 | PhCH₂O-C(O)-NH- | 2-butyl | Ph | >10.4 | >30 | 147-151 | 4A |
| 66 | PhCH₂O-C(O)-NH- | 2-propyl | Ph | | | 235-238 | 4A |
| 67 | PhCH₂O-C(O)-NH- | 2-propyl | Ph | | | 288-292 | 4F |
| 68 | PhCH₂O-C(O)-NH- | 2-propyl | N-piperidinyl | >9 | >30 | 190-192 | 4F |
| 69 | PhCH₂-CH(NH₂)-C(O)-NH- | 2-butyl | Ph | 0.065 | — | 212-215 | 4D;3 |
| 70 | H₂N-C(O)-NH- | 2-propyl | Ph | | | | 4E |

TABLE I-continued

| EXAMPLE | R¹-W | R³ | R⁴ | IC$_{50}$ GAG mg/ml | IC$_{90}$ CELLS mg/ml | MP PHYSICAL DATA | METHOD |
|---|---|---|---|---|---|---|---|
| 71 | 1-adamantyl-CH(OH)-CH$_2$NH– | 2-propyl | Ph | >11 | >30 | (855.63) | 4G |
| 72 | Ph-CH(OH)-CH$_2$NH– | 2-propyl | Ph | >9.2 | >30 | (739.37) | 4G |
| 73 | Cbz-NH-CH(CH$_2$Ph)-CH$_2$-P(O)(OCH$_3$)(CH$_3$)– | methyl | Ph | 1.62 | >30 | (1071.6) | 4B |
| 74 | 2-(Boc-NH)-C$_6$H$_4$-C(O)NH– | 2-propyl | Ph | 3.72 | | (937.55) | 4B |
| 75 | 2-(H$_2$N)-C$_6$H$_4$-C(O)NH– | 2-propyl | Ph | 1.22 | | (NMR) | 4B |

TABLE I-continued

| EXAMPLE | R¹·W | R³ | R⁴ | IC$_{50}$ GAG mg/ml | IC$_{90}$ CELLS mg/ml | MP PHYSICAL DATA | METHOD |
|---|---|---|---|---|---|---|---|
| 76 | Boc-NH-C₆H₄-C(O)-NH- | 2-propyl | Ph | 0.296 | >30 | (937.71) | 4B |
| 77 | H₂N-C₆H₄-C(O)-NH- | 2-propyl | Ph | 0.15 | | (737.55) | 4B |
| 78 | Boc-NH-(CH₂)₃-C(O)-NH- | 2-propyl | Ph | 0.061 | | (869.67) | 4B |
| 79 | H₂N-(CH₂)₃-C(O)-NH- | 2-propyl | Ph | 0.185 | | (669.60) | 4B |
| 80 | Boc-thiazolidinyl-C(O)-NH- | 2-propyl | Ph | 13 | >30 | (929.64) | 4B |

TABLE I-continued

| EXAMPLE | R¹·W | R³ | R⁴ | IC₅₀ GAG mg/ml | IC₉₀ CELLS mg/ml | MP PHYSICAL DATA | METHOD |
|---|---|---|---|---|---|---|---|
| 81 | thiazolidine-carboxamide | 2-propyl | Ph | 0.201 | >30 | (729.59) | 4B |
| 82 | CBZ-NH-(CH₂)ₙ-C(O)NH- | 2-propyl | Ph | 0.625 | >30 | (993.81) | 4B |
| 83 | H₂N-(CH₂)ₙ-C(O)NH- | 2-propyl | Ph | 0.317 | >30 | (725.66) | 4B |
| 84 | CH₂O-C(O)NH- (benzyloxycarbonyl) | CH₃ | Ph | 0.151 | >30 | 236-237 | 2C |
| 85 | asparaginyl | 2-propyl | Ph | 0.007 | >30 | 229-233 | 4D;3 |
| 86 | glycyl | 2-propyl | Ph | 0.3 | >30 | 162-168 sinters at 94 | 4D;3 |

TABLE I-continued

| EXAMPLE | R¹-W | R³ | R⁴ | IC₅₀ GAG mg/ml | IC₉₀ CELLS mg/ml | MP PHYSICAL DATA | METHOD |
|---|---|---|---|---|---|---|---|
| 87 | H₂N-CH(C(O)NH₂)-(CH₂)₂-C(O)-NH- | 2-propyl | Ph | 3.3 | >30 | M.P.>245 sinters 120-130 | 4D;3 |
| 88 | CH₃-S(O)₂-CH₂-CH₂-O-C(O)-NH- | 2-butyl | Ph | 0.039 | 8.5 | 222-225 | 4C |
| 89 | CBZ-NH-CH(C(O)NH₂-CH₂)-C(O)-NH- | 2-propyl | Ph | 0.04 | >30 | M.P.>245 | 4E |
| 90 | CBZ-NH-CH(CH₂-C(O)NH₂)-C(O)-NH- | 2-propyl | Ph | 0.67 | 30 | M.P.>245 | 4E |
| 91 | CBZ-NH-CH₂-C(O)-NH- | 2-propyl | Ph | 0.042 | 0.2 | 239-241 | 4E |

TABLE I-continued

| EXAMPLE | R¹-W | R³ | R⁴ | IC₅₀ GAG mg/ml | IC₉₀ CELLS mg/ml | MP PHYSICAL DATA | METHOD |
|---|---|---|---|---|---|---|---|
| 92 | CBZ-NH-CH(CH₂CH₂CONH₂)-C(O)-NH- | 2-propyl | Ph | 0.08 | >30 | >245 | 4E |
| 93 | CBZ-NH-CH(iPr)-C(O)-NH- | 2-propyl | Ph | 0.099 | 1.0 | 237-238 | 4D |
| 94 | PhCH₂O-C(O)-NH- | 2-propyl | PhCH₂O-C₆H₄- | 0.123 | >30 | (979.2) | 2C |
| 95 | (CH₃)₃C-O-C(O)-NH- | 2-propyl | Ph | 12.5 | >30 | 209 | 4A |
| 96 | Ph-CH₂CH₂-C(O)-NH- | 2-propyl | Ph | 0.100 | 0.7 | 274 | 4A |

TABLE I-continued

| EXAMPLE | R¹-W | R³ | R⁴ | $IC_{50}$ GAG mg/ml | $IC_{90}$ CELLS mg/ml | MP PHYSICAL DATA | METHOD |
|---|---|---|---|---|---|---|---|
| 97 | 4-hydroxyphenyl-CH₂CH₂-C(=O)-NH- | 2-propyl | Ph | 0.250 | 0.9 | 168-170 | 4A |
| 98 | thiophen-2-yl-CH₂CH₂-C(=O)-NH- | 2-propyl | Ph | 0.050 | 0.3 | 247 | 4A |

Physical Data indicates melting point range; parentheticals indicate parent ion of mass spec; NMR indicates compound gave satisfactory nmr.
Method indicates method of preparation as described above under Examples 24-98.
indicates that the diol is protected as an acetonide.
indicates that this compound is a stereoisomer of the compound of Example 20.

Tables II to XVI include additional preferred embodiments of the invention. However, these embodiments are not exemplified herein.

TABLE II

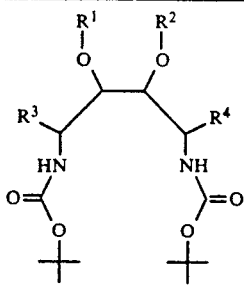

| EX NO. | $R^1$ | $R^2$ | $R^3$ | $R^4$ |
|---|---|---|---|---|
| 99 | $CH_3C(=O)$ | $CH_3C(=O)$ | $PhCH_2$ | $PhCH_2$ |
| 100 | $CH_3C(=O)$ | $CH_3C(=O)$ | $4\text{-}HO\text{-}C_6H_4CH_2$ | $4\text{-}HO\text{-}C_6H_4CH_2$ |
| 101 | $CH_3C(=O)$ | $CH_3C(=O)$ | 3,4-dichloro-benzyl | $PhCH_2$ |
| 102 | $CH_3C(=O)$ | $CH_3C(=O)$ | $CH_3SCH_2$ | $CH_3SCH_2$ |
| 103 | $CH_3C(=O)$ | $CH_3C(=O)$ | $CH_3SCH_2$ | $PhCH_2$ |
| 104 | $CH_3C(=O)$ | $CH_3C(=O)$ | $(CH_3)_2CHCH_2$ | $(CH_3)_2CHCH_2$ |
| 105 | $CH_3C(=O)$ | $CH_3C(=O)$ | 3-indolyl | 3-indolyl |
| 106 | $CH_3C(=O)$ | $CH_3C(=O)$ | $CH_3OC(=O)(CH_2)_5$ | $CH_3OC(=O)(CH_2)_5$ |
| 107 | $CH_3C(=O)$ | $CH_3C(=O)$ | $(CH_3)_2N(CH_2)_3$ | $(CH_3)_2N(CH_2)_3$ |
| 108 | $CH_3(CH_2)NHC(=O)$ | $CH_3(CH_2)NHC(=O)$ | $PhCH_2$ | $PhCH_2$ |
| 109 | $PhNHC(=O)$ | $PhNHC(=O)$ | $PhCH_2$ | $PhCH_2$ |
| 110 | $PhC(=O)$ | $PhC(=O)$ | $PhCH_2$ | $PhCH_2$ |
| 111 | $4\text{-}Cl\text{-}C_6H_4C(=O)$ | $4\text{-}Cl\text{-}C_6H_4C(=O)$ | $PhCH_2$ | $PhCH_2$ |
| 112 | $3\text{-}Me\text{-}C_6H_4C(=O)$ | $CH_3C(=O)$ | $PhCH_2$ | $PhCH_2$ |
| 113 | $PhCH_2OC(=O)$ | $PhCH_2OC(=O)$ | $PhCH_2$ | $PhCH_2$ |

TABLE III

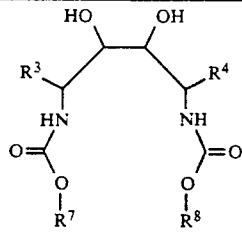

| Ex. No. | $R^7$ | $R^8$ | $R^3$ | $R^4$ |
|---|---|---|---|---|
| 114 | $(CH_3)_3C$ | $(CH_3)_3C$ | $PhCH_2$ | $PhCH_2$ |
| 115 | $(CH_3)_3C$ | $(CH_3)_3C$ | 4-($SO_2NH_2$)-benzyl | 4-($SO_2NH_2$)-benzyl |
| 116 | $(CH_3)_3C$ | $(CH_3)_3C$ | $4\text{-}HO\text{-}C_6H_4CH_2$ | $4\text{-}HO\text{-}C_6H_4CH_2$ |
| 117 | $(CH_3)_3C$ | $(CH_3)_3C$ | 4-($SO_2NH_2$)-benzyl | $PhCH_2$ |
| 118 | $(CH_3)_3C$ | $(CH_3)_3C$ | 4-cyanobenzyl | 4-cyanobenzyl |
| 119 | $(CH_3)_3C$ | $(CH_3)_3C$ | 2-nitrobenzyl | $PhCH_2$ |
| 120 | $(CH_3)_3C$ | $(CH_3)_3C$ | $CF_3CH_2$ | $CF_3CH_2$ |
| 121 | $(CH_3)_3C$ | $(CH_3)_3C$ | $CH_3(CH_2)_6$ | $CH_3(CH_2)_6$ |
| 122 | $(CH_3)_3C$ | $(CH_3)_3C$ | $(CH_3)_2C=CHCH_2$ | $(CH_3)_2C=CHCH_2$ |

TABLE III-continued

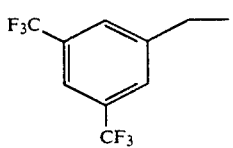

| Ex. No. | R⁷ | R⁸ | R³ | R⁴ |
|---|---|---|---|---|
| 123 | (CH₃)₃C | (CH₃)₃C | CH₂=CHCH₂ | CH₂=CHCH₂ |
| 124 | (CH₃)₃C | (CH₃)₃C | CH₃O₂C(CH₂)₄ | CH₃O₂C(CH₂)₄ |
| 125 | (CH₃)₃C | (CH₃)₃C | 2-naphthyl | 2-naphthyl |
| 126 | | | 122(naphthylmethyl) | 123(naphthylmethyl) |
| 127 | (CH₃)₃C | (CH₃)₃C | 1-naphthyl | 1-naphthyl |
| 128 | (CH₃)₃C | (CH₃)₃C | cyclohexylmethyl | cyclohexylmethyl |
| 129 | (CH₃)₃C | (CH₃)₃C | 1-naphthyl | 3,4-dichlorobenzyl |
| 130 | (CH₃)₃C | (CH₃)₃C | 2-(pyridylmethyl) | 2-(pyridylmethyl) |
| 131 | (CH₃)₃C | (CH₃)₃C | 3-(pyridylmethyl) | 3-(pyridylmethyl) |
| 132 | (CH₃)₃C | (CH₃)₃C | 4-(pyridylmethyl) | 4-(pyridylmethyl) |
| 133 | (CH₃)₃C | (CH₃)₃C | 4-pyridazylmethyl | 4-pyridazylmethyl |
| 134 | (CH₃)₃C | (CH₃)₃C | 4-(imidazolylmethyl) | 4-(imidazolylmethyl) |
| 135 | PhCH₂ | PhCH₂ | PhCH₂ | PhCH₂ |
| 136 | PhCH₂ | PhCH₂ | 4-HO—C₆H₄CH₂ | 4-HO—C₆H₄CH₂ |
| 137 | PhCH₂ | PhCH₂ | CH₃SCH₂ | CH₃SCH₂ |
| 138 | PhCH₂ | PhCH₂ | 2-thiophenyl | 2-thiophenyl |
| 139 | PhCH₂ | PhCH₂ | HS(CH₂)₄ | HS(CH₂)₄ |
| 140 | PhCH₂ | PhCH₂ | 4-(benzyloxy)benzyl | 4-(benzyloxy)benzyl |
| 141 | PhCH₂ | PhCH₂ | 3-(methane-sulfonyl)benzyl | 3-(methane-sulfonyl)benzyl |
| 142 | PhCH₂ | PhCH₂ | 3,4-methylene-dioxybenzyl | 3,4-methylene-dioxybenzyl |
| 143 | PhCH₂ | PhCH₂ | 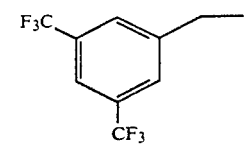 | 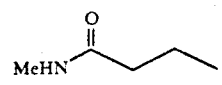 |
| 144 | PhCH₂ | PhCH₂ | CH₃NHC(=O)CH₂CH₂ | 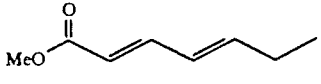 |
| 145 | PhCH₂ | PhCH₂ | cyclohexylmethyl | cyclohexylmethyl |
| 146 | PhCH₂ | PhCH₂ | cyclopropylmethyl | cyclopropylmethyl |
| 147 | PhCH₂ | PhCH₂ | 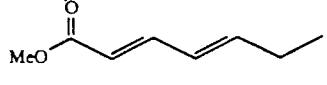 | |
| 148 | (4-CF₃)C₆H₄CH₂ | (4-CF₃)C₆H₄CH₂ | PhCH₂ | PhCH₂ |
| 149 | 2-C₅H₅NCH₂ | 2-C₅H₅NCH₂ | PhCH₂ | PhCH₂ |
| 150 | 4-[(CH₃)₃C]C₆H₄CH₂ | 4-[(CH₃)₃C]C₆H₄CH₂ | PhCH₂ | PhCH₂ |
| 151 | (CH₃)₂C=CHCH₂ | (CH₃)₂C=CHCH₂ | PhCH₂ | PhCH₂ |
| 152 | 4-[SO₂NH₂]C₆H₄CH₂ | 4-[SO₂NH₂]C₆H₄CH₂ | PhCH₂ | PhCH₂ |
| 153 | PhCH₂ | PhCH₂ | CH₃CH₂CH₂ | CH₃CH₂CH₂ |
| 154 | (CH₃)₃C | (CH₃)₃C | CH₃CH₂CH₂ | CH₃CH₂CH₂ |
| 155 | 4-[SO₂NH₂]C₆H₄CH₂ | 4-[SO₂NH₂]C₆H₄CH₂ | CH₃CH₂CH₂ | CH₃CH₂CH₂ |

TABLE IV

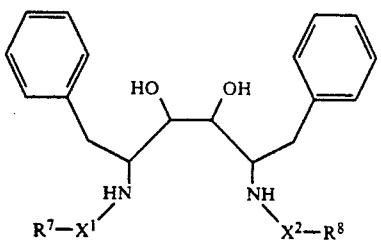

| EX. NO. | R⁷—X¹ | R⁸=X² |
|---|---|---|
| 156 | PhC(=O) | PhC(=O) |
| 157 | (CH₃)₃CC(=O) | (CH₃)₃CC(=O) |
| 158 | 2-pyridylcarbonyl | 2-pyridylcarbonyl |
| 159 | H—Val—Val | Val—Val—OH |
| 160 | H—Ser—Ala—Ala | Val—Val—OH |
| 161 | Boc—Ser—Ala—Ala | Val—Val—OMe |
| 162 | H—Ala—Ala | Val—Val—OMe |
| 163 | H—Val—Ser—Gln—Asn | Ile—Val—OH |
| 164 | Ac—Leu—Val | Val—Leu—OMe |
| 165 | Ac—Lys—Val | Val—Lys—Ac |
| 166 | Val—Boc—Val—Val | Arg—Val—OMe |
| 167 | H—Arg—Gly—Val | Val—Gly—Arg—OH |
| 168 | cyclohexylcarbonyl | cyclohexylcarbonyl |
| 169 | PhC(=O) | CH₃(C=O) |
| 170 | PhNHC(=O) | PhNH(C=O) |
| 171 | PhCH₂NHC(=O) | PhCH₂NHC(=O) |
| 172 | 4-Br—C₆H₄CH(CH₃)NHC(=O) | 4-Br—C₆H₄CH(CH₃)NHC(=O) |
| 173 | Ph(C=S) | Ph(C=S) |
| 174 | CH₃ | CH₃ |
| 175 | PhSO₂ | PhSO₂ |
| 176 | 2-pyridylmethylaminocarbonyl | 2-pyridylmethylaminocarbonyl |
| 177 | 2-pyridylacetyl-Asn | 2-pyridylacetyl-Asn |
| 178 | 2-pyridylacetyl-Val | 2-pyridylacetyl-Asn |
| 179 | 2-pyridylacetyl-Leu | 2-pyridylacetyl-Leu |
| 180 | 2-pyridylacetyl-Gln | 2-pyridylacetyl-Gln |
| 181 | phenylacetyl-Ile | phenylacetyl-Ile |
| 182 | phenylacetyl-Asn | phenylacetyl-Asn |
| 183 | phenylacetyl-Gln | phenylacetyl-Gln |
| 184 | phenylacetyl-Val | phenylacetyl-Val |
| 185 | phenylacetyl-Leu | phenylacetyl-Leu |
| 186 | quinoline-2-carbonyl-Asn | quinoline-2-carbonyl-Asn |
| 187 | qunioline-2-carbonyl-Gln | qunioline-2-carbonyl-Ile |
| 188 | quinoline-2-carbonyl-Ile | quinoline-2-carbonyl-Ile |
| 189 | quinoline-2-carbonyl-Leu | quinoline-2-carbonyl-Val |
| 190 | 2-pipecolinyl-Ile | 2-pipecolinyl-Asn |
| 191 | 2-pipecolinyl-Asn | 2-pipecolinyl-Asn |
| 192 | 2-pipecolinyl-Ile | 2-pipecolinyl-Ile |
| 193 | t-butylacetyl-Asn | t-butylacetyl-Asn |
| 194 | t-butylacetyl-Asn | t-butylacetyl-Ile |
| 195 | t-butylacetyl-Ile | t-butylacetyl-Ile |
| 196 | isoquinoline-3-formyl-Asn | isoquinoline-3-formyl-Asn |
| 197 | isoquinoline-3-formyl-Asn | isoquinoline-3-formyl-Ile |
| 198 | isoquinoline-3-formyl-Ile | isoquinoline-3-formyl-Ile |
| 199 | 2-naphthoyl-Asn | 2-naphthoyl-Asn |
| 200 | 2-naphthoyl-Gln | 2-naphthoyl-Ile |
| 201 | 2-naphthoyl-Ile | 2-naphthoyl-Ile |
| 202 | 2-naphthoyl-Ile | 2-naphthoyl-Asn |
| 203 | 2-naphthoyl-Val | 2-naphthoyl-Ile |
| 204 | cyclohexylacetyl-Asn | cyclohexylacetyl-Asn |
| 205 | cyclohexylacetyl-Ile | cyclohexylacetyl-Ile |
| 206 | cyclohexylacetyl-Asn | cyclohexylacetyl-Ile |

TABLE V

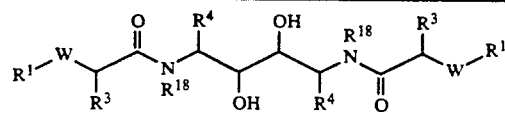

| Ex. No. | R¹ | W | R³ | R⁴ | R¹⁸ |
|---|---|---|---|---|---|
| 207 | 2-pyridylmethyl | A(=O) | 2-propyl | benzyl | H |
| 208 | 2-pyridylmethyl | B(=O) | 2-butyl | 4-imidazolylmethyl | H |
| 209 | benzyl | C(=O) | 2-butyl | cyclohexylmethyl | H |

TABLE V-continued $$R^1\text{-W-}\underset{R^3}{\text{CH}}-\underset{\substack{\|\\O}}{\text{C}}-\underset{R^{18}}{\text{N}}-\underset{R^4}{\text{CH}}-\underset{\text{OH}}{\text{CH}}-\underset{\text{OH}}{\text{CH}}-\underset{R^4}{\text{CH}}-\underset{R^{18}}{\text{N}}-\underset{\substack{\|\\O}}{\text{C}}-\underset{R^3}{\text{CH}}\text{-W-}R^1$$

| Ex. No. | R¹ | W | R³ | R⁴ | R¹⁸ |
|---|---|---|---|---|---|
| 210 | benzyl | D(=O) | 2-propyl | benzyl | H |
| 211 | benzyl | E(=O) | 2-propyl | benzyl | CH₃ |
| 213 | benzyl | F(=O) | benzyl | benzyl | H |
| 214 | n-propyl | G(=O) | 2-propyl | benzyl | H |
| 215 | naphthyl | H(=O) | 2-propyl | benzyl | H |
| 216 | phenyl | I(=O) | 2-propyl | benzyl | H |
| 217 | thiophenyl | J(=O) | 2-propyl | benzyl | H |
| 218 | trifluoromethyl | K(=O) | 2-propyl | benzyl | H |
| 219 | benzyl | L(=O)CH₂ | 2-propyl | benzyl | H |
| 220 | 2-pyridylmethyl | M(=O)NH | 2-butyl | benzyl | H |
| 221 | benzyl | N(=O)NH | 2-butyl | benzyl | H |
| 222 | benzyl | O(=O)NH | 2-butyl | benzyl | CH₃ |
| 223 | benzyl | P(=O)NH | 2-butyl | Q(-trifluoromethylbenzyl | H |
| 224 | benzyl | R(=O)NH | cyclobutyl | benzyl | H |
| 225 | benzyl | S(=O)NH | cyclobutylmethyl | benzyl | H |
| 226 | methyl | T(=O)NH | 2-butyl | benzyl | H |
| 227 | phenylethyl | U(=O)NH | 2-butyl | benzyl | H |
| 228 | benzyl | V(=O)NHNH | 2-propyl | benzyl | H |
| 229 | benzyl | W(=O)O | 2-propyl | benzyl | H |
| 230 | benzyl | X(=S) | 2-propyl | benzyl | H |
| 231 | benzyl | Y(=S)NH | 2-propyl | benzyl | H |
| 232 | benzyl | C(Cl)=N | 2-propyl | benzyl | H |
| 233 | 2-pyridylmethyl | C(NHMe)=N | 2-propyl | benzyl | H |
| 234 | 3-methylpropyl | C(NHMe)=N | 2-propyl | benzyl | H |
| 235 | benzyl | C(NHMe)=N | 2-propyl | benzyl | H |
| 236 | benzyl | C(NHMe)=N | 2-propyl | benzyl | CH₃ |
| 237 | benzyl | C(NHMe)=N | 2-propyl | Z((HCF₂O)C₆H₄CH₂ | |
| 238 | 2-pyridylethyl | C(OCH₂CH₃)=N | 2-propyl | benzyl | H |
| 239 | 3-naphthylmethyl | C(OCH₂CH₃)=N | 2-propyl | benzyl | H |
| 240 | AA(-t-butylbenzyl | C(OCH₂CH₃)=N | 2-propyl | benzyl | H |
| 241 | benzyl | C(OCH₂CH₃)=N | 2-propyl | benzyl | H |
| 242 | benzyl | C(OCH₂CH₃)=N | 2-propyl | BB(-ytrifluoromethylbenzyl | H |
| 243 | benzyl | C(OCH₂CH₃)=N | 2-propyl | CC(-chlorobenzyl | H |
| 244 | benzyl | C(OCH₂CH₃)=N | 2-propyl | cyclohexylmethyl | H |
| 245 | benzyl | C(OCH₂CH₃)=N | cyclobutyl | benzyl | H |
| 246 | benzyl | C(OCH₂CH₃)=N | cyclobutylmethyl | benzyl | H |
| 247 | benzyl | C(OCH₂CH₃)=N | cyclopropyl | benzyl | H |
| 248 | benzyl | C(OCH₃)=N | 2-propyl | benzyl | H |
| 249 | benzyl | CH₂OCH₂ | 2-propyl | benzyl | H |
| 250 | benzyl | CH₂CH₂ | 2-propyl | benzyl | H |
| 251 | benzyl | CH₂CHOH | 2-propyl | benzyl | H |
| 252 | benzyl | CH₂O | 2-propyl | benzyl | H |
| 253 | benzyl | CH₂OH | 2-propyl | benzyl | H |
| 254 | benzyl | CH=CH | 2-propyl | benzyl | H |
| 255 | benzyl | CHOHCH₂ | 2-propyl | benzyl | H |
| 256 | benzyl | CHOHCHOH | 2-propyl | benzyl | H |
| 257 | benzyl | HNC(=S)NH | 2-propyl | benzyl | H |
| 258 | benzyl | HNSO₂ | 2-butyl | benzyl | H |
| 259 | benzyl | HNSO₂NH | 2-butyl | benzyl | H |
| 260 | benzyl | DD( | 2-propyl | benzyl | H |
| 261 | benzyl | NH—NH | 2-propyl | benzyl | H |
| 262 | (—CH₂CH₂CH₂CH₂CH₂—) | NHC(=O)NH | 2-butyl | benzyl | H |
| 263 | (—CH₂CH₂OCH₂CH₂—) | NHC(=O)NH | 2-butyl | benzyl | H |
| 264 | 2-hydroxy-3,3-dimethylpropyl | NHC(=O)NH | 2-butyl | benzyl | H |
| 265 | 2-hydroxy-3,3-dimethylpropyl | NHC(=O)NH | 2-butyl | benzyl | CH₃ |
| 266 | 2-hydroxyindanylmethyl | NHC(=O)NH | 2-butyl | benzyl | H |
| 267 | 3,5-dimethoxyphenyl | NHC(=O)NH | 2-butyl | benzyl | H |
| 268 | 3-hydroxy-n-propyl | NHC(=O)NH | 2-butyl | benzyl | H |
| 269 | 270-nitrobenzyl | NHC(=O)NH | 2-butyl | benzyl | H |
| 271 | 4-benzyloxyphenylmethyl | NHC(=O)NH | 2-butyl | benzyl | H |
| 272 | 4-cyano-n-butyl | NHC(=O)NH | 2-butyl | benzyl | H |
| 273 | 4-phenoxyphenylmethyl | NHC(=O)NH | 2-butyl | benzyl | H |
| 274 | 4-t-butylphenylmethyl | NHC(=O)NH | 2-butyl | benzyl | H |
| 275 | adamantyl | NHC(=O)NH | 2-butyl | benzyl | H |
| 276 | benzyl | NHC(=O)NH | 2-butyl | benzyl | H |
| 277 | benzyl | NHC(=O)NH | 2-butyl | benzyl | CH₃ |
| 278 | benzyl | NHC(=O)NH | 2-propyl | benzyl | H |
| 279 | benzyl | NHC(=O)NH | 2-propyl | 2-naphthylmethyl | H |
| 280 | benzyl | NHC(=O)NH | 2-propyl | 3-naphthylmethyl | H |
| 281 | benzyl | NHC(=O)NH | 2-propyl | 1-adamantylmethul | H |
| 282 | benzyl | NHC(=O)NH | 2-propyl | FF(-hydroxybenzyl | H |
| 283 | benzyl | NHC(=O)NH | 2-propyl | 2-imidazolylethyl | H |
| 284 | benzyl | NHC(=O)NH | 2-propyl | 4-pyridinylmethyl | H |

TABLE V-continued

| Ex. No. | R¹ | W | R³ | R⁴ | R¹⁸ |
|---|---|---|---|---|---|
| 285 | benzyl | NHC(=O)NH | 2-propyl | 4-bromophenyl | H |
| 286 | benzyl | NHC(=O)NH | 2-propyl | cycloheptylmethyl | H |
| 287 | benzyl | NHC(=O)NH | 2-propyl | 2-thiophenylmethyl | H |
| 288 | benzyl | NHC(=O)NH | 2-propyl | 3-pyrrazolylmethyl | H |
| 289 | benzyl | NHC(=O)NH | 2-propyl | GG((trifluoromethane-sulfonyl)propyl | H |
| 290 | benzyl | NHC(=O)NH | 2-propyl | HH((1-methyl)piperidinylmethyl | H |
| 291 | benzyl | NHC(=O)NH | 2-thiazolylmethyl | benzyl | H |
| 292 | benzyl | NHC(=O)NH | benzyl | benzyl | H |
| 293 | benzyl | NHC(=O)NH | $CH_2CF_3$ | benzyl | H |
| 294 | benzyl | NHC(=O)NH | $CH_2CH_2C(=O)NH_2$ | benzyl | H |
| 295 | benzyl | NHC(=O)NH | $CH_2CH_2OH$ | benzyl | H |
| 296 | benzyl | NHC(=O)NH | $CH_2CHOHCH_3$ | benzyl | H |
| 297 | benzyl | NHC(=O)NH | cyclobutyl | benzyl | H |
| 298 | benzyl | NHC(=O)NH | cyclobutyl | benzyl | $CH_3$ |
| 299 | benzyl | NHC(=O)NH | cyclobutylmethyl | benzyl | H |
| 300 | benzyl | NHC(=O)NH | cyclopentylmethyl | benzyl | H |
| 301 | benzyl | NHC(=O)NH | cyclopropyl | benzyl | H |
| 302 | benzyl | NHC(=O)NH | cyclopropylmethyl | benzyl | H |
| 303 | cis-2-decahydronaphthylmethyl | NHC(=O)NH | 2-butyl | benzyl | H |
| 304 | cis-2-decahydronaphthylmethyl | NHC(=O)NH | 2-butyl | benzyl | $CH_3$ |
| 305 | benzyl | O | 2-propyl | benzyl | H |
| 306 | $(CH_2CH_2CH)CH_2CH_2$ | OC(=O)NH | 2-butyl | benzyl | H |
| 307 | 1-piperidylethyl | OC(=O)NH | 2-butyl | benzyl | H |
| 308 | 2-benzimidazolylmethyl | OC(=O)NH | 2-butyl | benzyl | H |
| 309 | 2-naphthylmethyl | OC(=O)NH | 2-butyl | benzyl | H |
| 310 | 2-pyridylmethyl | OC(=O)NH | 2-butyl | benzyl | H |
| 311 | 2-quinazolinylmethyl | OC(=O)NH | 2-butyl | benzyl | H |
| 312 | 3,4-methylene-dioxyphenylmethyl | OC(=O)NH | 2-butyl | benzyl | H |
| 313 | 3-chlorobenzyl | OC(=O)NH | 2-butyl | benzyl | H |
| 314 | 3-phenylpropyl | OC(=O)NH | 2-butyl | benyzl | H |
| 315 | II(-acetamidobenzyl | OC(=O)NH | 2-butyl | benzyl | H |
| 316 | 4-imidazolylmethyl | OC(=O)NH | 2-butyl | benzyl | H |
| 317 | 4-methanesulfonylbenzyl | OC(=O)NH | 2-butyl | benzyl | H |
| 318 | 4-methoxybenzyl | OC(=O)NH | 2-butyl | benzyl | H |
| 319 | 4-pyridylmethyl | OC(=O)NH | 2-butyl | benzyl | H |
| 320 | 4-trifluoromethylbenzyl | OC(=O)NH | 2-butyl | benzyl | H |
| 321 | 9-fluorenylmethyl | OC(=O)NH | 2-butyl | benzyl | H |
| 322 | adamantylmethyl | OC(=O)NH | 2-butyl | benzyl | H |
| 323 | benzyl | OC(=O)NH | 1-methoxy-2-propyl | benzyl | H |
| 324 | benzyl | OC(=O)NH | 325-hydroxycyclo-pentylmethyl | | |
| 326 | benzyl | OC(=O)NH | 2,2,2-tri-chloroethyl | benzyl | H |
| 327 | benzyl | OC(=O)NH | 2,2,2-tri-fluoroethyl | benzyl | H |
| 328 | benzyl | OC(=O)NH | 2-butyl | benzyl | H |
| 329 | benzyl | OC(=O)NH | 2-propyl | benzyl | H |
| 330 | benzyl | OC(=O)NH | 2-propyl | benzyl | $CH_3$ |
| 331 | benzyl | OC(=O)NH | 2-propyl | 3-naphthylmethyl | H |
| 332 | benzyl | OC(=O)NH | 2-propyl | KK(-phenoxybenzyl | H |
| 333 | benzyl | OC(=O)NH | 2-propyl | LL(-benzyloxybenzyl | H |
| 334 | benzyl | OC(=O)NH | 2-propyl | MM(-(5-tetrazolyl)benzyl | H |
| 335 | benzyl | OC(=O)NH | 2-propyl | NN(,5'-bis(trifluore-methyl)benzyl | H |
| 336 | benzyl | OC(=O)NH | 2-propyl | OO(-trifluoromethylbenzyl | H |
| 337 | benzyl | OC(=O)NH | 2-propyl | 2-phenylethyl | H |
| 338 | benzyl | OC(=O)NH | 2-propyl | 2-benzimidazolylmethyl | H |
| 339 | benzyl | OC(=O)NH | 2-propyl | PP((4-chlorophenyl)ethyl | H |
| 340 | benzyl | OC(=O)NH | 2-propyl | 2-decahydronaphthylmethyl | H |
| 341 | benzyl | OC(=O)NH | 2-propyl | QQ((3,4-methylene-dioxyphenyl)ethyl | H |
| 342 | benzyl | OC(=O)NH | RR((dimethylamino)-1-propyl | benzyl | H |
| 343 | benzyl | OC(=O)NH | benzyl | benzyl | H |
| 344 | benzyl | OC(=O)NH | $CH_2NHC(=O)NHCH_3$ | 4-pyridylmethyl | H |
| 345 | benzyl | OC(=O)NH | $CH_2NHSO_2CH_3$ | benzyl | H |
| 346 | benzyl | OC(=O)NH | cyclobutyl | benzyl | H |
| 347 | benzyl | OC(=O)NH | cyclobutylmethyl | benzyl | H |
| 348 | benzyl | OC(=O)NH | cyclopropyl | 2-pyridylmethyl | H |
| 349 | benzyl | OC(=O)NH | cyclopropylmethyl | benzyl | H |
| 350 | benzyl | OC(=O)NH | methyl | benzyl | H |
| 351 | $CH_3SO_2CH_2CH_2$ | OC(=O)NH | 2-butyl | benzyl | H |

TABLE V-continued

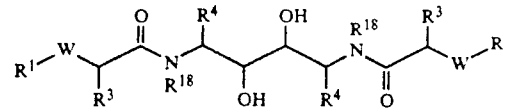

| Ex. No. | R¹ | W | R³ | R⁴ | R¹⁸ |
|---|---|---|---|---|---|
| 352 | cyclopentylethyl | OC(=O)NH | 2-butyl | 2-pyridylmethyl | H |
| 353 | F₂HCOC₆H₄CH₂ | OC(=O)NH | 2-butyl | 3-pyridylmethyl | H |
| 354 | N,N-dimethylamino-3-propyl | OC(=O)NH | 2-butyl | benzyl | H |
| 355 | benzyl | OCH₂ | 2-propyl | benzyl | H |
| 356 | benzyl | OP(=O)(OMe)O | 2-propyl | 2-pyridylmethyl | H |
| 357 | benzyl | SO₂ | 2-propyl | benzyl | H |
| 358 | 2,4-difluorophenyl | SO₂NH | 2-butyl | 2-pyridylmethyl | H |
| 359 | SS(-methylphenyl | SO₂NH | 2-butyl | benzyl | H |
| 360 | benzyl | SO₂NH | TT((methylamino)ethyl | benzyl | H |
| 361 | benzyl | SO₂NH | 2-furanylmethyl | benzyl | H |
| 362 | benzyl | SO₂NH | 2-propyl | benzyl | H |
| 363 | benzyl | SO₂NH | 2-propyl | benzyl | Et |
| 364 | benzyl | SO₂NH | 2-propyl | UU(-trifluoromethylbenzyl | H |
| 365 | benzyl | SO₂NH | 2-propyl | VV(,4'-difluorobenzyl | H |
| 366 | benzyl | SO₂NH | 2-propyl | 3-phenylpropyl | H |
| 367 | benzyl | SO₂NH | 2-propyl | 1-pyrrolylethyl | H |
| 368 | benzyl | SO₂NH | 2-propyl | WW((4-chlorophenyl)ethyl | H |
| 369 | benzyl | SO₂NH | 2-propyl | 1-phenylethyl | H |
| 370 | benzyl | SO₂NH | 3-hydroxy-1-propyl | 1-phenylethyl | H |
| 371 | benzyl | SO₂NH | cyclobutyl | benzyl | H |
| 372 | benzyl | SO₂NH | cyclopropyl | benzyl | H |
| 373 | benzyl | SO₂NH | methylthiomethyl | 1-phenylethyl | H |
| 374 | cyclohexylethyl | SO₂NH | 2-butyl | 2-pyridylmethyl | H |
| 375 | nonafluorobutyl | SO₂NH | 2-butyl | benzyl | H |
| 376 | phenyl | SO₂NH | 2-butyl | 2-pyridylmethyl | H |
| 377 | trifluoromethyl | SO₂NH | 2-butyl | benzyl | H |
| 378 | 2,4-difluorophenyl | SO₂NHC(=O)NH | 2-butyl | benzyl | H |
| 379 | XX(-methylphenyl | SO₂NHC(=O)NH | YY((dimethyl-amino)ethyl | 3-pyridylmethyl | H |
| 380 | ZZ(-methylphenyl | SO₂NHC(=O)NH | 2-butyl | benzyl | H |
| 381 | AAA(-methylphenyl | SO₂NHC(=O)NH | 2-butyl | 4-pyridylmethyl | H |
| 382 | BBB(-methylphenyl | SO₂NHC(=O)NH | benzyl | benzyl | H |
| 383 | CCC(-methylphenyl | SO₂NHC(=O)NH | CH₂CH₂OH | benzyl | H |
| 384 | DDD(-methylphenyl | SO₂NHC(=O)NH | cyclobutyl | benzyl | H |
| 385 | EEE(-methylphenyl | SO₂NHC(=O)NH | cyclohexylmethyl | 4-pyridylmethyl | H |
| 386 | FFF(-methylphenyl | SO₂NHC(=O)NH | cyclopropyl | benzyl | H |
| 387 | benzyl | SO₂NHC(=O)NH | 2-butyl | benzyl | H |
| 388 | cyclohexylethyl | SO₂NHC(=O)NH | 2-butyl | 2-pyridylmethyl | H |
| 389 | methyl | SO₂NHC(=O)NH | 2-butyl | benzyl | H |
| 390 | nonafluorobutyl | SO₂NHC(=O)NH | 2-butyl | benzyl | H |
| 391 | phenyl | SO₂NHC(=O)NH | 2-butyl | 3-pyridylmethyl | H |
| 392 | phenyl | SO₂NHC(=O)NH | 2-butyl | benzyl | H |
| 393 | phenyl | SO₂NHC(=O)NH | 2-butyl | GGG(-chlorobenzyl | H |
| 394 | phenyl | SO₂NHC(=O)NH | 2-butyl | 3-naphthylmethyl | H |
| 395 | phenyl | SO₂NHC(=O)NH | 2-butyl | HHH((4-fluorophenyl)ethyl | H |
| 396 | phenyl | SO₂NHC(=O)NH | 2-butyl | 2-phenylethyl | H |
| 397 | phenyl | SO₂NHC(=O)NH | 2-butyl | III(-carbomethoxybenzyl | H |
| 398 | phenyl | SO₂NHC(=O)NH | 2-butyl | 2-pyridylmethyl | CH₃ |
| 399 | phenyl | SO₂NHC(=O)NH | cyclopropyl | benzyl | H |
| 400 | trifluoromethyl | SO₂NHC(=O)NH | 2-butyl | benzyl | H |
| 401 | trifluoromethyl | SO₂NHC(=O)NH | 2-butyl | benzyl | H |
| 402 | trifluoromethyl | SO₂NHC(=O)NH | cyclobutyl | 3-pyridylmethyl | H |
| 403 | trifluoromethyl | SO₂NHC(=O)NH | cyclopropyl | 4-pyridylmethyl | H |

TABLE VI

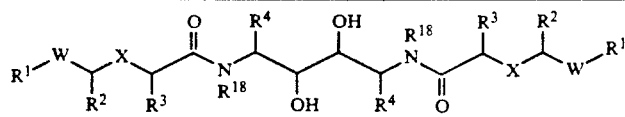

| Ex. No. | R¹ | W | X | R² | R³ | R⁴ | R¹⁸ |
|---|---|---|---|---|---|---|---|
| 404 | benzyl | C(=O)NH | C(=O)NH | benzyl | 2-butyl | benzyl | H |
| 405 | benzyl | C(=O)NH | C(=O)O | benzyl | 2-butyl | benzyl | H |
| 406 | benzyl | C(=O)NH | C(=O) | benzyl | 2-butyl | 2-pyridyl-methyl | H |
| 407 | benzyl | C(=O)NH | CH₂C(=O) | benzyl | 2-butyl | benzyl | H |
| 408 | benzyl | C(=O)NH | CH₂C(=O)CH₂ | benzyl | 2-butyl | 3-pyridyl-methyl | H |
| 409 | benzyl | C(=O)NH | C(=Q)CH₂ | benzyl | 2-butyl | benzyl | H |

TABLE VI-continued structure: R¹-CH(R²)(R³)-X-CH₂-C(=O)-N(R¹⁸)-CH(R⁴)-CH(OH)-CH(OH)-CH(R⁴)-N(R¹⁸)-C(=O)-CH(R³)(R²)-X-CH₂-W-R¹

| Ex. No. | R¹ | W | X | R² | R³ | R⁴ | R¹⁸ |
|---|---|---|---|---|---|---|---|
| 410 | benzyl | C(=O)NH | SO₂NH | benzyl | 2-butyl | benzyl | H |
| 411 | benzyl | C(=O)NH | SO₂ | benzyl | 2-butyl | 4-pyridyl-methyl | H |
| 412 | benzyl | C(=O)NH | CH₂OCH₂ | benzyl | 2-butyl | benzyl | H |
| 413 | benzyl | C(=O)NH | CH₂O | benzyl | 2-butyl | benzyl | H |
| 414 | benzyl | C(=O)NH | CH₂NCH₃ | benzyl | 2-butyl | 2-pyridyl-methyl | H |
| 415 | benzyl | C(=O)NH | CH₂NH | benzyl | 2-butyl | benzyl | H |
| 416 | benzyl | C(=O)NH | CH₂CH₂ | benzyl | 2-butyl | benzyl | H |
| 417 | benzyl | C(=O)NH | CH=CH | benzyl | 2-butyl | 3-pyridyl-methyl | H |
| 418 | benzyl | C(=O)NH | CH(OH)CH(OH) | benzyl | 2-butyl | benzyl | H |
| 419 | benzyl | C(=O)NH | CH(OH)CH₂ | benzyl | 2-butyl | benzyl | H |
| 420 | benzyl | C(=O)NH | CH₂CH(OH) | benzyl | 2-butyl | benzyl | H |
| 421 | benzyl | C(=O)NH | CH(OH) | benzyl | 2-butyl | benzyl | H |
| 422 | benzyl | C(=O)NH | C(—N[Me]2)=N | benzyl | 2-butyl | benzyl | H |
| 423 | benzyl | C(=O)NH | C(—OEt)=N | benzyl | 2-butyl | benzyl | H |
| 424 | benzyl | C(=O)NH | C(Cl—)=N | benzyl | 2-butyl | 2-pyridyl-methyl | H |
| 425 | benzyl | C(=O)NH | SO₂NH | benzyl | 2-butyl | benzyl | CH₃ |
| 426 | benzyl | NHC(=O)NH | C(=O)NH | benzyl | 2-butyl | benzyl | H |
| 427 | 2-pyridyl-methyl | NHC(=O)NH | C(=O)NH | benzyl | 2-butyl | 3-pyridyl-methyl | H |
| 428 | 2-pyrimidinyl | NHC(=O)NH | C(=O)NH | benzyl | 2-butyl | benzyl | H |
| 429 | benzyl | NHC(=O)NH | C(=O)NH | 3-(methyl-amino)propyl | 2-butyl | benzyl | H |
| 430 | naphthyl | NHC(=O)NH | C(=O)NH | benzyl | cyclopropyl | benzyl | H |
| 431 | benzyl | NHC(=O)NH | C(=O)NH | benzyl | cyclopropyl | 4-chloro-benzyl | H |
| 432 | benzyl | NHC(=O)NH | C(=O)NH | benzyl | 2-butyl | 4-pyridyl | H |
| 433 | benzyl | NHC(=O)NH | C(=O)NH | 2-acetamido- | 2-butyl | benzyl | H |
| 434 | benzyl | NHC(=O)NH | C(=O)NH | 2-(dimethyl-aminoethyl) | 2-propyl | benzyl | H |
| 435 | benzyl | NHC(=O)NH | C(=O)NH | benzyl | 2-butyl | benzyl | H |
| 436 | benzyl | NHC(=O)NH | SO₂NH | benzyl | 2-butyl | benzyl | H |
| 437 | benzyl | NHC(=O)NH | SO₂NH | 3-(methyl-amino)propyl | n-propyl | benzyl | H |
| 438 | benzyl | NHC(=O)NH | SO₂NH | isobutyl | 2-propyl | benzyl | H |
| 439 | naphthyl | NHC(=O)NH | SO₂NH | benzyl | 2-butyl | benzyl | CH₃ |
| 440 | benzyl | NHC(=O)NH | SO₂NH | benzyl | 2-butyl | benzyl | H |
| 441 | benzyl | OC(=O)NH | C(=O)NH | benzyl | 2-butyl | 2-pyridyl-methyl | H |
| 442 | 2-pyridyl-methyl | OC(=O)NH | C(=O)O | benzyl | 2-butyl | benzyl | H |
| 443 | benzyl | OC(=O)NH | C(=O) | benzyl | 2-butyl | benzyl | H |
| 444 | benzyl | OC(=O)NH | CH₂C(=O) | benzyl | 2-butyl | benzyl | H |
| 445 | benzyl | OC(=O)NH | CH₂C(=O)CH₂ | benzyl | 2-butyl | benzyl | H |
| 446 | benzyl | OC(=O)NH | C(=O)CH₂ | benzyl | 2-butyl | benzyl | H |
| 447 | benzyl | OC(=O)NH | SO₂NH | benzyl | 2-butyl | benzyl | H |

TABLE VII structure: R¹-CH(R³)-W-C(=S)-N(R¹⁸)-CH(R⁴)-CH(OH)-CH(OH)-CH(R⁴)-N(R¹⁸)-C(=S)-W-CH(R³)-R¹

| Ex. No. | R¹ | W | R³ | R⁴ | R¹⁸ |
|---|---|---|---|---|---|
| 448 | | | | | |
| 449 | benzyl | C(=S) | 2-propyl | benzyl | H |
| 450 | benzyl | C(=S)NH | 2-propyl | benzyl | H |
| 451 | benzyl | HNSO₂NH | 2-butyl | 2-pyridylmethyl | H |
| 452 | benzyl | SO₂ | 2-propyl | benzyl | H |
| 453 | 2,4-difluoro-phenyl | SO₂NH | 2-butyl | 3-pyridylmethyl | H |
| 454 | 4'-methylphenyl | SO₂NH | 2-butyl | benzyl | H |
| 455 | benzyl | SO₂NH | 2-(methyl-amino)ethyl | benzyl | H |
| 456 | benzyl | SO₂NH | 2-furanylmethyl | 4-pyridylmethyl | H |
| 457 | benzyl | SO₂NH | 2-propyl | benzyl | H |
| 458 | benzyl | SO₂NH | 2-propyl | benzyl | Et |

TABLE VII-continued

| Ex. No. | R¹ | W | R³ | R⁴ | R¹⁸ |
|---|---|---|---|---|---|
| 459 | benzyl | SO₂NH | 2-propyl | 3'-trifluoromethylbenzyl | H |
| 460 | benzyl | SO₂NH | 2-propyl | 2',4'-difluorobenzyl | H |
| 461 | benzyl | SO₂NH | 2-propyl | 3-phenylpropyl | H |
| 462 | benzyl | SO₂NH | 2-propyl | 1-pyrrolylethyl | H |
| 463 | benzyl | SO₂NH | 2-propyl | 2-(4-chlorophenyl)ethyl | H |
| 464 | benzyl | SO₂NH | 2-propyl | 1-phenylethyl | H |
| 465 | benzyl | SO₂NH | 3-hydroxy-1-propyl | 1-phenylethyl | H |
| 466 | benzyl | SO₂NH | cyclobutyl | 2-pyridylmethyl | H |
| 467 | benzyl | SO₂NH | cyclopropyl | benzyl | H |
| 468 | benzyl | SO₂NH | methylthiomethyl | 1-phenylethyl | H |
| 469 | cyclohexylethyl | SO₂NH | 2-butyl | benzyl | H |
| 470 | nonafluorobutyl | SO₂NH | 2-butyl | benzyl | H |
| 471 | phenyl | SO₂NH | 2-butyl | 2-pyridylmethyl | H |
| 472 | trifluoromethyl | SO₂NH | 2-butyl | benzyl | H |
| 473 | benzyl | NHC(=S)NH | 2-butyl | benzyl | H |
| 474 | benzyl | NHC(=S)NH | 2-butyl | 3-pyridylmethyl | CH₃ |
| 475 | benzyl | NHC(=S)NH | 2-propyl | benzyl | H |
| 476 | benzyl | NHC(=S)NH | 2-propyl | 2-naphthylmethyl | H |
| 477 | benzyl | CH₂O | 2-propyl | benzyl | H |
| 478 | benzyl | CH₂OCH₂ | 2-propyl | 2-pyridylmethyl | H |
| 479 | benzyl | CH₂CH₂ | 2-propyl | benzyl | H |
| 480 | benzyl | CH=CH | 2-propyl | benzyl | H |

TABLE VIII

| Ex. No. | R¹ | W | X | R² | R³ | R⁴ | R¹⁸ |
|---|---|---|---|---|---|---|---|
| 481 | | | | | | | |
| 482 | | | | | | | |
| 483 | benzyl | C(=O)NH | C(=O)NH | benzyl | 2-butyl | benzyl | H |
| 484 | benzyl | C(=O)NH | C(=O)O | benzyl | 2-butyl | 4-chlorobenzyl | H |
| 485 | benzyl | C(=O)NH | C(=O) | benzyl | 2-butyl | benzyl | H |
| 486 | benzyl | C(=O)NH | CH₂C(=O) | benzyl | 2-butyl | 2-pyridylmethyl | H |
| 487 | benzyl | NHC(=O)NH | C(=O)NH | 2-(dimethylaminoethyl) | 2-propyl | benzyl | H |
| 488 | benzyl | NHC(=O)NH | C(=O)NH | benzyl | 2-butyl | benzyl | H |
| 489 | benzyl | NHC(=O)NH | SO₂NH | benzyl | 2-butyl | benzyl | H |

TABLE IX

| Ex. No. | R¹ | W | R³ | R⁴ | R¹⁸ |
|---|---|---|---|---|---|
| 490 | | | | | |
| 491 | benzyl | SO₂NH | 2-propyl | 1-phenylethyl | H |
| 492 | benzyl | SO₂NH | 3-hydroxy-1-propyl | 1-phenylethyl | H |
| 493 | benzyl | SO₂NH | methylthiomethyl | 1-phenylethyl | H |
| 494 | phenyl | SO₂NHC(=O)NH | 2-butyl | 2-phenylethyl | H |
| 495 | phenyl | SO₂NHC(=O)NH | 2-butyl | 3'-carbomethoxybenzyl | H |
| 496 | benzyl | OC(=O)NH | 2-propyl | 3-naphthylmethyl | H |
| 497 | benzyl | OC(=O)NH | 2-propyl | 4'-(5-tetrazolyl)benzyl | H |
| 498 | benzyl | OC(=O)NH | 2-propyl | 4'-benzyloxybenzyl | H |
| 499 | benzyl | OC(=O)NH | 2-propyl | 4'-phenoxybenzyl | H |

TABLE IX-continued

Structure: R¹-CH(R³)-S(=O)₂-N(R¹⁸)-CH(R⁴)-CH(OH)-CH(OH)-CH(R⁴)-N(R¹⁸)-S(=O)₂-CH(R³)-W'-R¹

| Ex. No. | R¹ | W | R³ | R⁴ | R¹⁸ |
|---|---|---|---|---|---|
| 500 | benzyl | C(=O)NH | 2-butyl | 4'-trifluoro-methylbenzyl | H |
| 501 | 2-pyridylmethyl | C(=O)NH | 2-butyl | benzyl | H |
| 502 | benzyl | C(=O)NH | 2-butyl | benzyl | H |
| 503 | benzyl | C(=O)NH | 2-butyl | 2-pyridylmethyl | CH₃ |
| 504 | benzyl | C(=O)NH | cyclobutyl | benzyl | H |
| 505 | benzyl | C(=O)NH | cyclobutylmethyl | benzyl | H |
| 506 | benzyl | C(=O)NH | 2-butyl | benzyl | H |
| 507 | phenylethyl | C(=O)NH | 2-butyl | 3-pyridylmethyl | H |
| 508 | benzyl | C(=O)NHNH | 2-propyl | benzyl | H |
| 509 | benzyl | C(=O)O | 2-propyl | benzyl | H |
| 510 | benzyl | CH₂OCH₂ | 2-propyl | benzyl | H |
| 511 | benzyl | CH₂CH₂ | 2-propyl | 4-pyridylmethyl | H |
| 512 | benzyl | CH₂O | 2-propyl | benzyl | H |
| 513 | benzyl | CH=CH | 2-propyl | benzyl | H |
| 514 | benzyl | HNSO₂NH | 2-butyl | benzyl | H |
| 515 | benzyl | N=N | 2-propyl | benzyl | H |
| 516 | benzyl | NH—NH | 2-propyl | benzyl | H |
| 517 | adamantyl | NHC(=O)NH | 2-butyl | 2-pyridylmethyl | H |
| 518 | benzyl | NHC(=O)NH | 2-butyl | benzyl | H |
| 519 | benzyl | NHC(=O)NH | 2-butyl | benzyl | CF₃ |
| 520 | benzyl | NHC(=O)NH | 2-propyl | benzyl | H |
| 521 | benzyl | NHC(=O)NH | benzyl | 3-pyridylmethyl | H |
| 522 | benzyl | NHC(=O)NH | CH₂CF₃ | benzyl | H |
| 523 | benzyl | NHC(=O)NH | CH₂CH₂C(=O)NH | benzyl | H |
| 524 | benzyl | NHC(=O)NH | cyclobutyl | benzyl | H |
| 525 | benzyl | NHC(=O)NH | cyclobutyl | benzyl | CF₃ |
| 526 | benzyl | NHC(=O)NH | cyclobutylmethyl | 4-pyridylmethyl | H |
| 527 | benzyl | NHC(=O)NH | cyclopentylmethyl | benzyl | H |
| 528 | benzyl | NHC(=O)NH | cyclopropyl | benzyl | H |
| 529 | benzyl | NHC(=O)NH | cyclopropylmethyl | benzyl | H |
| 530 | cis-2-deca-hydronaphthylmethyl | NHC(=O)NH | 2-butyl | benzyl | H |
| 531 | cis-2-deca-hydronaphthylmethyl | NHC(=O)NH | 2-butyl | benzyl | CF₃ |
| 532 | 2-hydroxy-3,3-dimethylpropyl | NHC(=O)NH | 2-butyl | benzyl | H |
| 533 | 2-hydroxy-3,3-dimethylpropyl | NHC(=O)NH | 2-butyl | benzyl | CF₃ |
| 534 | 2-hydroxy-indanylmethyl | NHC(=O)NH | 2-butyl | 2-pyridylmethyl | H |
| 535 | benzyl | OC(=O)NH | 1-methoxy-2-propyl | benzyl | H |
| 536 | benzyl | OC(=O)NH | 2'-hydroxy-cyclopentylmethyl | benzyl | H |
| 537 | benzyl | OC(=O)NH | 2,2,2-trichloroethyl | 3-pyridylmethyl | H |
| 538 | benzyl | OC(=O)NH | 2,2,2-trichloroethyl | benzyl | H |
| 539 | benzyl | OC(=O)NH | 2-butyl | benzyl | H |
| 540 | benzyl | OC(=O)NH | 2-propyl | benzyl | H |
| 541 | benzyl | OC(=O)NH | 2-propyl | benzyl | CF₃ |
| 542 | 2-benzimida-zolylmethyl | OC(=O)NH | 2-butyl | benzyl | H |
| 543 | 2-naphthyl-methyl | OC(=O)NH | 2-butyl | 4-pyridylmethyl | H |
| 544 | 2-pyridylmethyl | OC(=O)NH | 2-butyl | benzyl | H |
| 545 | CH₃SO₂CH₂CH₂ | OC(=O)NH | 2-butyl | benzyl | H |
| 546 | cyclopentylethyl | OC(=O)NH | 2-butyl | benzyl | H |
| 547 | F₂HCOC₆H₄CH₂ | OC(=O)NH | 2-butyl | benzyl | H |
| 548 | 2,4-difluoro-phenyl | SO₂NH | 2-butyl | benzyl | H |
| 549 | 4'-methylphenyl | SO₂NH | 2-butyl | benzyl | H |
| 550 | benzyl | SO₂NH | 2-(methylamino)ethyl | benzyl | H |
| 551 | benzyl | SO₂NH | 2-furanylmethyl | 2-pyridylmethyl | H |
| 552 | benzyl | SO₂NH | 2-propyl | benzyl | H |
| 553 | benzyl | SO₂NH | cyclobutyl | benzyl | H |
| 554 | benzyl | SO₂NH | cyclopropyl | benzyl | H |
| 555 | 4'-methylphenyl | SO₂NHC(=O)NH | 2-(dimethylamino)-ethyl | benzyl | H |
| 556 | 4'-methylphenyl | SO₂NHC(=O)NH | 2-butyl | benzyl | H |
| 557 | 4'-methylphenyl | SO₂NHC(=O)NH | 2-butyl | benzyl | H |
| 558 | 4'-methylphenyl | SO₂NHC(=O)NH | benzyl | benzyl | H |
| 559 | 4'-methylphenyl | SO₂NHC(=O)NH | CH₂CH₂OH | 3-pyridylmethyl | H |
| 560 | 4'-methylphenyl | SO₂NHC(=O)NH | cyclobutyl | benzyl | H |
| 561 | phenyl | SO₂NHC(=O)NH | 2-butyl | 4-pyridylmethyl | CF₃ |

TABLE IX-continued

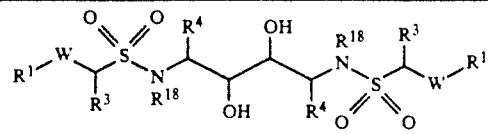

| Ex. No. | $R^1$ | W | $R^3$ | $R^4$ | $R^{18}$ |
|---|---|---|---|---|---|
| 562 | phenyl | SO₂NHC(=O)NH | cyclopropyl | benzyl | H |
| 563 | trifluoromethyl | SO₂NHC(=O)NH | 2-butyl | benzyl | H |
| 564 | trifluoromethyl | SO₂NHC(=O)NH | 2-butyl | benzyl | H |
| 565 | trifluoromethyl | SO₂NHC(=O)NH | cyclobutyl | benzyl | H |
| 566 | trifluoromethyl | SO₂NHC(=O)NH | cyclopropyl | benzyl | H |

TABLE X

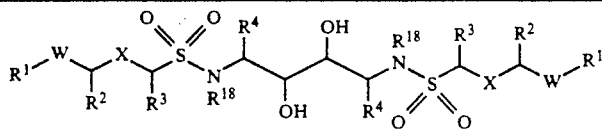

| Ex. No. | $R^1$ | W | X | $R^2$ | $R^3$ | $R^4$ | $R^{12}$ |
|---|---|---|---|---|---|---|---|
| 567 | | | | | | | |
| 568 | benzyl | C(=O)NH | C(=O)NH | benzyl | 2-butyl | benzyl | H |
| 569 | benzyl | C(=O)NH | C(=O)O | benzyl | 2-propyl | benzyl | H |
| 570 | benzyl | C(=O)NH | CH₂C(=O)CH₂ | 4-chlorophenyl | cyclopropyl | benzyl | H |
| 571 | benzyl | C(=O)NH | C(=O)CH₂ | benzyl | ethyl | benzyl | H |
| 572 | benzyl | C(=O)NH | SO₂NH | benzyl | cyclobutyl | benzyl | H |
| 573 | benzyl | C(=O)NH | CH₂NCH₃ | 2-(dimethylaminoethyl) | 2-butyl | benzyl | H |
| 574 | benzyl | C(=O)NH | CH₂NH | benzyl | 2-butyl | benzyl | H |
| 575 | benzyl | C(=O)NH | CH₂CH₂ | naphthyl | 2-butyl | 4-fluorophenyl | H |
| 576 | benzyl | C(=O)NH | CH=CH | benzyl | 2-butyl | benzyl | H |
| 577 | benzyl | C(=O)NH | CH(OH)CH(OH) | 2-acetamido | 2-butyl | naphthyl | H |
| 578 | 3-trifluoromethylbenzyl | C(=O)NH | CH(OH)CH₂ | benzyl | 2-butyl | benzyl | H |
| 579 | benzyl | C(=O)NH | CH₂CH(OH) | benzyl | 2-butyl | 4-methoxyphenyl | H |
| 580 | benzyl | C(=O)NH | CH(OH) | 4-methanesulfonyl | 2-butyl | benzyl | H |
| 581 | benzyl | C(=O)NH | SO₂NH | benzyl | 2-butyl | 2,4-dichlorophenyl | CH₃ |
| 582 | benzyl | NHC(=O)NH | C(=O)NH | benzyl | 2-butyl | benzyl | H |
| 583 | 2-pyridylmethyl | NHC(=O)NH | C(=O)NH | benzyl | 2-butyl | benzyl | H |
| 584 | 2,4-dimethoxybenzyl | NHC(=O)NH | C(=O)NH | benzyl | 2-butyl | benzyl | H |
| 585 | benzyl | NHC(=O)NH | C(=O)NH | 3-(methylamino)-propyl | 2-butyl | benzyl | H |
| 586 | naphthyl | NHC(=O)NH | C(=O)NH | benzyl | cyclopropyl | benzyl | H |
| 587 | benzyl | NHC(=O)NH | C(=O)NH | 2-imidazolylmethyl | cyclopropyl | 4-chlorobenzyl | H |
| 588 | benzyl | NHC(=O)NH | C(=O)NH | benzyl | 2-butyl | 4-pyridyl | H |
| 589 | benzyl | NHC(=O)NH | C(=O)NH | 2-acetamido | 2-butyl | benzyl | H |
| 590 | benzyl | NHC(=O)NH | C(=O)NH | 2-(dimethylaminoethyl) | 2-propyl | benzyl | H |
| 591 | benzyl | NHC(=O)NH | C(=O)NH | benzyl | 2-butyl | benzyl | H |
| 592 | benzyl | NHC(=O)NH | SO₂NH | benzyl | 2-butyl | benzyl | H |
| 593 | benzyl | NHC(=O)NH | SO₂NH | 3-(methylamino)propyl | n-propyl | benzyl | H |
| 594 | benzyl | NHC(=O)NH | SO₂NH | isobutyl | 2-propyl | benzyl | H |
| 595 | naphthyl | NHC(=O)NH | SO₂NH | benzyl | 2-butyl | benzyl | H |
| 596 | benzyl | NHC(=O)NH | SO₂NH | 3-indolylmethyl | 2-butyl | benzyl | CH₃ |
| 597 | benzyl | OC(=O)NH | C(=O)NH | benzyl | 2-butyl | benzyl | H |
| 598 | benzyl | OC(=O)NH | C(=O)O | benzyl | 2-propyl | benzyl | H |
| 599 | benzyl | OC(=O)NH | CH₂C(=O)CH₂ | 4-chlorophenyl | cyclopropyl | benzyl | H |
| 600 | adamantyl | OC(=O)NH | C(=O)CH₂ | benzyl | ethyl | benzyl | H |
| 601 | benzyl | OC(=O)NH | SO₂NH | benzyl | cyclobutyl | benzyl | H |
| 602 | benzyl | OC(=O)NH | CH₂NCH₃ | 2-(dimethylaminoethyl) | 2-butyl | benzyl | H |
| 603 | cyclohexylmethyl | OC(=O)NH | CH₂NH | benzyl | 2-butyl | benzyl | H |
| 604 | benzyl | OC(=O)NH | CH₂CH₂ | naphthyl | 2-butyl | 4-fluorophenyl | H |

TABLE XI

Structure: $R^1\text{-W-CH}_2\text{-N}(R^{18})\text{-CH}(R^4)\text{-CH(OH)-CH(OH)-CH}(R^4)\text{-N}(R^{18})\text{-CH}_2\text{-W-}R^1$ with $R^3$ groups on the carbons alpha to N.

| Ex. No. | R¹ | W | R³ | R⁴ | R¹⁸ |
|---|---|---|---|---|---|
| 605 | 2-pyridylmethyl | C(=O) | 2-propyl | benzyl | H |
| 606 | benzyl | C(=O) | 2-butyl | cyclohexylmethyl | H |
| 607 | benzyl | C(=O) | 2-propyl | benzyl | H |
| 608 | trifluoromethyl | C(=O) | 2-propyl | 2-pyridylmethyl | H |
| 609 | benzyl | C(=O)CH₂ | 2-propyl | benzyl | H |
| 610 | 2-pyridylmethyl | C(=O)NH | 2-butyl | 3-pyridylmethyl | H |
| 611 | benzyl | C(=O)NH | 2-butyl | benzyl | H |
| 612 | benzyl | C(=O)NH | 2-butyl | benzyl | CH₃ |
| 613 | benzyl | C(=O)NH | 2-butyl | 4'-trifluoromethylbenzyl | H |
| 614 | benzyl | C(=O)NH | cyclobutyl | benzyl | H |
| 615 | benzyl | C(=O)NH | cyclobutylmethyl | benzyl | H |
| 616 | methyl | C(=O)NH | 2-butyl | 3-pyridylmethyl | H |
| 617 | phenylethyl | C(=O)NH | 2-butyl | benzyl | H |
| 618 | benzyl | C(=O)NHNH | 2-propyl | benzyl | H |
| 619 | benzyl | C(=O)O | 2-propyl | benzyl | H |
| 620 | benzyl | C(=S) | 2-propyl | 4-pyridylmethyl | H |
| 621 | benzyl | C(=S)NH | 2-propyl | benzyl | H |
| 622 | benzyl | C(Cl)=N | 2-propyl | benzyl | H |
| 623 | 2-pyridylmethyl | C(NHMe)=N | 2-propyl | benzyl | H |
| 624 | 3-methylpropyl | C(NHMe)=N | 2-propyl | benzyl | H |
| 625 | benzyl | C(NHMe)=N | 2-propyl | 2-pyridylmethyl | H |
| 626 | benzyl | C(NHMe)=N | 2-propyl | benzyl | CH₃ |
| 627 | benzyl | C(NHMe)=N | 2-propyl | 4-(HCF₂O)C₆H₄CH₂ | |
| 628 | benzyl | C(OCH₂CH₃)=N | 2-propyl | benzyl | H |
| 629 | benzyl | C(OCH₂CH₃)=N | 2-propyl | 4'-trifluoromethylbenzyl | H |
| 630 | benzyl | C(OCH₂CH₃)=N | 2-propyl | 4'-chlorobenzyl | H |
| 631 | benzyl | CH₂OCH₂ | 2-propyl | benzyl | H |
| 632 | benzyl | CH₂CH₂ | 2-propyl | benzyl | H |
| 633 | benzyl | CH₂CHOH | 2-propyl | 3-pyridylmethyl | H |
| 634 | benzyl | CH₂O | 2-propyl | benzyl | H |
| 635 | benzyl | CH₂OH | 2-propyl | benzyl | H |
| 636 | benzyl | CH=CH | 2-propyl | benzyl | H |
| 637 | benzyl | CHOHCH₂ | 2-propyl | 4-pyridylmethyl | H |
| 638 | benzyl | CHOHCHOH | 2-propyl | benzyl | H |
| 639 | benzyl | HNC(=S)NH | 2-propyl | benzyl | H |
| 640 | benzyl | HNSO₂ | 2-butyl | benzyl | H |
| 641 | benzyl | HNSO₂NH | 2-butyl | benzyl | H |
| 642 | benzyl | N=N | 2-propyl | 2-pyridylmethyl | H |
| 643 | benzyl | NH—NH | 2-propyl | benzyl | H |
| 644 | 2-hydroxy-3,3-dimethylpropyl | NHC(=O)NH | 2-butyl | benzyl | H |
| 645 | 4-t-butyl-phenylmethyl | NHC(=O)NH | 2-butyl | benzyl | H |
| 646 | adamantyl | NHC(=O)NH | 2-butyl | benzyl | H |
| 647 | benzyl | NHC(=O)NH | 2-butyl | 2-pyridylmethyl | H |
| 648 | benzyl | NHC(=O)NH | 2-butyl | benzyl | CH₃ |
| 649 | benzyl | NHC(=O)NH | 2-propyl | benzyl | H |
| 650 | benzyl | NHC(=O)NH | 2-propyl | 3-pyrrazolylmethyl | H |
| 651 | benzyl | NHC(=O)NH | 2-propyl | 3-(trifluoromethanesulfonyl)propyl | H |
| 652 | benzyl | NHC(=O)NH | 2-propyl | 4-(1-methyl)piperidinylmethyl | H |
| 653 | benzyl | NHC(=O)NH | 2-thiozolylmethyl | benzyl | H |
| 654 | benzyl | NHC(=O)NH | cyclobutyl | 3-pyridylmethyl | CH₃ |
| 655 | benzyl | NHC(=O)NH | cyclobutylmethyl | benzyl | H |
| 656 | 2-pyridylmethyl | OC(=O)NH | 2-butyl | benzyl | H |
| 657 | 9-fluorenylmethyl | OC(=O)NH | 2-butyl | 4-pyridylmethyl | H |
| 658 | adamantylmethyl | OC(=O)NH | 2-butyl | benzyl | H |
| 659 | benzyl | OC(=O)NH | 1-methoxy-2-propyl | benzyl | H |
| 660 | benzyl | OC(=O)NH | 2'-hydroxy-cyclopentylmethyl | benzyl | H |
| 661 | benzyl | OC(=O)NH | 2-propyl | benzyl | CH₃ |
| 662 | benzyl | OC(=O)NH | 2-propyl | 3-naphthylmethyl | H |
| 663 | benzyl | OC(=O)NH | 2-propyl | 4'-phenoxybenzyl | H |
| 664 | benzyl | OC(=O)NH | 2-propyl | 4'-benzyloxybenzyl | H |
| 665 | benzyl | OC(=O)NH | 2-propyl | 4'-(5-tetrazolyl)benzyl | H |
| 666 | benzyl | OCH₂ | 2-propyl | benzyl | H |
| 667 | benzyl | OP(=O)(OMe)O | 2-propyl | benzyl | H |
| 668 | benzyl | SO₂ | 2-propyl | 2-pyridylmethyl | H |
| 669 | 2,4-difluorophenyl | SO₂NH | 2-butyl | benzyl | H |

TABLE XI-continued

| Ex. No. | R¹ | W | R³ | R⁴ | R¹⁸ |
|---|---|---|---|---|---|
| 670 | 4'-methylphenyl | SO₂NH | 2-butyl | benzyl | H |
| 671 | benzyl | SO₂NH | 2-propyl | 3-pyridylmethyl | Et |
| 672 | benzyl | SO₂NH | 2-propyl | 3'-trifluoromethylbenzyl | H |
| 673 | benzyl | SO₂NH | 2-propyl | 2',4'-difluorobenzyl | H |
| 674 | nonafluorobutyl | SO₂NH | 2-butyl | benzyl | H |
| 675 | phenyl | SO₂NH | 2-butyl | benzyl | H |
| 676 | trifluoromethyl | SO₂NH | 2-butyl | 4-pyridylmethyl | H |
| 677 | 2,4-difluorophenyl | SO₂NHC(=O)NH | 2-butyl | benzyl | H |
| 678 | 4'-methylphenyl | SO₂NHC(=O)NH | 2-(dimethylamino)ethyl | benzyl | H |
| 679 | 4'-methylphenyl | SO₂NHC(=O)NH | 2-butyl | benzyl | H |
| 680 | 4'-methylphenyl | SO₂NHC(=O)NH | CH₂CH₂OH | 4-pyridylmethyl | H |
| 681 | 4'-methylphenyl | SO₂NHC(=O)NH | cyclobutyl | benzyl | H |
| 682 | 4'-methylphenyl | SO₂NHC(=O)NH | cyclohexylmethyl | benzyl | H |
| 683 | methyl | SO₂NHC(=O)NH | 2-butyl | 3-pyridylmethyl | H |
| 684 | phenyl | SO₂NHC(=O)NH | 2-butyl | benzyl | H |
| 685 | phenyl | SO₂NHC(=O)NH | 2-butyl | benzyl | H |
| 686 | phenyl | SO₂NHC(=O)NH | 2-butyl | 2'-chlorobenzyl | H |
| 687 | phenyl | SO₂NHC(=O)NH | 2-butyl | 3-naphthylmethyl | H |
| 688 | phenyl | SO₂NHC(=O)NH | 2-butyl | 2-(4-fluorophenyl)ethyl | H |
| 689 | phenyl | SO₂NHC(=O)NH | 2-butyl | 2-phenylethyl | H |
| 690 | phenyl | SO₂NHC(=O)NH | 2-butyl | 3'-carbomethoxybenzyl | H |
| 691 | phenyl | SO₂NHC(=O)NH | 2-butyl | benzyl | CH₃ |
| 692 | phenyl | SO₂NHC(=O)NH | cyclopropyl | 4-pyridylmethyl | H |
| 693 | trifluoromethyl | SO₂NHC(=O)NH | 2-butyl | benzyl | H |
| 694 | trifluoromethyl | SO₂NHC(=O)NH | 2-butyl | benzyl | H |
| 695 | trifluoromethyl | SO₂NHC(=O)NH | cyclobutyl | 2-pyridylmethyl | H |
| 696 | trifluoromethyl | SO₂NHC(=O)NH | cyclopropyl | benzyl | H |

TABLE XII

| Ex. No. | R¹ | W | X | R² | R³ | R⁴ | R¹⁸ |
|---|---|---|---|---|---|---|---|
| 697 | benzyl | OC(=O)NH | C(=O)NH | benzyl | 2-butyl | benzyl | H |
| 698 | benzyl | OC(=O)NH | C(=O)O | benzyl | 2-butyl | benzyl | H |
| 699 | benzyl | OC(=O)NH | C(=O) | 2-(dimethylamino)ethyl | 2-butyl | benzyl | H |
| 700 | benzyl | OC(=O)NH | CH₂C(=O) | benzyl | 2-propyl | benzyl | H |
| 701 | benzyl | OC(=O)NH | CH₂C(=O)CH₂ | benzyl | 2-propyl | 4-chlorobenzyl | H |
| 702 | benzyl | OC(=O)NH | C(=Q)CH₂ | benzyl | 2-propyl | benzyl | H |
| 703 | benzyl | OC(=O)NH | SO₂NH | 3-(methylamino)propyl | ethyl | 2-pyridylmethyl | H |
| 704 | benzyl | OC(=O)NH | SO₂ | benzyl | 2-thiazolylmethyl | benzyl | H |
| 705 | benzyl | OC(=O)NH | CH₂OCH₂ | benzyl | cyclobutyl | benzyl | H |
| 706 | benzyl | OC(=O)NH | CH₂O | benzyl | cyclobutylmethyl | 3-pyridylmethyl | H |
| 707 | benzyl | OC(=O)NH | CH₂NCH₃ | cyclohexylmethyl | 2-butyl | benzyl | CH₃ |
| 708 | benzyl | OC(=O)NH | CH₂NH | benzyl | 3-cyanopropy | benzyl | H |
| 709 | benzyl | HNC(=O)NH | CH₂CH₂ | benzyl | 2-butyl | 3-indolyl | H |
| 710 | benzyl | C(=O)NH | CH=CH | benzyl | 1-methoxy-2-propyl | 4-pyridylmethyl | H |
| 711 | 2-pyridylmethyl | OC(=O)NH | CH(OH)CH(OH) | benzyl | 2'-hydroxycyclopentylmethyl | benzyl | H |
| 712 | benzyl | OC(=O)NH | CH(OH)CH₂ | benzyl | 2-propyl | 4-fluorobenzyl | H |
| 713 | naphthyl | OC(=O)NH | CH₂CH(OH) | 4-pyridylmethyl | 2-propyl | benzyl | H |
| 714 | benzyl | OC(=O)NH | CH(OH) | benzyl | benzyl | naphthyl | H |
| 715 | 2,3-difluorobenzyl | OC(=O)NH | C(—N[Me]₂)=N | 4-imidazolylmethyl | 2-propyl | benzyl | H |
| 716 | benzyl | OC(=O)NH | C(—OEt)=N | benzyl | 2-propyl | benzyl | H |
| 717 | 1-cyclo- | OC(=O)NH | C(Cl—)—N | benzyl | 2-propyl | benzyl | H |

TABLE XII-continued

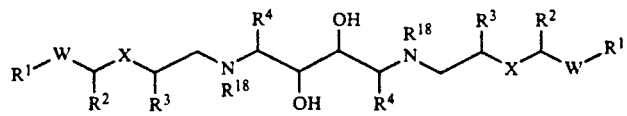

| Ex. No. | R¹ | W | X | R² | R³ | R⁴ | R¹⁸ |
|---|---|---|---|---|---|---|---|
| | hexenylmethyl | | | | | | |

TABLE XIII

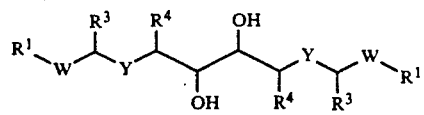

| Ex. No. | R¹ | W | R³ | R⁴ | Y |
|---|---|---|---|---|---|
| 718 | 2-pyridylmethyl | C(=O) | 2-propyl | benzyl | C(Cl)=N |
| 719 | benzyl | C(=O) | 2-butyl | cyclohexylmethyl | C(OEt)=N |
| 720 | benzyl | C(=O)CH₂ | 2-propyl | benzyl | C(OEt)=N |
| 721 | 2-pyridylmethyl | C(=O)NH | 2-butyl | 2-pyridyl-methyl | C(NMe₂)=N |
| 722 | benzyl | C(=O)NH | 2-butyl | benzyl | C(NHMe)=N |
| 723 | benzyl | C(=O)NH | 2-butyl | benzyl | C(Cl)=N |
| 724 | benzyl | C(=O)NH | 2-butyl | 4'-trifluoro methylbenzyl | C(NHMe)=N |
| 725 | benzyl | C(=O)NHNH | 2-propyl | benzyl | C(NHMe)=N |
| 726 | benzyl | C(=O)O | 2-propyl | benzyl | C(OMe)=N |
| 727 | benzyl | C(=S) | 2-propyl | 3-pyridyl-methyl | C(NHMe₂)=N |
| 728 | benzyl | C(=S)NH | 2-propyl | benzyl | C(NHMe)=N |
| 729 | benzyl | C(Cl)=N | 2-propyl | benzyl | C(OEt)=N |
| 730 | 2-pyridylmethyl | C(NHMe)=N | 2-propyl | benzyl | C(OEt)=N |
| 731 | 3-methylpropyl | C(NHMe)=N | 2-propyl | benzyl | C(NHMe)=N |
| 732 | benzyl | C(NHMe)=N | 2-propyl | benzyl | C(NHMe)=N |
| 733 | 2-pyridylethyl | C(OCH₂CH₃)=N | 2-propyl | benzyl | C(NHMe)=N |
| 734 | benzyl | C(OCH₃)=N | 2-propyl | benzyl | C(OEt)=N |
| 735 | benzyl | CH₂OCH₂ | 2-propyl | benzyl | C(OEt)=N |
| 736 | benzyl | CH₂CH₂ | 2-propyl | 4-pyridyl-methyl | C(NMe₂)=N |
| 737 | benzyl | CH₂CHOH | 2-propyl | benzyl | C(NMe)=N |
| 738 | benzyl | CH₂O | 2-propyl | benzyl | C(OEt)=N |
| 739 | benzyl | CH₂OH | 2-propyl | 2-pyridyl-methyl | C(OEt)=N |
| 740 | benzyl | CH=CH | 2-propyl | benzyl | C(NHMe)=N |
| 741 | benzyl | CHOHCH₂ | 2-propyl | benzyl | C(NHMe)=N |
| 742 | benzyl | CHOHCHOH | 2-propyl | 3-pyridyl-methyl | C(OEt)=N |
| 743 | benzyl | HNC(=S)NH | 2-propyl | benzyl | C(OMe)=N |
| 744 | benzyl | HNSO₂ | 2-butyl | benzyl | C(OEt)=N |
| 745 | benzyl | HNSO₂NH | 2-butyl | benzyl | C(OEt)=N |
| 746 | benzyl | N=N | 2-propyl | 4-pyridyl-methyl | C(NHMe)=N |
| 747 | benzyl | NH—NH | 2-propyl | benzyl | C(NHMe)=N |
| 748 | (—CH₂CH₂CH₂CH₂CH₂) | NHC(=O)NH | 2-butyl | benzyl | C(NHMe)=N |
| 749 | (—CH₂CH₂OCH₂CH₂—) | NHC(=O)NH | 2-butyl | benzyl | C(OEt)=N |
| 750 | 2-hydroxy-3,3-dimethylpropyl | NHC(=O)NH | 2-butyl | benzyl | C(OMe)=N |
| 751 | 2-hydroxy-3,3-dimethylpropyl | NHC(=O)NH | 2-butyl | benzyl | C(Cl)=N |
| 752 | 2-hydroxy-indanylmethyl | NHC(=O)NH | 2-butyl | benzyl | C(NHMe)=N |
| 753 | adamantyl | NHC(=O)NH | 2-butyl | benzyl | C(OEt)=N |
| 754 | benzyl | NHC(=O)NH | 2-butyl | 2-pyridyl-methyl | C(OEt)=N |
| 755 | benzyl | NHC(=O)NH | 2-butyl | benzyl | C(Cl)=N |
| 756 | benzyl | NHC(=O)NH | 2-propyl | benzyl | C(NHMe)=N |
| 757 | benzyl | NHC(=O)NH | 2-propyl | 2-naphthyl methyl | C(NHMe)=N |
| 758 | benzyl | O | 2-propyl | benzyl | C(OEt)=N |
| 759 | 2-benzimida-zolylmethyl | OC(=O)NH | 2-butyl | 3-pyridyl-methyl | C(OEt)=N |
| 760 | 2-naphthylmethyl | OC(=O)NH | 2-butyl | benzyl | C(OEt)=N |
| 761 | 2-pyridylmethyl | OC(=O)NH | 2-butyl | benzyl | C(OEt)=N |
| 762 | benzyl | OC(=O)NH | 1-methoxy-2-propyl | benzyl | C(NMe₂)=N |
| 763 | benzyl | OC(=O)NH | 2-butyl | benzyl | C(NHMe)=N |
| 764 | benzyl | OC(=O)NH | 2-propyl | 4-pyridyl-methyl | C(NHMe)=N |
| 765 | benzyl | OC(=O)NH | 2-propyl | benzyl | C(Cl)=N |
| 766 | benzyl | OCH₂ | 2-propyl | benzyl | C(OMe)=N |
| 767 | benzyl | OP(=O)(OMe)O | 2-propyl | benzyl | C(OEt)=N |
| 768 | benzyl | SO₂ | 2-propyl | benzyl | C(NHMe)=N |
| 769 | 2,4-di-fluorophenyl | SO₂NH | 2-butyl | benzyl | C(NHMe)=N |

TABLE XIII-continued

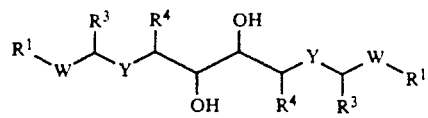

| Ex. No. | R¹ | W | R³ | R⁴ | Y |
|---|---|---|---|---|---|
| 770 | 4'-methylphenyl | SO₂NH | 2-butyl | benzyl | C(NHMe)=N |
| 771 | benzyl | SO₂NH | 2-(methyl-amino)ethyl | benzyl | C(NHMe)=N |
| 772 | benzyl | SO₂NH | 2-furanyl-methyl | benzyl | C(NHMe)=N |
| 773 | benzyl | SO₂NH | 2-propyl | 2-pyridyl-methyl | C(NHMe)=N |
| 774 | benzyl | SO₂NH | 2-propyl | benzyl | C(Cl)=N |
| 775 | benzyl | SO₂NHC(=O)NH | 2-butyl | benzyl | C(OEt)=N |
| 776 | cyclohexylethyl | SO₂NHC(=O)NH | 2-butyl | 3-pyridyl-methyl | C(OEt)=N |
| 777 | methyl | SO₂NHC(=O)NH | 2-butyl | benzyl | C(OMe)=N |
| 778 | nonafluorobutyl | SO₂NHC(=O)NH | 2-butyl | benzyl | C(OMe)=N |
| 779 | phenyl | SO₂NHC(=O)NH | 2-butyl | 4-pyridyl-methyl | C(NHMe)=N |
| 780 | phenyl | SO₂NHC(=O)NH | 2-butyl | benzyl | C(NMe₂)=N |
| 781 | trifluoromethyl | SO₂NHC(=O)NH | cyclopropyl | benzyl | C(NHMe)=N |

TABLE XIV

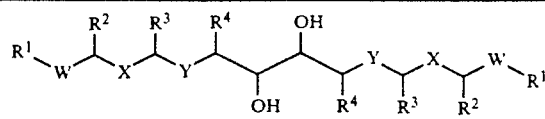

| Ex. No. | R¹ | W | X | R² | R³ | R⁴ | Y |
|---|---|---|---|---|---|---|---|
| 782 | 2-pyridylmethyl | C(=O)NH | C(=O)NH | benzyl | 2-butyl | benzyl | C(NMe₂)=N |
| 783 | benzyl | C(=O)NH | C(=O)NH | 3-(dimethyl-amino)propyl | cyclobutyl | benzyl | C(NHMe)=N |
| 784 | benzyl | C(=O)NH | C(=O)NH | cyclopentylmethyl | 2-butyl | benzyl | C(Cl)=N |
| 785 | benzyl | C(=O)NH | C(=O)NH | benzyl | cyclopropyl | benzyl | C(NHMe)=N |
| 786 | benzyl | C(=O)NHNH | C(=O)NH | 4-chloro-benzyl | 2-propyl | benzyl | C(NHMe)=N |
| 787 | benzyl | C(=O)O | C(=O)NH | 3,3,3-triflouro-ethyl | 2-propyl | benzyl | C(OMe)=N |
| 788 | benzyl | C(=S) | C(=O)NH | 2-imidazol-ylmethyl | 2-propyl | benzyl | C(NMe₂)=N |

TABLE XV $$R^1-W \quad \underset{R^3}{\overset{O}{\underset{\|}{C}}} \underset{H}{N} \underset{OH}{\overset{R^4}{\underset{|}{C}}} \underset{OH}{\overset{OH}{\underset{|}{C}}} \underset{R^4}{\overset{H}{\underset{|}{N}}} \underset{O}{\overset{R^8}{\underset{|}{C}}} W-R^{10}$$

| Ex. No. | R¹ | W | R³ | R⁴ | R⁸ | R¹⁰ |
|---|---|---|---|---|---|---|
| 789 | 2-pyridylethyl | C(=O) | 2-propyl | benzyl | 3-(dimethyl-amino)-1-propyl | 2,4-difluorophenyl |
| 790 | 2-pyridylmethyl | C(=O) | 2-butyl | 4-imidazolyl-methyl | benzyl | 4-methylphenyl |
| 791 | benzyl | C(=O) | 2-butyl | cyclohexylmethyl | CH₂NHC(=O)NHCH₃ | benzyl |
| 792 | benzyl | C(=O) | 2-propyo | benzyl | CH₂NHSO₂CH₃ | benzyl |
| 793 | benzyl | C(=O) | 2-propyl | 2-pyridyl-methyl | cyclobutyl | benzyl |
| 794 | benzyl | C(=O) | benzyl | benzyl | cyclobutylmethyl | benzyl |
| 795 | n-propyl | C(=O) | 2-propyl | benzyl | cyclopropyl | benzyl |
| 796 | naphthyl | C(=O) | 2-propyl | 3-pyridyl-methyl | cyclopropylmethyl | benzyl |
| 797 | phenyl | C(=O) | 2-propyl | benzyl | methyl | benzyl |
| 798 | thiophenyl | C(=O) | 2-propyl | benzyl | 2-butyl | benzyl |
| 799 | trifluoromethyl | C(=O) | 2-propyl | benzyl | 2-butyl | benzyl |
| 800 | benzyl | C(=O)CH₂ | 2-propyl | benzyl | 2-butyl | benzyl |
| 801 | 2-pyridylmethyl | C(=O)NH | 2-propyl | 3-pyridyl-methyl | 2-propyl | benzyl |
| 802 | benzyl | C(=O)NH | 2-butyl | benzyl | 2-propyl | benzyl |
| 803 | benzyl | C(=O)NH | 2-butyl | benzyl | 2-propyl | benzyl |
| 804 | benzyl | C(=O)NH | cyclobutyl | 4-pyridyl-methyl | 2-butyl | benzyl |
| 805 | benzyl | C(=O)NH | cyclobutyl-methyl | benzyl | 2-butyl | cyclohexyl-ethyl |
| 806 | methyl | C(=O)NH | 2-butyl | benzyl | 2-(methyl-amino)ethyl | nonafluoro-butyl |
| 807 | phenylethyl | C(=O)NH | 2-butyl | benzyl | 2-furanylmethyl | phenyl |
| 808 | benzyl | C(=O)NHNH | 2-propyl | benzyl | 2-propyl | trifluoromethyl |
| 809 | benzyl | C(=O)O | 2-propyl | benzyl | 2-propyl | 2,4-difluorophenyl |
| 810 | benzyl | C(=S) | 2-propyl | benzyl | 2-propyl | 4-methylphenyl |
| 811 | benzyl | C(=S)NH | 2-propyl | benzyl | 2-propyl | 4-methylphenyl |
| 812 | benzyl | C(Cl)=N | 2-propyl | benzyl | 2-propyl | 4-methylphenyl |
| 813 | 2-pyridyl-methyl | C(NHMe)=N | 2-propyl | benzyl | 2-propyl | 4-methylphenyl |
| 814 | 3-methylpropyl | C(NHMe)=N | 2-propyl | benzyl | 2-propyl | 4-methylphenyl |
| 815 | benzyl | C(NHMe)=N | 2-propyl | benzyl | 2-propyl | 4-methylphenyl |
| 816 | benzyl | C(NHMe)=N | 2-propyl | benzyl | 3-hydroxy-1-propyl | 4-methylphenyl |

TABLE XV-continued

| Ex. No. | R¹ | W | R³ | R⁴ | R⁸ | R¹⁰ |
|---|---|---|---|---|---|---|
| 817 | 2-pyridylethyl | C(OCH$_2$CH$_3$)=N | 2-propyl | benzyl | cyclobutyl | 4'-methylphenyl |
| 818 | 3-naphthylmethyl | C(OCH$_2$CH$_3$)=N | 2-propyl | benzyl | cyclopropyl | benzyl |
| 819 | 4'-t-butylbenzyl | C(OCH$_2$CH$_3$)=N | 2-propyl | benzyl | methylthiomethyl | cyclohexylethyl |
| 820 | benzyl | C(OCH$_2$CH$_3$)=N | 2-propyl | benzyl | 2-butyl | methyl |
| 821 | benzyl | C(OCH$_2$CH$_3$)=N | 2-propyl | 4'-trifluoromethylbenzyl | 2-butyl | nonafluorobutyl |
| 822 | benzyl | C(OCH$_2$CH$_3$)=N | 2-propyl | 4'-chlorobenzyl | 2-butyl | phenyl |
| 823 | benzyl | C(OCH$_2$CH$_3$)=N | 2-propyl | cyclohexylmethyl | 2-butyl | phenyl |
| 824 | benzyl | C(OCH$_2$CH$_3$)=N | cyclobutyl | benzyl | 2-butyl | phenyl |
| 825 | benzyl | C(OCH$_2$CH$_3$)=N | cyclobutylmethyl | benzyl | 2-(dimethylamino)ethyl | phenyl |
| 826 | benzyl | C(OCH$_3$)=N | cyclopropyl | benzyl | 2-butyl | phenyl |
| 827 | benzyl | CH$_2$CH$_2$ | 2-propyl | benzyl | benzyl | phenyl |
| 828 | benzyl | CH$_2$OCH$_2$ | 2-propyl | benzyl | CH$_2$CH$_2$OH | phenyl |
| 829 | benzyl | CH$_2$CHOH | 2-propyl | benzyl | cyclobutyl | phenyl |
| 830 | benzyl | CH$_2$O | 2-propyl | benzyl | cyclohexylmethyl | phenyl |
| 831 | benzyl | CH$_2$OH | 2-propyl | benzyl | cyclopropyl | trifluoromethyl |
| 832 | benzyl | CH=CH | 2-propyl | benzyl | 2-butyl | trifluoromethyl |
| 833 | benzyl | CHOHCH$_2$ | 2-propyl | benzyl | 2-butyl | trifluoromethyl |
| 834 | benzyl | CHOHCH$_2$ | 2-propyl | benzyl | 2-butyl | trifluoromethyl |
| 835 | benzyl | CHOHCHOH | 2-propyl | benzyl | 2-butyl | trifluoromethyl |
| 836 | benzyl | HN(=S)NH | 2-propyl | benzyl | 2-butyl | 2-pyridylethyl |
| 837 | benzyl | HNSO$_2$ | 2-butyl | benzyl | 2-butyl | benzyl |
| 838 | benzyl | HNSO$_2$NH | 2-butyl | benzyl | 2-butyl | benzyl |
| 839 | benzyl | N=N | 2-propyl | benzyl | 2-butyl | benzyl |
| 840 | benzyl | NH—NH | 2-butyl | benzyl | 2-butyl | benzyl |
| 841 | (—CH$_2$CH$_2$CH$_2$CH$_2$) | NHC(=O)NH | 2-butyl | benzyl | 2-butyl | n-propyl |
| 842 | (—CH$_2$CH$_2$OCH$_2$CH$_2$—) | NHC(=O)NH | 2-butyl | benzyl | 2-butyl | naphthyl |
| 843 | 2-hydroxyindanylmethyl | NHC(=O)NH | 2-butyl | benzyl | 2-butyl | phenyl |
| 844 | 3,5-dimethoxyphenyl | NHC(=O)NH | 2-butyl | benzyl | 2-butyl | thiophenyl |
| 845 | 3-hydroxy-n-propyl | NHC(=O)NH | 2-butyl | benzyl | cyclopropyl | trifluoromethyl |
| 846 | 4'-nitrobenzyl | NHC(=O)NH | 2-butyl | benzyl | 2-butyl | benzyl |
| 847 | 4-benzyloxyphenylmethyl | NHC(=O)NH | 2-butyl | benzyl | 2-butyl | 2-pyridylmethyl |
| 848 | 4-cyano-n-butyl | NHC(=O)NH | 2-butyl | benzyl | cyclobutyl | benzyl |
| 849 | 4-phenoxy- | NHC(=O)NH | 2-butyl | benzyl | cyclopropyl | benzyl |

TABLE XV-continued

| Ex. No. | R¹ | W | R³ | R⁴ | R⁸ | R¹⁰ |
|---|---|---|---|---|---|---|
| 850 | phenylmethyl | NHC(=O)NH | 2-butyl | benzyl | cyclobutyl | benzyl |
| 851 | 4-t-butylphenylmethyl | NHC(=O)NH | 2-butyl | benzyl | 2-propyl | benzyl |
| 852 | adamantyl | NHC(=O)NH | 2-butyl | benzyl | 2-butyl | methyl |
| 853 | benzyl | NHC(=O)NH | 2-butyl | benzyl | 2-butyl | phenylethyl |
| 854 | benzyl | NHC(=O)NH | 2-propyl | benzyl | 2-propyl | benzyl |
| 855 | benzyl | NHC(=O)NH | 2-propyl | 2-naphthylmethyl | 2-propyl | benzyl |
| 856 | benzyl | NHC(=O)NH | 2-propyl | 3-naphthylmethyl | benzyl | benzyl |
| 857 | benzyl | NHC(=O)NH | 2-propyl | 1-adamantylmethyl | 2-propyl | benzyl |
| 858 | benzyl | NHC(=O)NH | 2-propyl | 4'-hydroxybenzyl | 2-propyl | benzyl |
| 859 | benzyl | NHC(=O)NH | 2-propyl | 2-imidazolylethyl | 2-propyl | 2-pyridylmethyl |
| 860 | benzyl | NHC(=O)NH | 2-propyl | 4-pyridinylmethyl | 2-propyl | 3-methylpropyl |
| 861 | benzyl | NHC(=O)NH | 2-propyl | 4-bromophenyl | 2-propyl | benzyl |
| 862 | benzyl | NHC(=O)NH | 2-propyl | cycloheptylmethyl | 2-propyl | benzyl |
| 863 | benzyl | NHC(=O)NH | 2-propyl | 2-thiophenylmethyl | 2-butyl | 2-pyridylethyl |
| 864 | benzyl | NHC(=O)NH | 2-propyl | 3-pyrrazolylmethyl | 2-butyl | 3-naphthmethyl |
| 865 | benzyl | NHC(=O)NH | benzyl | benzyl | 2-butyl | 4'-t-butylbenzyl |
| 866 | benzyl | NHC(=O)NH | CH₂CF₃ | benzyl | cyclobutyl | benzyl |
| 867 | benzyl | NHC(=O)NH | CH₂CH₂C(=O)NH₂ | benzyl | cyclobutylmethyl | benzyl |
| 868 | benzyl | NHC(=O)NH | CH₂CH₂OH | benzyl | 2-butyl | benzyl |
| 869 | benzyl | NHC(=O)NH | CH₂CHOHCH₃ | benzyl | 2-butyl | benzyl |
| 870 | benzyl | NHC(=O)NH | cyclobutyl | benzyl | 2-propyl | benzyl |
| 871 | benzyl | NHC(=O)NH | cyclobutyl | benzyl | 2-propyl | benzyl |
| 872 | benzyl | NHC(=O)NH | cyclobutylmethyl | benzyl | 2-propyl | benzyl |
| 873 | benzyl | NHC(=O)NH | cyclopentylmethyl | benzyl | 2-propyl | benzyl |
| 874 | benzyl | NHC(=O)NH | cyclopropyl | benzyl | 2-propyl | benzyl |
| 875 | benzyl | NHC(=O)NH | cyclopropylmethyl | benzyl | 2-propyl | benzyl |
| 876 | cis-2-decahydronaphthylmethyl | NHC(=O)NH | 2-butyl | benzyl | 2-propyl | benzyl |
| 877 | cis-2-decahydronaphthylmethyl | NHC(=O)NH | 2-butyl | benzyl | 2-propyl | benzyl |

TABLE XV-continued

| Ex. No. | R¹ | W | R³ | R⁴ | R⁸ | R¹⁰ |
|---|---|---|---|---|---|---|
| 878 | benzyl | O | 2-propyl | benzyl | 2-propyl | benzyl |
| 879 | (CH₂CH₂CH)CH₂CH₂ | OC(=O)NH | 2-butyl | benzyl | 2-propyl | benzyl |
| 880 | 1-piperidylethyl | OC(=O)NH | 2-butyl | benzyl | 2-propyl | benzyl |
| 881 | 2-benzimidazolyl-methyl | OC(=O)NH | 2-butyl | benzyl | 2-propyl | benzyl |
| 882 | 2-naphthylmethyl | OC(=O)NH | 2-butyl | benzyl | 2-propyl | benzyl |
| 883 | 2-pyridylmethyl | OC(=O)NH | 2-butyl | benzyl | 2-propyl | benzyl |
| 884 | 2-quinazolinyl-methyl | OC(=O)NH | 2-butyl | benzyl | 2-propyl | benzyl |
| 885 | 3,4-methylene-dioxyphenylmethyl | OC(=O)NH | 2-butyl | benzyl | 2-propyl | benzyl |
| 886 | 3-chlorobenzyl | OC(=O)NH | 2-butyl | benzyl | cyclobutyl | benzyl |
| 887 | 3-phenylpropyl | OC(=O)NH | 2-butyl | benzyl | cyclobutyl-methyl | (CH₂CH₂OCH₂CH₂—) |
| 888 | 4'-acetamido-benzyl | OC(=O)NH | 2-butyl | benzyl | cyclopropyl | (CH₂CH₂OCH₂CH₂—) |
| 889 | 4-imidazolyl-methyl | OC(=O)NH | 2-butyl | benzyl | 2-propyl | 2-hydroxy-indanylmethyl |
| 890 | 4-methane-sulfonylbenzyl | OC(=O)NH | 2-butyl | benzyl | 2-propyl | 3,5-dimethoxy-phenyl |
| 891 | 4-methoxybenzyl | OC(=O)NH | 2-butyl | benzyl | 2-propyl | 3-hydroxy-n-propyl |
| 892 | 4-pyridylmethyl | OC(=O)NH | 2-butyl | benzyl | 2-propyl | 4'-nitro-benzyl |
| 893 | 4-trifluoro-methylbenzyl | OC(=O)NH | 2-butyl | benzyl | 2-propyl | 4-benzyl-oxyphenylmethyl |
| 894 | 9-fluorenyl-methyl | OC(=O)NH | 2-butyl | benzyl | 2-propyl | 4-cyano-n-butyl |
| 895 | adamantylmethyl | OC(=O)NH | 2-butyl | benzyl | 2-propyl | 4-phenoxy-phenylmethyl |
| 896 | benzyl | OC(=O)NH | 1-methoxy-2-propyl | benzyl | 2-propyl | 4-t-butyl-phenylmethyl |
| 897 | benzyl | OC(=O)NH | 2'-hydroxy-cyclopentylmethyl | benzyl | 2-propyl | adamantyl |
| 989 | benzyl | OC(=O)NH | 2,2,2-trichlor-oethyl | benzyl | 2-propyl | benzyl |
| 899 | benzyl | OC(=O)NH | 2,2,2-trifluor-oethyl | benzyl | 2-butyl | benzyl |
| 900 | benzyl | OC(=O)NH | 2-butyl | benzyl | 2-butyl | benzyl |
| 901 | benzyl | OC(=O)NH | 2-propyl | benzyl | 2-propyl | benzyl |
| 902 | benzyl | OC(=O)NH | 2-propyl | benzyl | 2-propyl | benzyl |
| 903 | benzyl | OC(=O)NH | 2-propyl | 3-naphth-ylmethyl | 2-butyl | benzyl |
| 904 | benzyl | OC(=O)NH | 2-propyl | 4'-phenoxy-benzyl | 2-propyl | benzyl |

TABLE XV-continued $$R^1-W\underset{R^3}{\overset{O}{\underset{\|}{C}}}\underset{H}{\overset{}{N}}\underset{R^4}{\overset{}{C}}\underset{OH}{\overset{}{C}}\underset{OH}{\overset{}{C}}\underset{R^4}{\overset{}{C}}\underset{H}{\overset{}{N}}\underset{\underset{R^8}{}}{\overset{O}{\underset{\|}{C}}}W-R^{10}$$

| Ex. No. | R¹ | W | R³ | R⁴ | R⁸ | R¹⁰ |
|---|---|---|---|---|---|---|
| 905 | benzyl | OC(=O)NH | 2-propyl | 4'-benzyl-oxybenzyl | 2-butyl | benzyl |
| 906 | benzyl | OC(=O)NH | 2-propyl | 4'-(5-tetra-zolyl)benzyl | 2-butyl | benzyl |
| 907 | benzyl | OC(=O)NH | 2-propyl | 3',5'-bis(tri-fluoremethyl)-benzyl | 2-butyl | benzyl |
| 908 | benzyl | OC(=O)NH | 2-propyl | 4'-trifluoro-methylbenzyl | 2-butyl | benzyl |
| 909 | benzyl | OC(=O)NH | 2-propyl | 2-phenylethyl | 2-butyl | benzyl |
| 910 | benzyl | OC(=O)NH | 2-propyl | 2-benzimi-dazolylmethyl | 2-butyl | benzyl |
| 911 | benzyl | OC(=O)NH | 2-propyl | 2-(4-chloro-phenyl)ethyl | 2-butyl | benzyl |
| 912 | benzyl | OC(=O)NH | 2-propyl | 2-decahydro-naphthylmethyl | 2-butyl | benzyl |
| 913 | benzyl | OC(=O)NH | 2-propyl | 2-(3,4-methylene-dioxyphenyl)ethyl | 2-butyl | benzyl |
| 914 | benzyl | OC(=O)NH | 3-(dimethyl-amino)-1-propyl | benzyl | 2-butyl | benzyl |
| 915 | benzyl | OC(=O)NH | CH₂NHC(=O)NHCH₃ | benzyl | 2-propyl | benzyl |
| 916 | benzyl | OC(=O)NH | CH₂NHSO₂CH₃ | benzyl | 2-propyl | benzyl |
| 917 | benzyl | OC(=O)NH | cyclobutyl | benzyl | 2-propyl | benzyl |
| 918 | benzyl | OC(=O)NH | cyclobutyl-methyl | benzyl | 2-propyl | benzyl |
| 919 | benzyl | OC(=O)NH | cyclopropyl | benzyl | 2-propyl | benzyl |
| 920 | benzyl | OC(=O)NH | cyclopropyl | benzyl | 2-propyl | benzyl |
| 921 | benzyl | OC(=O)NH | cyclopropyl-methyl | benzyl | 2-propyl | benzyl |
| 922 | benzyl | OC(=O)NH | methyl | benzyl | 2-propyl | cis-2-deca-hydronaphthyl-methyl |
| 923 | CH₃SO₂CH₂CH₂ | OC(=O)NH | 2-butyl | benzyl | 2-propyl | cis-2-deca-hydronaphthyl-methyl |
| 924 | cyclopentylethyl | OC(=O)NH | 2-butyl | benzyl | 2-propyl | benzyl |
| 925 | F₂HCOC₆H₄CH₂ | OC(=O)NH | 2-butyl | benzyl | 2-propyl | (CH₂CH₂CH)CH₂CH₂ 1-piperidyl-ethyl |
| 926 | benzyl | OCH₂ | 2-propyl | benzyl | 2-propyl | 2-benzimidazolyl-methyl |
| 927 | benzyl | OP(=O)(OMe)O | 2-propyl | benzyl | benzyl | 2-naphthyl-methyl |
| 928 | benzyl | SO₂ | 2-propyl | benzyl | CH₂CF₃ | 2-pyridyl methyl |
| 930 | 2,4-difluoro-phenyl | SO₂NH | 2-butyl | benzyl | CH₂CH₂C(=O)NH₂ | |

TABLE XV-continued structure: R¹—W—CH(R³)—C(=O)—NH—CH(R⁴)—CH(OH)—CH(OH)—CH(R⁴)—NH—C(=O)—CH(R⁸)—W—R¹⁰

| Ex. No. | R¹ | W | R³ | R⁴ | R⁸ | R¹⁰ |
|---|---|---|---|---|---|---|
| 931 | 4'-methylphenyl | SO₂NH | 2-butyl | benzyl | CH₂CH₂OH | 2-quinazolinylmethyl |
| 932 | benzyl | SO₂NH | 2-(methylaminoethyl | benzyl | CH₂CHOHCH₃ | 3,4-methylenedioxyphenylmethyl |
| 933 | benzyl | SO₂NH | 2-furanylmethyl | benzyl | cyclobutyl | 3-chlorobenzyl |
| 934 | benzyl | SO₂NH | 2-propyl | benzyl | cyclobutyl | 3-phenylpropyl |
| 936 | benzyl | SO₂NH | 2-propyl | benzyl | cyclobutylmethyl | 4'-acetamidobenzyl |
| 937 | benzyl | SO₂NH | 2-propyl | 3'-trifluoromethylbenzyl | cyclopentylmethyl | 4-imidazolylmethyl |
| 938 | benzyl | SO₂NH | 2-propyl | 2',4'-difluorobenzyl | cyclopropyl | 4-methanesulfonylbenzyl |
| 939 | benzyl | SO₂NH | 2-propyl | 3-phenylphenylpropyl | cyclopentylmethyl | 4-methoxybenzyl |
| 940 | benzyl | SO₂NH | 2-propyl | 1-pyrrolylethyl | 2-butyl | 4-pyridylmethyl |
| 941 | benzyl | SO₂NH | 2-propyl | 2-(4-chlorophenyl)ethyl | 2-butyl | 4-trifluoromethylbenzyl |
| 942 | benzyl | SO₂NH | 2-propyl | 1-phenylethyl | 2-propyl | 9-fluoroenylmethyl |
| 943 | benzyl | SO₂NH | 3-hydroxy-1-propyl | 1-phenylethyl | 2-butyl | adamantylmethyl |
| 944 | benzyl | SO₂NH | cyclobutyl | benzyl | 2-butyl | benzyl |
| 945 | benzyl | SO₂NH | cyclopropyl | benzyl | 2-butyl | benzyl |
| 946 | benzyl | SO₂NH | methylthiomethyl | 1-phenylethyl | 2-butyl | benzyl |
| 947 | cyclohexylethyl | SO₂NH | 2-butyl | benzyl | 2-butyl | benzyl |
| 948 | nonafluorobutyl | SO₂NH | 2-butyl | benzyl | 2-butyl | benzyl |
| 949 | phenyl | SO₂NH | 2-butyl | benzyl | 2-butyl | benzyl |
| 950 | trifluoromethyl | SO₂NH | 2-butyl | benzyl | 2-butyl | benzyl |
| 951 | 2,4-difluorophenyl | SO₂NHC(=O)NH | 2-butyl | benzyl | 2-butyl | benzyl |
| 952 | 4'-methylphenyl | SO₂NHC(=O)NH | 2-(dimethylaminoethyl | benzyl | 2-butyl | benzyl |
| 953 | 4'-methylphenyl | SO₂NHC(=O)NH | 2-butyl | benzyl | 2-butyl | benzyl |
| 954 | 4'-methylphenyl | SO₂NHC(=O)NH | 2-butyl | benzyl | 2-butyl | benzyl |
| 955 | 4'-methylphenyl | SO₂NHC(=O)NH | benzyl | benzyl | 2-butyl | benzyl |
| 956 | 4'-methylphenyl | SO₂NHC(=O)NH | CH₂CH₂OH | benzyl | 2-butyl | benzyl |
| 957 | 4'-methylphenyl | SO₂NHC(=O)NH | cyclobutyl | benzyl | 2-butyl | benzyl |
| 958 | 4'-methylphenyl | SO₂NHC(=O)NH | cyclohexylmethyl | benzyl | 2-butyl | benzyl |
| 959 | 4'-methylphenyl | SO₂NHC(=O)NH | cyclopropyl | benzyl | 2-butyl | benzyl |
| 960 | benzyl | SO₂NHC(=O)NH | 2-butyl | benzyl | 1-methoxy-2-propyl | benzyl |
| 961 | cyclohexylethyl | SO₂NHC(=O)NH | 2-butyl | benzyl | 2'-hydroxycyclopentylmethyl | benzyl |
| 962 | methyl | SO₂NHC(=O)NH | 2-butyl | benzyl | 2,2,2-trichloroethyl | benzyl |

TABLE XV-continued

| Ex. No. | R$^1$ | W | R$^3$ | R$^4$ | R$^8$ | R$^{10}$ |
|---|---|---|---|---|---|---|
| 963 | nonafluorobutyl | SO$_2$NHC(=O)NH | 2-butyl | benzyl | 2,2,2-trifluoroethyl | benzyl |
| 964 | phenyl | SO$_2$NHC(=O)NH | 2-butyl | benzyl | 2-butyl | benzyl |
| 965 | phenyl | SO$_2$NHC(=O)NH | 2-butyl | benzyl | 2-propyl | benzyl |
| 966 | phenyl | SO$_2$NHC(=O)NH | 2-butyl | 2'-chlorobenzyl | 2-propyl | benzyl |
| 967 | phenyl | SO$_2$NHC(=O)NH | 2-butyl | 3-naphthylmethyl | 2-propyl | benzyl |
| 968 | phenyl | SO$_2$NHC(=O)NH | 2-butyl | 2-(4-fluorophenyl)ethyl | 2-propyl | benzyl |
| 969 | phenyl | SO$_2$NHC(=O)NH | 2-butyl | 2-phenylethyl | 2-propyl | benzyl |
| 970 | phenyl | SO$_2$NHC(=O)NH | 2-butyl | 3'-carbomethoxybenzyl | 2-propyl | benzyl |
| 971 | phenyl | SO$_2$NHC(=O)NH | 2-butyl | benzyl | 2-propyl | CH$_3$SO$_2$CH$_2$CH$_2$ |
| 972 | phenyl | SO$_2$NHC(=O)NH | cyclopropyl | benzyl | 2-propyl | cyclophenylethyl |
| 973 | trifluoromethyl | SO$_2$NHC(=O)NH | 2-butyl | benzyl | 2-propyl | F$_2$HCOC$_6$H$_4$CH$_2$ |
| 974 | trifluoromethyl | SO$_2$NHC(=O)NH | 2-butyl | benzyl | 2-propyl | benzyl |
| 975 | trifluoromethyl | SO$_2$NHC(=O)NH | cyclobutyl | benzyl | 2-propyl | benzyl |
| 976 | trifluoromethyl | SO$_2$NHC(=O)NH | cyclopropyl | benzyl | 2-propyl | benzyl |

TABLE XVI

Structure: R¹-CH(R³)-W-C(=O)-NH-CH(R⁴)-CH(OH)-CH(OH)-CH(R⁴)-NH-C(=O)-O-R⁸

| Ex. No. | R¹ | W | R³ | R⁴ | R⁸ |
|---|---|---|---|---|---|
| 977 | 2-pyridylethyl | C(=O) | 2-propyl | benzyl | t-butyl |
| 978 | 2-pyridylmethyl | C(=O) | 2-butyl | 4-imidazolylmethyl | t-butyl |
| 979 | benzyl | C(=O) | 2-butyl | cyclohexylmethyl | t-butyl |
| 980 | 2-pyridyl-methyl | C(=O) | 2-propyl | benzyl | t-butyl |
| 981 | benzyl | C(=O) | 2-propyl | 2-pyridyl-methyl | t-butyl |
| 982 | 3-pyridyl-methyl | C(=O) | 2-propyl | benzyl | t-butyl |
| 983 | n-propyl | C(=O) | 2-propyl | benzyl | t-butyl |
| 984 | naphthyl | C(=O) | 2-propyl | 3-pyridyl-methyl | t-butyl |
| 985 | phenyl | C(=O) | 2-propyl | benzyl | t-butyl |
| 986 | thiophenyl | C(=O) | 2-propyl | benzyl | t-butyl |
| 987 | trifluoromethyl | C(=O) | 2-propyl | 3-pyridyl-methyl | t-butyl |
| 988 | benzyl | C(=O)CH₂ | 2-propyl | benzyl | t-butyl |
| 989 | 2-pyridylmethyl | C(=O)NH | 2-butyl | 2-pyridyl-methyl | t-butyl |
| 990 | benzyl | C(=O)NH | 2-butyl | 3-pyridyl-methyl | t-butyl |
| 991 | benzyl | C(=O)NH | 2-butyl | benzyl | t-butyl |
| 992 | benzyl | C(=O)NH | cyclobutyl | benzyl | t-butyl |
| 993 | benzyl | C(=O)NH | cyclobutylmethyl | benzyl | t-butyl |
| 994 | methyl | C(=O)NH | 2-butyl | 3-pyridyl-methyl | t-butyl |
| 995 | phenylethyl | C(=O)NH | 2-butyl | benzyl | t-butyl |
| 996 | benzyl | C(=O)NHNH | 2-propyl | 3-pyridyl-methyl | t-butyl |
| 997 | benzyl | C(=O)O | 2-propyl | benzyl | t-butyl |
| 998 | benzyl | C(=S) | 2-propyl | benzyl | t-butyl |
| 999 | benzyl | C(=S)NH | 2-propyl | 3-pyridyl-methyl | t-butyl |
| 1000 | benzyl | C(Cl)=N | 2-propyl | benzyl | t-butyl |
| 1001 | 2-pyridylmethyl | C(NHMe)=N | 2-propyl | benzyl | t-butyl |
| 1002 | 3-methylpropyl | C(NHMe)=N | 2-propyl | benzyl | t-butyl |
| 1003 | benzyl | C(NHMe)=N | 2-propyl | benzyl | t-butyl |
| 1004 | benzyl | C(NHMe)=N | 2-propyl | 3-pyridyl-methyl | t-butyl |
| 1005 | 2-pyridylethyl | C(OCH₂CH₂)=N | 2-propyl | benzyl | t-butyl |
| 1006 | 3-naphthylmethyl | C(OCH₂CH₂)=N | 2-propyl | benzyl | t-butyl |
| 1007 | 4'-t-butylbenzyl | C(OCH₂CH₂)=N | 2-propyl | 3-pyridyl-methyl | t-butyl |
| 1008 | benzyl | C(OCH₂CH₂)=N | 2-propyl | benzyl | t-butyl |
| 1009 | benzyl | C(OCH₂CH₂)=N | 2-propyl | 4'-ytrifluoromethylbenzyl | t-butyl |
| 1010 | benzyl | C(OCH₂CH₂)=N | 2-propyl | 4'-chlorobenzyl | t-butyl |
| 1011 | benzyl | C(OCH₂CH₂)=N | 2-propyl | cyclohexylmethyl | t-butyl |
| 1012 | benzyl | C(OCH₂CH₂)=N | cyclobutyl | benzyl | t-butyl |
| 1013 | benzyl | C(OCH₂CH₂)=N | cyclobutylmethyl | 3-pyridyl-methyl | t-butyl |
| 1014 | benzyl | C(OCH₂CH₂)=N | cyclopropyl | benzyl | t-butyl |
| 1015 | benzyl | C(OCH₂)=N | 2-propyl | benzyl | t-butyl |
| 1016 | benzyl | CH₂OCH₂ | 2-propyl | 3-pyridyl-methyl | t-butyl |
| 1017 | benzyl | CH₂CH₂ | 2-propyl | benzyl | t-butyl |
| 1018 | benzyl | CH₂CHOH | 2-propyl | 4-pyridyl-methyl | t-butyl |
| 1019 | benzyl | CH₂O | 2-propyl | benzyl | t-butyl |
| 1020 | benzyl | CH₂OH | 2-propyl | 2-pyridyl-methyl | t-butyl |
| 1021 | benzyl | CH=CH | 2-propyl | benzyl | t-butyl |
| 1022 | benzyl | CHOHCH₂ | 2-propyl | 3-pyridyl-methyl | t-butyl |
| 1023 | benzyl | CHOHCHOH | 2-propyl | benzyl | t-butyl |
| 1024 | benzyl | HNC(=S)NH | 2-propyl | 4-pyridyl-methyl | t-butyl |
| 1025 | benzyl | HNSO₂ | 2-butyl | benzyl | t-butyl |
| 1026 | benzyl | HNSO₂NH | 2-butyl | benzyl | t-butyl |
| 1027 | benzyl | N=N | 2-propyl | benzyl | t-butyl |
| 1028 | benzyl | NH—NH | 2-propyl | 4-pyridyl-methyl | t-butyl |
| 1029 | (—CH₂CH₂CH₂CH₂CH₂—) | NHC(=O)NH | 2-butyl | benzyl | t-butyl |
| 1030 | (—CH₂CH₂OCH₂CH₂—) | NHC(=O)NH | 2-butyl | 4-pyridyl-methyl | t-butyl |
| 1031 | 2-hydroxyindanyl-methyl | NHC(=O)NH | 2-butyl | benzyl | t-butyl |
| 1032 | 3,5-dimethoxyphenyl | NHC(=O)NH | 2-butyl | 4-pyridyl-methyl | t-butyl |
| 1033 | 3-hydroxy-n-propyl | NHC(=O)NH | 2-butyl | benzyl | t-butyl |
| 1034 | 4'-nitrobenzyl | NHC(=O)NH | 2-butyl | benzyl | t-butyl |
| 1035 | 4-benzyloxyphenylmethyl | NHC(=O)NH | 2-butyl | 4-pyridyl-methyl | t-butyl |
| 1036 | 4-cyano-n-butyl | NHC(=O)NH | 2-butyl | benzyl | t-butyl |
| 1037 | 4-phenoxyphenyl-methyl | NHC(=O)NH | 2-butyl | benzyl | t-butyl |
| 1038 | 4-t-butylphenyl-methyl | NHC(=O)NH | 2-butyl | benzyl | t-butyl |
| 1039 | adamantyl | NHC(=O)NH | 2-butyl | benzyl | t-butyl |
| 1040 | benzyl | NHC(=O)NH | 2-butyl | 4-pyridyl-methyl | t-butyl |
| 1041 | benzyl | NHC(=O)NH | 2-butyl | benzyl | t-butyl |
| 1042 | benzyl | NHC(=O)NH | 2-propyl | 3-pyridyl-methyl | t-butyl |
| 1043 | benzyl | NHC(=O)NH | 2-propyl | 2-naphthylmethyl | t-butyl |
| 1044 | benzyl | NHC(=O)NH | 2-propyl | 3-naphthylmethyl | t-butyl |
| 1045 | benzyl | NHC(=O)NH | 2-propyl | 1-adamantylmethul | t-butyl |
| 1046 | benzyl | NHC(=O)NH | 2-propyl | 4'-hydroxybenzyl | 2-propyl |
| 1047 | benzyl | NHC(=O)NH | 2-propyl | 2-imidazolylethyl | 2-propyl |
| 1048 | benzyl | NHC(=O)NH | 2-propyl | 4-pyridinylmethyl | 2-propyl |
| 1049 | benzyl | NHC(=O)NH | 2-propyl | 4-bromophenyl | 2-propyl |
| 1050 | benzyl | NHC(=O)NH | 2-propyl | cycloheptylmethyl | 2-propyl |

TABLE XVI-continued $$R^1-\overset{W}{\underset{R^3}{CH}}-\overset{O}{\underset{}{C}}-\overset{H}{\underset{}{N}}-CH(R^4)-CH(OH)-CH(OH)-CH(R^4)-\overset{H}{\underset{}{N}}-\overset{O}{\underset{}{C}}-O-R^8$$

| Ex. No. | R¹ | W | R³ | R⁴ | R⁸ |
|---|---|---|---|---|---|
| 1051 | benzyl | NHC(=O)NH | 2-propyl | 2-thiophenylmethyl | 2-propyl |
| 1052 | benzyl | NHC(=O)NH | 2-propyl | 3-pyrrazolylmethyl | 2-propyl |
| 1053 | benzyl | NHC(=O)NH | benzyl | benzyl | 2-propyl |
| 1054 | benzyl | NHC(=O)NH | CH₂CF₃ | benzyl | 2-propyl |
| 1055 | benzyl | NHC(=O)NH | CH₂CH₂C(=O)NH₂ | benzyl | 2-propyl |
| 1056 | benzyl | NHC(=O)NH | CH₂CH₂OH | benzyl | 2-propyl |
| 1057 | benzyl | NHC(=O)NH | CH₂CHOHCH₂ | benzyl | 2-propyl |
| 1058 | benzyl | NHC(=O)NH | cyclobutyl | 4-pyridyl-methyl | 2-propyl |
| 1059 | benzyl | NHC(=O)NH | cyclobutyl | benzyl | 2-propyl |
| 1060 | benzyl | NHC(=O)NH | cyclobutylmethyl | benzyl | 2-propyl |
| 1061 | benzyl | NHC(=O)NH | cyclopentylmethyl | 3-pyridyl-methyl | 2-propyl |
| 1062 | benzyl | NHC(=O)NH | cyclopropyl | benzyl | 2-propyl |
| 1063 | benzyl | NHC(=O)NH | cyclopropylmethyl | benzyl | 2-propyl |
| 1064 | cis-2-decahydronaphthylmethyl | NHC(=O)NH | 2-butyl | 3-pyridyl-methyl | 2-propyl |
| 1065 | cis-2-decahydronaphthylmethyl | NHC(=O)NH | 2-butyl | benzyl | 2-propyl |
| 1066 | benzyl | O | 2-propyl | benzyl | 2-propyl |
| 1067 | (CH₂CH₂CH)CH₂CH₂ | OC(=O)NH | 2-butyl | 3-pyridyl-methyl | 2-propyl |
| 1068 | 1-piperidylethyl | OC(=O)NH | 2-butyl | benzyl | 2-propyl |
| 1069 | 2-benzimidazolylmethyl | OC(=O)NH | 2-butyl | benzyl | 2-propyl |
| 1070 | 2-naphthylmethyl | OC(=O)NH | 2-butyl | benzyl | 2-propyl |
| 1071 | 2-pyridylmethyl | OC(=O)NH | 2-butyl | 3-pyridyl-methyl | 2-propyl |
| 1072 | 2-quinazolinylmethyl | OC(=O)NH | 2-butyl | benzyl | 2-propyl |
| 1073 | 3,4-methylenedioxyphenylmethyl | OC(=O)NH | 2-butyl | benzyl | 2-propyl |
| 1074 | 3-chlorobenzyl | OC(=O)NH | 2-butyl | benzyl | 2-propyl |
| 1075 | 3-phenylpropyl | OC(=O)NH | 2-butyl | 3-pyridyl-methyl | 2-propyl |
| 1076 | 4'-acetamidobenzyl | OC(=O)NH | 2-butyl | benzyl | 2-propyl |
| 1077 | 4-imidazolylmethyl | OC(=O)NH | 2-butyl | benzyl | 2-propyl |
| 1078 | 4-methanesulfonylbenzyl | OC(=O)NH | 2-butyl | benzyl | 2-propyl |
| 1079 | 4-methoxybenzyl | OC(=O)NH | 2-butyl | benzyl | 2-propyl |
| 1080 | 4-pyridylmethyl | OC(=O)NH | 2-butyl | benzyl | 2-propyl |
| 1081 | 4-trifluoromethylbenzyl | OC(=O)NH | 2-butyl | benzyl | 2-propyl |
| 1082 | 9-fluorenylmethyl | OC(=O)NH | 2-butyl | benzyl | 2-propyl |
| 1083 | adamantylmethyl | OC(=O)NH | 2-butyl | benzyl | iso-butyl |
| 1084 | benzyl | OC(=O)NH | 1-methoxy-2-propyl | benzyl | iso-butyl |
| 1085 | benzyl | OC(=O)NH | 2'-hydroxycyclopentylmethyl | benzyl | iso-butyl |
| 1086 | benzyl | OC(=O)NH | 2,2,2-trichloroethyl | benzyl | iso-butyl |
| 1087 | benzyl | OC(=O)NH | 2,2,2-trifluoroethyl | benzyl | iso-butyl |
| 1088 | benzyl | OC(=O)NH | 2-butyl | benzyl | iso-butyl |
| 1089 | benzyl | OC(=O)NH | 2-propyl | 3-pyridyl-methyl | iso-butyl |
| 1090 | 3-pyridyl-methyl | OC(=O)NH | 2-propyl | benzyl | iso-butyl |
| 1091 | 3-pyridyl-methyl | OC(=O)NH | 2-propyl | 3-naphthylmethyl | iso-butyl |
| 1092 | benzyl | OC(=O)NH | 2-propyl | 4'-phenoxybenzyl | iso-butyl |
| 1093 | benzyl | OC(=O)NH | 2-propyl | 4'-benzyloxybenzyl | iso-butyl |
| 1094 | benzyl | OC(=O)NH | 2-propyl | 4'-(5-tetrazolyl)benzyl | iso-butyl |
| 1095 | benzyl | OC(=O)NH | 2-propyl | 3',5'-bis(trifluoremethyl)benzyl | iso-butyl |
| 1096 | benzyl | OC(=O)NH | 2-propyl | 4'-trifluoromethylbenzyl | iso-butyl |
| 1097 | benzyl | OC(=O)NH | 2-propyl | 2-phenylethyl | iso-butyl |
| 1098 | benzyl | OC(=O)NH | 2-propyl | 2-benzimidazolylmethyl | iso-butyl |
| 1099 | benzyl | OC(=O)NH | 2-propyl | 2-(4-chlorophenyl)ethyl | iso-butyl |
| 1100 | benzyl | OC(=O)NH | 2-propyl | 2-decahydronaphthylmethyl | iso-butyl |
| 1101 | benzyl | OC(=O)NH | 2-propyl | 2-(3,4-methylenedioxyphenyl)ethyl | iso-butyl |
| 1102 | benzyl | OC(=O)NH | 3-(dimethylamino)-1-propyl | benzyl | iso-butyl |
| 1103 | benzyl | OC(=O)NH | benzyl | benzyl | iso-butyl |
| 1104 | benzyl | OC(=O)NH | CH₂NHC(=O)NHCH₂ | 3-pyridyl-methyl | iso-butyl |
| 1105 | benzyl | OC(=O)NH | CH₂NHSO₂CH₂ | benzyl | iso-butyl |
| 1106 | benzyl | OC(=O)NH | cyclobutyl | 3-pyridyl-methyl | iso-butyl |
| 1107 | benzyl | OC(=O)NH | cyclobutylmethyl | benzyl | iso-butyl |
| 1108 | benzyl | OC(=O)NH | cyclopropyl | benzyl | iso-butyl |
| 1109 | benzyl | OC(=O)NH | cyclopropylmethyl | 3-pyridyl-methyl | iso-butyl |
| 1110 | benzyl | OC(=O)NH | methyl | benzyl | iso-butyl |
| 1111 | CH₂SO₂CH₂CH₂ | OC(=O)NH | 2-butyl | 3-pyridyl-methyl | iso-butyl |
| 1112 | cyclopentylethyl | OC(=O)NH | 2-butyl | benzyl | iso-butyl |
| 1113 | F2HCOC6H4CH2 | OC(=O)NH | 2-butyl | 3-pyridyl-methyl | iso-butyl |
| 1114 | benzyl | OCH₂ | 2-propyl | benzyl | iso-butyl |
| 1115 | benzyl | OP(=O)(OMe)O | 2-propyl | 3-pyridyl-methyl | iso-butyl |
| 1116 | benzyl | SO₂ | 2-propyl | benzyl | iso-butyl |
| 1117 | 2,4-difluorophenyl | SO₂NH | 2-butyl | benzyl | iso-butyl |
| 1118 | 4'-methylphenyl | SO₂NH | 2-butyl | benzyl | iso-butyl |
| 1119 | benzyl | SO₂NH | 2-(methylamino)ethyl | benzyl | iso-butyl |
| 1120 | benzyl | SO₂NH | 2-furanylmethyl | benzyl | iso-butyl |
| 1121 | 3-pyridyl-methyl | SO₂NH | 2-propyl | 3-pyridyl-methyl | iso-butyl |

TABLE XVI-continued structure: R¹-W-CH(R³)-C(=O)-NH-CH(R⁴)-CH(OH)-CH(OH)-CH(R⁴)-NH-C(=O)-O-R⁸

| Ex. No. | R¹ | W | R³ | R⁴ | R⁸ |
|---|---|---|---|---|---|
| 1122 | benzyl | SO₂NH | 2-propyl | benzyl | t-butyl |
| 1123 | 3-pyridyl-methyl | SO₂NH | 2-propyl | 3'-trifluoromethylbenzyl | |
| 1124 | benzyl | SO₂NH | 2-propyl | 2',4'-difluorobenzyl | t-butyl |
| 1125 | benzyl | SO₂NH | 2-propyl | 3-phenylpropyl | t-butyl |
| 1126 | benzyl | SO₂NH | 2-propyl | 1-pyrrolylethyl | t-butyl |
| 1127 | 2-pyridyl-methyl | SO₂NH | 2-propyl | 2-(4-chlorophenyl)ethyl | t-butyl |
| 1128 | benzyl | SO₂NH | 2-propyl | 1-phenylethyl | t-butyl |
| 1129 | 3-pyridyl-methyl | SO₂NH | 3-hydroxy-1-propyl | 1-phenylethyl | t-butyl |
| 1130 | benzyl | SO₂NH | cyclobutyl | benzyl | t-butyl |
| 1131 | benzyl | SO₂NH | cyclopropyl | benzyl | t-butyl |
| 1132 | benzyl | SO₂NH | methylthiomethyl | 1-phenylethyl | t-butyl |
| 1133 | 2-pyridyl-methyl | SO₂NH | 2-butyl | benzyl | t-butyl |
| 1134 | nonafluorobutyl | SO₂NH | 2-butyl | benzyl | t-butyl |
| 1135 | phenyl | SO₂NH | 2-butyl | benzyl | t-butyl |
| 1136 | trifluoromethyl | SO₂NH | 2-butyl | benzyl | t-butyl |
| 1137 | 2,4-difluorophenyl | SO₂NHC(=O)NH | 2-butyl | benzyl | t-butyl |
| 1138 | 4'-methylphenyl | SO₂NHC(=O)NH | 2-(dimethylamino)ethyl | benzyl | t-butyl |
| 1139 | 4'-methylphenyl | SO₂NHC(=O)NH | 2-butyl | 2-pyridyl-methyl | t-butyl |
| 1140 | 4'-methylphenyl | SO₂NHC(=O)NH | 2-butyl | benzyl | t-butyl |
| 1141 | 4'-methylphenyl | SO₂NHC(=O)NH | benzyl | 2-pyridyl-methyl | t-butyl |
| 1142 | 4'-methylphenyl | SO₂NHC(=O)NH | CH₂CH₂OH | benzyl | t-butyl |
| 1143 | 4'-methylphenyl | SO₂NHC(=O)NH | cyclobutyl | benzyl | t-butyl |
| 1144 | 4'-methylphenyl | SO₂NHC(=O)NH | cyclohexylmethyl | benzyl | t-butyl |
| 1145 | 4'-methylphenyl | SO₂NHC(=O)NH | cyclopropyl | 2-pyridyl-methyl | t-butyl |
| 1146 | benzyl | SO₂NHC(=O)NH | 2-butyl | benzyl | t-butyl |
| 1147 | cyclohexylethyl | SO₂NHC(=O)NH | 2-butyl | benzyl | t-butyl |
| 1148 | methyl | SO₂NHC(=O)NH | 2-butyl | benzyl | t-butyl |
| 1149 | nonafluorobutyl | SO₂NHC(=O)NH | 2-butyl | 2-pyridyl-methyl | t-butyl |
| 1150 | phenyl | SO₂NHC(=O)NH | 2-butyl | benzyl | t-butyl |
| 1151 | phenyl | SO₂NHC(=O)NH | 2-butyl | benzyl | t-butyl |
| 1152 | phenyl | SO₂NHC(=O)NH | 2-butyl | 2'-chlorobenzyl | t-butyl |
| 1153 | phenyl | SO₂NHC(=O)NH | 2-butyl | 3-naphthylmethyl | t-butyl |
| 1154 | phenyl | SO₂NHC(=O)NH | 2-butyl | 2-(4-fluorophenyl)ethyl | t-butyl |
| 1155 | phenyl | SO₂NHC(=O)NH | 2-butyl | 2-phenylethyl | t-butyl |
| 1156 | phenyl | SO₂NHC(=O)NH | 2-butyl | 3'-carbomethoxybenzyl | t-butyl |
| 1157 | phenyl | SO₂NHC(=O)NH | 2-butyl | benzyl | t-butyl |
| 1158 | phenyl | SO₂NHC(=O)NH | cyclopropyl | 2-pyridyl-methyl | t-butyl |
| 1159 | trifluoromethyl | SO₂NHC(=O)NH | 2-butyl | benzyl | t-butyl |
| 1160 | trifluoromethyl | SO₂NHC(=O)NH | 2-butyl | benzyl | t-butyl |
| 1161 | trifuloromethyl | SO₂NHC(=O)NH | cyclobutyl | 2-pyridyl-methyl | t-butyl |
| 1162 | trifluoromethyl | SO₂NHC(=O)NH | cyclopropyl | benzyl | t-butyl |
| 1163 | Benzimidazolylmethyl | N(CH₂)C(=O)NH | 2-propyl | 4-pyridyl-methyl | t-butyl |
| 1164 | Benzimidazolylmethyl | NC(=O)NH | 2-propyl | 4-pyridyl-methyl | t-butyl |
| 1165 | (CH₂)2NCH—(CH₂) | C(=O)NH | 2-propyl | 4-fluoro-benzyl | t-butyl |
| 1166 | 2-amino-2-propyl | C(=O)NH | CF₃ | benzyl | t-butyl |
| 1167 | dimethylaminomethyl | C(=O)NH | 2-propyl | benzyl | t-butyl |
| 1168 | dimethylaminomethyl | C(=O)NH | 2-propyl | benzyl | t-propyl |
| 1169 | 4-amino-benzyl | C(=O)NH | 2-propyl | benzyl | t-butyl |

Standard procedures were used for detecting and comparing the activity of the compounds of this invention. The results are summarized in Table VII.

CELL FREE PROTEASE INHIBITION ASSAY

Materials

HIV gag polyprotein corresponding to all of p17 and 78 amino acids of p24, produced by in vitro translation using rabbit reticulocyte lysate and mRNA prepared in vitro from plasmid encoding full length gag polyprotein linerized with the restriction enzyme Pst 1. (See S. Erickson-Viitanen et al., Aids Research and Human Retroviruses, 5 (6), 577 (1989) for plasmid construction, and basis for assay).

Source of protease: Either (A) crude E. coli lysate of bacteria harboring a plasmid containing HIV protease under the control of the lac promotor, used at a final concentration of 0.5 mg/ml, or (B) inclusion bodies of E. coli harboring plasmid containing HIV protease under the control of the T7 promotor (Cheng et al., Gene, in press (1990). Such inclusion bodies were solubilized in 8M urea, 50 mM Tris pH 8.0. Protease activity was recovered by dilution of the inclusion bodies 20-fold in buffer containing 50 mM Sodium Acetate, pH 5.5, 1 mM EDTA, 10% glycerol and 5% ethylene glycol. This protease source was used at a final concentration of 0.00875 mg/ml.

Inhibitory compounds were dissolved in sufficient DMSO to make a 25 mM stock concentration. All further dilutions were done in DMSO.

Set Up

Into sterile test tubes were placed the following:
1 uL inhibitor dilutions
14 ul HIV protease in Phosphate Buffered Saline (Gibco)
5 ul of in vitro translation products.

Reactions were incubated at 30° C., then quenched by the addition of Sample buffer. See U. K. Laemmli, Nature, 1970, 227:680–685.

One fourth of each sample was analyzed on an 8–16% gradient denaturing acrylamide gel (Novex, Inc), according to Laemmli. Following electrophoresis, gels were fixed, impregnated with Enhance (Du Pont NEN, Boston, Mass.) and dried according to manufacturers instructions (NEN). Dried fluorographs were exposed to film and/or quantitated using an Ambis radioanalytic scanner.

Each group of test compounds was compared to the values obtained for pepstatin, a well known inhibitor of acid proteases. Inhibitory concentration for 50% inhibition ($IC_{50}$) is determined from plots of log concentration inhibitor versus % inhibition of protease activity.

Biological Activity: $IC_{50}$ is the concentration necessary for reducing the activity of the enzyme by 50%.

HIV YIELD REDUCTION CELL ASSAY

Materials

MT2, a human T-cell line, was cultured in RPMI medium supplemented with 5% (v/v) heat inactivated fetal calf serum (FCS), L-glutamine and gentamycin. Human immunodeficiency virus strains, HIV(3B) and HIV(Rf) were propagated in H-9 cells in RPMI with 5% FCS. Poly-L-lysine (Sigma) coated cell culture plates were prepared according to the method of Harada et al. (Science 1985 229:563–566). MTT, 3-(4,5-dimethylthiazol-2yl)-2,5-diphenyltetrazolium bromide, was obtained from Sigma.

Method

Test compounds were dissolved in dimethylsulfoxide to 5 mg/ml and serially diluted into RPMI medium to ten times the desired final concentration. MT-2 cells ($5 \times 10E5$/ml) in 2.3 ml were mixed with 0.3 ml of the appropriate test compound solution and allowed to sit for 30 minutes at room temperature. HIV(3b) or HIV(Rf) ($\sim 5 \times 10E5$ plaque forming units/ml) in 0.375 ml was added to the cell and compound mixtures and incubated for one hour at 36° C. The mixtures were centrifuged at 1000 rpm for 10 minutes and the supernatants containing unattached virus were discarded. The cell pellets were suspended in fresh RPMI containing the appropriate concentrations of test compound and placed in a 36° C., 4% $CO_2$ incubator. Virus was allowed to replicate for 3 days. Cultures were centrifuged for 10 minutes at 1000 rpm and the supernatants containing cell free progeny virus were removed for plaque assay.

The virus titers of the progeny virus produced in the presence or absence of test compounds were determined by plaque assay. Progeny virus suspensions were serially diluted in RPMI and 1.0 ml of each dilution was added to 9 ml of MT-2 cells in RPMI. Cells and virus were incubated for 3 hours at 36° C. to allow for efficient attachment of the virus to cells. Each virus and cell mixture was aliquoted equally to two wells of a six well poly-L-lysine coated culture plate and incubated overnight at 36° C., 4% $CO_2$. Liquid and unattached cells were removed prior to the addition of 1.5 ml of RPMI with 0.75% (w/v) Seaplaque agarose (FMC Corp) and 5% FCS. Plates were incubated for 3 days and a second RPMI/agarose overlay was added. After an additional 3 days at 36° C., 4% $CO_2$, a final overlay of phosphate-buffered saline with 0.75% Seaplaque agarose and 1 mg MTT/ml was added. The plates were incubated overnight at 36° C. Clear plaques on a purple background were counted and the number of plaque forming units of virus was calculated for each sample. The antiviral activity of test compounds was determined by the percent reduction in the virus titer with respect to virus grown in the absence of any inhibitors.

HIV LOW MULTIPLICITY ASSAY

Materials

MT-Z2, a human T-cell line, was cultured in RPMI medium supplemented with 5% (v/v) heat inactivated fetal calf serum (FCS), L-glutamine and gentamycin (GIBCO). Human immunodeficiency virus strains HIV(3b) and HIV (Rf) were propagated in H-9 cells in RPMI with 5% FCS. XTT, benzene-sulfonic acid, 3,3'-[1-[(phenylamino)carbonyl]-3,4-tetrazolium]bis(4-methoxy-6-nitro)-, sodium salt, was obtained from Starks Associates, Inc.

Method

Test compounds were dissolved in dimethyl-sulfoxide to 5 mg/ml and serially diluted into RPMI medium to ten times the desired final concentration. MT-2 cells ($5 \times 10E4$/0.1 ml) were added to each well of a 96 well culture plate and 0.02 ml of the appropriate test compound solution was added to the cells such that each compound concentration was present in two wells. The cells and compounds were allowed to sit for 30 minutes at room temperature. HIV(3b) or HIV(Rf) ($\sim 5 \times 10E5$ plaque forming units/ml) was diluted in medium and added to the cell and compound mixtures to give a multiplicity of infection of 0.01 plaque forming unit/cell. The mixtures were incubated for 7 days at 36° C., during which time the virus replicated and caused the death of unprotected cells. The percentage of cells protected from virus induced cell death was determined by the degree of metabolism of the tetrazolium dye, XTT. In living cells, XTT was metabolized to a colored formazan product which was quantitated spectrophoto-metrically at 450 rm. The amount of colored formazan was proportional to the number of cells protected from virus by the test compound. The concentration of compound protecting either 50% ($IC_{50}$) or 90% ($IC_{90}$) with respect to an uninfected cell culture was determined.

TABLE XVII

| Compound # | Cell Free Assay | Cell Assay $IC_{50}$ | Cell Assay $IC_{90}$ |
|---|---|---|---|
| Example 1A | 12 | 2* | 6* |
| Example 1B | 37 | 5* | NA |
| Example 2A | 12 | 10 | 30 |
| Example 2B | 0.17 | 1.9 | 3.0 |
| Example 2C | 31 | — | — |
| Example 3 | 383 | — | — |
| Example 4 | 435 | — | — |
| Example 5 | 65 | — | — |
| Example 6 | 4.8 | NA | NA |
| Example 7 | 502 | — | — |
| Example 8 | 590 | — | — |
| Example 9 | 0.52 | NA | NA |
| Example 10 | 600 | — | — |
| Example 11 | 20 | NA | NA |
| Example 12 | 4.1 | NA | NA |
| Example 13 | 3.3 | 2.3 | 25 |
| Example 14 | 480 | NA | NA |
| Example 15 | 260 | — | — |
| Example 16 | 260 | — | — |
| Example 17 | 278 | — | — |
| Example 18 | 2.3 | 6* | 12* |
| Example 20 | 0.01 | <1 | <1 |

TABLE XVII-continued

| Compound # | Cell Free Assay | Cell Assay IC$_{50}$ | IC$_{90}$ |
|---|---|---|---|
| Example 21 | 0.002 | 6 | — |

What is claimed is:

1. There is provided by this invention a compound of the formula:

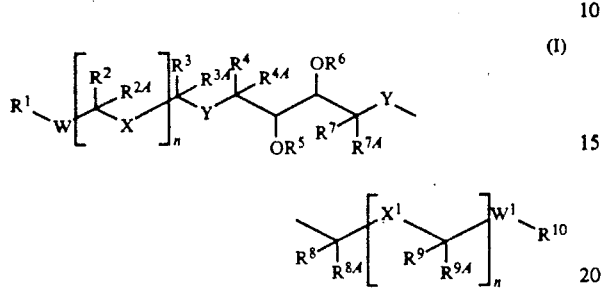

wherein:

R$^1$ through R$^7$ through R$^{10}$ are independently selected from the following groups:
hydrogen;
C$_1$–C$_8$ alkyl substituted with 0–3 R$^{11}$;
C$_2$–C$_8$ alkenyl substituted with 0–3 R$^{11}$;
C$_3$–C$_8$ alkynyl substituted with 0–3 R$^{11}$;
C$_3$–C$_8$ cycloalkyl substituted with 0–3 R$^{11}$;
C$_6$–C$_{10}$ bicycloalkyl substituted with 0–3 R$^{11}$;
aryl substituted with 0–3 R$^{12}$;
a C$_6$–C$_{14}$ carbocyclic residue substituted with 0–3 R$^{12}$;
a heterocyclic ring system substituted with 0–2 R$^{12}$ selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, pyrrolidinyl, tetrahydrofuranyl, tetrahydroquinolinyl, tetrahydroisoquinolinyl, or decahydroisoquinolinyl;

R$^{2A}$ through R$^{4A}$ and R$^{7A}$ are independently selected from the following groups:
hydrogen;
C$_1$–C$_4$ alkyl substituted with halogen or C$_1$–C$_2$ alkoxy;
benzyl substituted with halogen or C$_1$–C$_2$ alkoxy;

R$^5$ and R$^6$ are independently selected from the following groups:
hydrogen:
C$_1$–C$_6$ alkoxycarbonyl;
C$_1$–C$_6$ alkylcarbonyl;
benzoyl;
phenoxycarbonyl; or
phenylaminocarbony; wherein said alkyl residues are substituted with 0–3 R$^{11}$, and said aryl residues are substituted with 0–3 R$^{12}$; or any other group that, when administered to a mammalian subject, cleaves to form the original diol in which R$^5$ and R$^6$ are hydrogen;

R$^{11}$ is selected from one or more of the following:
keto, halogen, cyano, —NR$^{13}$R$^{14}$, —CO$_2$R$^{13}$, —OC(=O)R$^{13}$, —OR$^{13}$, C$_2$–C$_6$ alkoxyalkyl, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$—, NR$^{14}$C(=O)OR$^{14}$, OC(=O)NR$^{13}$R$^{14}$, —NR$^{13}$C(=O)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, C$_1$–C$_4$ alkyl, C$_2$–C$_4$ alkenyl, C$_3$–C$_6$ cycloalkyl, C$_3$–C$_6$ cycloalkylmethyl;
a C$_5$–C$_{14}$ carbocyclic residue substituted with 0–3 R$^{12}$;
aryl substituted with 0–3 R$^{12}$;
or a heterocyclic ring system substituted with 0–2 R$^{12}$ selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, pyrrolidinyl, tetrahydrofuranyl, tetrahydroquinolinyl, tetrahydroisoquinolinyl, or decahydroisoquinolinyl;

R$^{12}$, when a substituent on carbon, is selected from one or more of the following:
phenyl, benzyl, phenethyl, phenoxy, benzyloxy, halogen, hydroxy, nitro, cyano, C$_1$–C$_4$ alkyl, C$_3$–C$_6$ cycloalkyl, C$_3$–C$_6$ cycloalkylmethyl, C$_7$–C$_{10}$ arylalkyl, alkoxy, —NR$^{13}$R$^{14}$, C$_2$–C$_6$ alkoxyalkyl, C1–C4 hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —S(O)$_m$R$^{13}$, —SO$_2$NR$^{13}$R$^{14}$, —NHSO$_2$R$^{14}$;

or R$^{12}$ may be a 3- or 4-carbon chain attached to adjacent carbons on the ring to form a fused 5- or 6-membered ring, said 5- or 6-membered ring being optionally substituted on the aliphatic carbons with halogen, C$_1$–C$_4$ alkyl, C$_1$–C$_4$ alkoxy, hydroxy, or NR$^{13}$R$^{14}$; or, when R$^{12}$ is attached to a saturated carbon atom it may be carbonyl or thiocarbonyl;

and R$^{12}$, when a substituent on nitrogen, is selected from one or more of the following:
phenyl, benzyl, phenethyl, hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethyl, —NR$^{13}$R$^{14}$, C$_2$–C$_6$ alkoxyalkyl, C$_1$–C$_4$ haloalkyl, C$_1$–C$_4$ alkoxycarbonyl, C$_1$–C$_4$ alkylcarbonyloxy, C$_1$–C$_4$ alkylcarbonyl, R$^{13}$ is H, phenyl, benzyl or C$_1$–C$_6$ alkyl;
R$^{14}$ is H or C$_1$–C$_4$ alkyl;
or R$^{13}$R$^{14}$ can join to form (CH$_2$)$_4$, (CH$_2$)$_5$, (CH$_2$CH$_2$N(R$^{15}$)CH$_2$CH$_2$), or (CH$_2$CH$_2$OCH$_2$CH$_2$);
R$^{15}$ is H or CH$_3$;
m is 0, 1 or 2;
n and n$^1$ are independently 0 or 1;
W and W1 are independently selected from the following:
—NR$^{16}$C(=Q)NR$^{16}$;
—C(=Q)NR$^{16}$—;
—C(=Q)O—;
—NR$^{16}$C(=Q)O—;
—OC(=Q)NR$^{16}$—;
—NR$^{16}$C(=Q)—;
—C(=Q)—;
—C(=Q)CH$_2$—;
—NR$^{16}$SO$_2$NR$^{16}$—
—NR$^{16}$SO$_2$—
—SO$_2$NR$^{16}$—
—SO$_2$—;
—QCH$_2$—;
—Q—;
—(CH$_2$)$_p$NR$^{16}$—;
—CH$_2$CH$_2$—;

—CH=CH—;
—CH(OH)CH(OH)—;
—CH(OH)CH2—;
—CH2CH(OH)—;
—CH(OH)—;
—NH—NH—;
—C(=O)NH—NH—;
—C(Cl)=N—;
—C(—OR$^{16}$)=N—;
—C(—NR$^{16}$R$^{17}$)=N—;
—OP(=O)(Q$^1$R$^{16}$)O—;
—P(=O)(Q$^1$R$^{16}$)O—;
—SO$_2$NHC(=O)NH—;

X and X$^1$ are independently selected from the following:
—C(=Q)NR$^{16}$—;
—C(=Q)O—;
—C(=Q)—;
—CH$_2$C(=Q)—;
—CH$_2$C(=Q)CH$_2$—;
—C(=Q)CH$_2$—;
—SO$_2$NR$^{16}$—
—SO$_2$—;
—CH$_2$QCH$_2$—;
—CH$_2$Q—;
—CH$_2$NR$^{16}$—;
—CH$_2$CH$_2$—;
—CH=CH—;
—CH(OH)CH(OH)—;
—CH(OH)CH2—;
—CH$_2$CH(OH)—;
—CH(OH)—;
—C(=O)NH—NH—;
—C(—OR$^{16}$)=N—;
—C(—NR$^{16}$R$^{17}$)=N—;
—C(L)=N—;

Y and Y$^1$ are independently selected from the following:
—C(=Q)NR$^{16}$—;
—(CH$_2$)$_p$C(=Q)NR$^{16}$—;
—SO$_2$NR$^{16}$—;
—CH2NR$^{16}$—;
—C(L)=N—;
—C(—OR$^{16}$)=N—;
—C(—NR$^{16}$R$^{17}$)=N—;
—NR12C(=O)NR$^{16}$—;
—(CH$_2$)$_p$NR12C(=O)NR$^{16}$;
—OC(=O)NR$^{16}$—;
—(CH$_2$)$_p$OC(=O)NR$^{16}$—;

R$^{16}$ is H, benzyl or C$_1$-C$_4$ alkyl;
R$^{17}$ is H or C$_1$-C$_4$ alkyl;
p is 1 or 2;
Q is selected from oxygen or sulfur;
Q$^1$ is selected from oxygen, sulfur, NR$^{14}$ or a direct bond;
and pharmaceutically acceptable salts and prodrugs thereof.

2. A compound of claim 1 wherein:

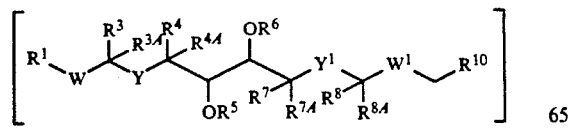

R$^1$ and R$^{10}$ are independently selected from the following:
hydrogen;
C$_1$-C$_6$ alkyl substituted with 0-2 R$^{11}$;
C$_2$-C$_4$ alkenyl substituted with 0-2 R$^{11}$;
C$_3$-C$_6$ cycloalkyl substituted with 0-2 R$^{11}$;
C$_6$-C$_{10}$ bicycloalkyl substituted with 0-2 R$^{11}$;
aryl substituted with 0-3 R$^{12}$;
a C$_6$-C$^{14}$ carbocyclic residue substituted with 0-2 R$^{12}$;
a heterocyclic ring system substituted with 0-2 R$^{12}$ selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, pyrrolidinyl, tetrahydrofuranyl, tetrahydroquinolinyl, tetrahydroisoquinolinyl, or decahydroisoquinolinyl;

R$^3$ and R$^6$ are independently selected from the following groups:
hydrogen;
C$_1$-C$_5$ alkyl substituted with 0-2 R$^{11}$;
C$_2$-C$_4$ alkenyl substituted with 0-2 R$^{11}$;
C$_3$-C$_6$ cycloalkyl substituted with 0-2 R$^{11}$;
with the proviso that the total number of non-hydrogen atoms comprising R$^3$ is less than or equal to 6, and the total number of non-hydrogen atoms comprising R$^8$ is less than or equal to 6;

R$^4$ and R$^7$ are independently selected from the following groups:
hydrogen;
C$_1$-C$_4$ alkyl substituted with 0-3 R$^{11}$;
C$_2$-C$_3$ alkenyl substituted with 0-3 R$^{11}$;

R$^{3A}$, R$^{4A}$, R$^{7A}$ and R$^{8A}$ are independently selected from the following groups:
hydrogen;
C$_1$-C$_2$ alkyl;

R$^5$ and R$^6$ are independently selected from the following groups:
hydrogen, or any other group that, when administered to a mammalian subject, cleaves to form the original diol in which R$^5$ and R$^6$ are hydrogen;

R$^{11}$ is selected from one or more of the following:
keto, halogen, cyano, —NR$^{13}$R$^{14}$, —CO$_2$R$^{13}$, —OC(=O)R$^{13}$, —OR$^{13}$, C$_2$-C$_6$ alkoxyalkyl, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$—; NR$^{14}$C(=O)OR$^{14}$, —OC(=O)NR$^{13}$R$^{14}$, NR$^{13}$C(=O)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, C$_1$-C$_4$ alkyl, C$_2$-C$_4$ alkenyl, C$_3$-C$_6$ cycloalkyl, C$_3$-C$_6$ cycloalkylmethyl;
a C$_5$-C$^{14}$ carbocyclic residue substituted with 0-3 R$^{12}$;
aryl substituted with 0-3 R$^{12}$;
or a heterocyclic ring system substituted with 0-2 R$^{12}$ selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, pyrrolidinyl, tetrahydrofuranyl, tetrahydroquinolinyl, tetrahydroisoquinolinyl, or decahydroisoquinolinyl;

R$^{12}$, when a substituent on carbon, is selected from one or more of the following:
phenyl, benzyl, phenethyl, phenoxy, benzyloxy, halogen, hydroxy, nitro, cyano, C$_1$-C$_4$ alkyl, C$_3$-C$_6$ cycloalkyl, C$_3$-C$_6$ cycloalkylmethyl, C$_7$-C$_{10}$ arylalkyl, alkoxy, —NR$^{13}$R$^{14}$, C$_2$-C$_6$ alkoxyalkyl, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —S(O)$_m$R$^{13}$, —SO$_2$NR$^{13}$R$^{14}$, —NHSO$_2$R$^{14}$;

or R$^{12}$ may be a 3- or 4-carbon chain attached to adjacent carbons on the ring to form a fused 5- or 6-membered ring, said 5- or 6-membered ring being optionally substituted on the aliphatic carbons with halogen, $C_1$-$C_4$ alkyl, $C_1$-$C_4$ alkoxy, hydroxy, or NR$^{13}$R$^{14}$; or, when R$_{12}$ is attached to a saturated carbon atom it may be carbonyl or thiocarbonyl;

and R$^{12}$, when a substituent on nitrogen, is selected from one or more of the following:

benzyl, hydroxy, $C_1$-$C_4$ alkoxy, $C_1$-$C_5$ hydroxyalkyl, $C_1$-$C_4$ alkyl, $C_3$-$C_6$ cycloalkyl, $C_3$-$C_6$ cycloalkylmethyl, $C_1$-$C_4$ alkoxycarbonyl, $C_1$-$C_4$ alkylcarbonyloxy, $C_1$-$C_4$ alkylcarbonyl, R$^{13}$ is H, benzyl or $C_1$-$C_4$ alkyl;

R$^{14}$ is H or $C_1$-$C_4$ alkyl;

or R$^{13}$R$^{14}$ can join to form (CH$_2$)$_4$, (CH$_2$)$_5$, (CH$_2$CH$_2$N(R$^{15}$)CH$_2$CH$_2$), or (CH$_2$CH$_2$OCH$_2$CH$_2$);

R$^{15}$ is H or CH$_3$;

m is 0, 1 or 2;

W and W$^1$ are independently selected from the following:
—NR$^{16}$C(=Q)NR$^{16}$—;
—C(=Q)NR$^{16}$—;
—OC(=Q)NR$^{16}$—;
—NR$^{16}$SO$_2$NR$^{16}$—
—SO$_2$NR$^{16}$—
—(CH$_2$)$_p$NR$^{16}$—;
—P(=O)(Q$^1$R$^{16}$)O—;
—SO$_2$NHC(=O)NH—;

Y and Y$^1$ are independently selected from the following:
—C(=Q)NR$^{16}$;
—NR12C(=O)NR$^{16}$—;
—OC(=O)NR$^{16}$—; or
—(CH$_2$)$_p$NR$^{13}$—;

R$^{16}$ is H or $C_1$-$C_2$ alkyl;

R$^{17}$ is H or $C_1$-$C_2$ alkyl;

p is 1 or 2;

Q is selected from oxygen or sulfur;

Q$^1$ is selected from oxygen, sulfur, NR$^{14}$ or a direct bond;

and pharmaceutically acceptable salts and prodrugs thereof.

3. A compound of claim 1 wherein:

R$^1$ and R$^{10}$ independently selected from the following:
hydrogen;
$C_1$-$C_6$ alkyl substituted with 0-1 R$^{18}$;
$C_2$-$C_4$ alkenyl substituted with 0-1 R$^{18}$;
aryl substituted with 0-1 R$^{19}$;
a heterocyclic ring system, substituted with 0-1 R$^{19}$, selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, pyrrolidinyl, tetrahydrofuranyl,, tetrahydroquinolinyl, tetrahydroisoquinolinyl, or decahydroisoquinolinyl;

wherein R$^{18}$ is selected from the following group:

keto, halogen, cyano, —NR$^{13}$R$^{14}$, —CO$_2$R$^{13}$, —OC(=O)R$^{13}$, —OR$^{13}$, $C_2$-$C_6$ alkoxyalkyl, —S(O)$_m$R$^{13}$, —NHC(=NH)NHR$^{13}$, —C(=O)NR$^{13}$R$^{14}$, —NR$^{14}$C(=O)R$^{13}$—, NR$^{14}$C(=O)OR$^{14}$, —OC(=O)NR$^{13}$R$^{14}$, NR$^{13}$C(=O)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, $C_1$-$C_4$ alkyl, $C_2$-$C_4$ alkenyl, or $C_3$-$C_6$ cycloalkyl;

a $C_5$-$C_{14}$ carbocyclic residue substituted with 0-3 R$^{19}$;

aryl substituted with 0-2 R$^{19}$;

or a heterocyclic ring system substituted with 0-2 R$^{19}$, selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, pyrrolidinyl, tetrahydrofuranyl,, tetrahydroquinolinyl, tetrahydroisoquinolinyl, or decahydroisoquinolinyl;

Wherein R$^{19}$, when a substituent on carbon, is selected from the following:

halogen, hydroxy, nitro, cyano, methyl, methoxy, —NR$^{13}$R$^{14}$, $C_1$-$C_4$ haloalkyl, $C_1$-$C_2$ alkoxycarbonyl, $C_1$-$C_2$ alkylcarbonyloxy, $C_1$-$C_2$ alkylcarbonylamino, —SO$_2$NR$^{13}$R$^{14}$, or —NHSO$_2$R$^{14}$;

and R$^{19}$, when a substituent on nitrogen, is $C_1$-$C_4$ alkyl;

R$^3$ and R$^8$ are independently selected from the following groups:
hydrogen;
$C_1$-$C_5$ alkyl substituted with 0-3 halogen or 0-1 R$^{20}$;
$C_2$-$C_4$ alkenyl substituted with 0-3 halogen or 0-1 R$^{20}$;
$C_3$-$C_6$ cycloalkyl substituted with 0-3 halogen or 0-1 R$^{20}$;

Wherein R$^{20}$ is selected from the following groups:
keto, amino, methylamino dimethylamino, —C(=O)NH$_2$, C(=O)NMe2, C(=O)NHMe, or $C_3$-$C_5$ cycloalkyl;

with the proviso that the total number of non-hydrogen atoms comprising R$^3$ is less than or equal to 6, and the total number of non-hydrogen atoms comprising R$^8$ is less than or equal to 6;

R$^4$ and R$^7$ are independently selected from the following groups:

$C_1$-$C_4$ alkyl substituted with 0-3 halogen or 0-1 R21, wherein R21 is selected from the following groups:
keto, halogen, cyano, —NR$^{13}$R$^{14}$, —CO$_2$R$^{13}$, —OC(=O)R$^{13}$, —OR$^{13}$, $C_2$-$C_4$ alkoxyalkyl, —SO(O)$_m$R$^{13}$, —$C_3$-$C_6$ cycloalkyl;

a $C_5$-$C_{10}$ carbocyclic residue substituted with 0-1 R$^{22}$;

aryl substituted with 0-1 R$^{22}$;

or a heterocyclic ring system, substituted with 0-1 R$^{22}$, selected from pyridyl, thienyl, indolyl, piperazyl, N-methylpiperazyl, or imidazolyl;

Wherein R$^{22}$ is selected from one or more of the following groups:

benzyl, benzyloxy, halogen, hydroxy, nitro, $C_1$-$C_4$ alkyl, $C_1$-$C_4$ alkoxy, amino, methylamino, dimethylamino, haloalkyl, haloalkoxy, —C(=O)$_2$R$^{14}$, or —OC(O$_2$)R$^{14}$;

R$^{3.4}$, R$^{4.4}$, R$^{7.4}$ and R$^{8.4}$ are hydrogen;

R$^5$ and R$^6$ are independently selected from the following groups:

hydrogen, or any other group that, when administered to a mammalian subject, cleaves to form the original diol in which $R^5$ and $R^6$ are hydrogen;

$R^{13}$ and $R^{14}$ are independently selected from H or $C_1$-$C_2$ alkyl;

m is 0, 1 or 2;

n and $n^1$ are 0;

W and W1 are independently selected from the following:
—$NR^{16}C(=Q)NR^{16}$—;
—$C(=O)NR^{16}$—;
—$OC(=O)NR^{16}$—;
—$(CH_2)_pNR^{16}$—;

Y and $Y^1$ are independently selected from the following:
—$C(=O)NR^{16}$—;
—$NR^{12}C(=O)NR^{16}$—;
—$OC(=O)NR^{16}$—; or
—$(CH_2)_pNR^{16}$—;

$R^{16}$ is H or methyl;

p is 1 or 2;

Q is selected from oxygen or sulfur;

and pharmaceutically acceptable salts and prodrugs thereof.

4. The compound of claim 1 which is: (S,R,R,S)-N-[4-[[(1,1-dimethylethoxy)carbonyl]amino]-2,3-dihydroxy-5-(1H-pyrrol-1-yl)-1-[(1H-pyrrol-1-yl)methyl]pentyl]-N2-formyl-L-valinamide.

5. The compound of claim 1 which is: (S,R,R,S)-N-[4-[[(1,1-dimethylethoxy)carbonyl]amino]-2,3-dihydroxy-5-phenyl-1-(phenylmethyl)pentyl]-N2-[[N-[(1H-benzimidazol-2-yl)methyl]-N-methylamino]carbonyl]-L-valinamide.

6. The compound of claim 1 which is: (S,R,R,S)-N-[4-[[(1,1-dimethylethoxy)carbonyl]amino]-2,3-dihydroxy-5-(4-pyridinyl)-1-(4-pyridinylmethyl)pentyl]-N2-formyl-L-valinamide.

7. The compound of claim 1 which is: (S,R,R,S)-N-[4-[[(1,1-dimethylethoxy)carbonyl]amino]-2,3-dihydroxy-5-(4-pyridinyl)-1-(4-pyridinylmethyl)pentyl]-N2-[(phenylmethoxy)carbonyl]-L-valinamide.

8. The compound of claim 1 which is: (S,R,R,S)-N2-[[1-(dimethylamino)cyclopropyl]carbonyl]-N-[4-[[(1,1-dimethylethoxy)carbonyl]amino]-2,3-dihydroxy-5-phenyl-1-(phenylmethyl)pentyl]-N-L-valinamide.

9. The compound of claim 1 which is: (S,R,R,S)-N-[4-[[(1,1-dimethylethoxy)carbonyl]amino]-2,3-dihydroxy-1-(phenylmethyl)hexyl]-N2-(N-methyl-L-alanyl)-L-valinamide.

10. The compound of claim 1 which is: (S,R,R,S)-(1,1-dimethylethyl) [4-[[[2-[(dimethylamino)methyl]-1H-imidazol-5-yl]carbonyl]amino]-2,3-dihydroxy-5-phenyl-1-(phenylmethyl)pentyl]carbamate.

11. The compound of claim 1 which is: (S,R,R,S)-N2-[[[2-[(dimethylamino)carbonyl]phenyl]methoxy]carbon yl]-N-[4-[[(1,1-dimethylethoxy)carbonyl]amino]-2,3-dihydroxy-5-phenyl-1-(phenylmethyl)pentyl]-L-valinamide.

12. The compound of claim 1 which is: (S,R,R,S)-N,N'-[2,3-dihydroxy-1,4-bis(phenylmethyl)-1,4-butanediyl]bis[N2-(4-aminobenzoyl)-L-valinamide].

13. The compound of claim 1 which is: (S,R,R,S)-N2-[[[4-(dimethylamino)phenyl]methoxy]carbonyl]-N-[4[[(1,1-dimethylethoxy)carbonyl]amino]-2,3-dihydroxy-5-phenyl-1-(phenylmethyl)pentyl]-L-valinamide.

14. The compound of claim 1 which is: (S,R,R,S)-N2-[[[4-[(dimethylamino)methyl]phenyl]methoxy]carbonyl]-N-[4-[[(1,1-dimethylethoxy)carbonyl]amino]-2,3-dihydroxy-5-phenyl-1-(phenylmethyl)pentyl]-L-valinamide.

15. The compound of claim 1 wherein $R^1$ and $R^2$ are identical, $R^3$ and $R^4$ are identical, $R^5$ and $R^6$ are identical, $X^1$ and $X^2$ are identical and $R^7$ and $R^8$ are identical.

16. A method for treatment of viral infections which comprises administering to a host in need of such treatment a pharmaceutically effective antiviral amount of a compound of claim 1.

17. A method for treatment of viral infections which comprises administering to a host in need of such treatment a pharmaceutically effective antiviral amount of a compound of claim 2.

18. A method for treatment of viral infections which comprises administering to a host in need of such treatment a pharmaceutically effective antiviral amount of a compound of claim 3.

19. A method for treatment of viral infections which comprises administering to a host in need of such treatment a pharmaceutically effective antiviral amount of the compound of claim 4.

20. A method for treatment of viral infections which comprises administering to a host in need of such treatment a pharmaceutically effective antiviral amount of the compound of claim 5.

21. A method for treatment of viral infections which comprises administering to a host in need of such treatment a pharmaceutically effective antiviral amount of the compound of claim 6.

22. A method for treatment of viral infections which comprises administering to a host in need of such treatment a pharmaceutically effective antiviral amount of the compound of claim 7.

23. A method for treatment of viral infections which comprises administering to a host in need of such treatment a pharmaceutically effective antiviral amount of the compound of claim 8.

24. A method for treatment of viral infections which comprises administering to a host in need of such treatment a pharmaceutically effective antiviral amount of the compound of claim 9.

25. A method for treatment of viral infections which comprises administering to a host in need of such treatment a pharmaceutically effective antiviral amount of the compound of claim 10.

26. A method for treatment of viral infections which comprises administering to a host in need of such treatment a pharmaceutically effective antiviral amount of the compound of claim 11.

27. A method for treatment of viral infections which comprises administering to a host in need of such treatment a pharmaceutically effective antiviral amount of the compound of claim 12.

28. A method for treatment of viral infections which comprises administering to a host in need of such treatment a pharmaceutically effective antiviral amount of the compound of claim 13.

29. A method for treatment of viral infections which comprises administering to a host in need of such treatment a pharmaceutically, effective antiviral amount of the compound of claim 14.

30. A pharmaceutical composition comprising a pharmaceutically acceptable carrier and a pharmaceutically effective antiviral amount of a compound of claim 1.

31. A pharmaceutical composition comprising a pharmaceutically acceptable carrier and a pharmaceutically effective antiviral amount of a compound of claim 2.

32. A pharmaceutical composition comprising a pharmaceutically acceptable carrier and a pharmaceutically effective antiviral amount of a compound of claim 3.

33. A pharmaceutical composition comprising a pharmaceutically acceptable carrier and a pharmaceutically effective antiviral amount of the compound of claim 4.

34. A pharmaceutical composition comprising a pharmaceutically acceptable carrier and a pharmaceutically effective antiviral amount of a compound of claim 5.

35. A pharmaceutical composition comprising a pharmaceutically acceptable carrier and a pharmaceutically effective antiviral amount of a compound of claim 6.

36. A pharmaceutical composition comprising a pharmaceutically acceptable carrier and a pharmaceutically effective antiviral amount of a compound of claim 7.

37. A pharmaceutical composition comprising a pharmaceutically acceptable carrier and a pharmaceutically effective antiviral amount of a compound of claim 8.

38. A pharmaceutical composition comprising a pharmaceutically acceptable carrier and a pharmaceutically effective antiviral amount of a compound of claim 9.

39. A pharmaceutical composition comprising a pharmaceutically acceptable carrier and a pharmaceutically effective antiviral amount of a compound of claim 10.

40. A pharmaceutical composition comprising a pharmaceutically acceptable carrier and a pharmaceutically effective antiviral amount of a compound of claim 11.

41. A pharmaceutical composition comprising a pharmaceutically acceptable carrier and a pharmaceutically effective antiviral amount of a compound of claim 12.

42. A pharmaceutical composition comprising a pharmaceutically acceptable carrier and a pharmaceutically effective antiviral amount of a compound of claim 13.

43. A pharmaceutical composition comprising a pharmaceutically acceptable carrier and a pharmaceutically effective antiviral amount of a compound of claim 14.

* * * * *